(12) United States Patent
Rowe

(10) Patent No.: US 6,673,900 B2
(45) Date of Patent: Jan. 6, 2004

(54) POLYPEPTIDE HORMONE-PHOSPHATONIN

(75) Inventor: Peter Rowe, London (GB)

(73) Assignee: University College London, London (GB)

( * ) Notice: Subject to any disclaimer, the term of this patent is extended or adjusted under 35 U.S.C. 154(b) by 49 days.

(21) Appl. No.: 10/132,920

(22) Filed: Apr. 25, 2002

(65) Prior Publication Data

US 2003/0064498 A1 Apr. 3, 2003

Related U.S. Application Data

(63) Continuation of application No. 09/434,185, filed on Nov. 4, 1999, now abandoned.

(51) Int. Cl.[7] ........................ C07K 14/00; C12P 21/06
(52) U.S. Cl. ................................. 530/350; 435/69.1
(58) Field of Search .................... 530/350; 435/69.1

(56) References Cited

PUBLICATIONS

Aschinberg, *J. Pediatr.,* 91 (1977) 55–60.
Carpenter, *Pediatric Clinics of North America,* 44 (1997) 443–466.
Drenzer, *Primer on Metabolic Bone Diseases and Disorders of Mineral Metabolism* (ed. Favus, M.J.) 184–188 (Am. Soc. Bone and Min. Res., Kelseyville, CA 1990).
Escarot, *J. Bone Miner. Res.,* 7 (1992) 215–220.
Escarot, *J. Bone Miner. Res.,* 10 (1995) 424–431.
Econs, *Am. J. Physiol.,* 273 (1997) F489–F498.
Francis, *Nat. Genet.,* 11 (1995), 130–136.
Francis, *Baillieres Clinical Endrocinology and Metabolism,* 11 (1997) 145–163.
Glorieux, *Arch. Pediat.,* 4 (1997) 102s–105s.
Grieff, *Current Opinion in Nephrology & Hypertension,* 6 (1997) 15–19.
Hanna, *Current Therapy in Endocrinology & Metabolism,* 6 (1997) 533–540.
Henderson, J. and Wang, D. *Curr. Opin. Orthopaedics,* 10 (1999) 3444–353.
Hilfiker, *PNAS,* 95(24) (1998) 14564–14569.
loakimidis, *The J. Rheumatology,* 21(6) (1994) 1162–1164.
Kumar, *Nephrol. Dial. Transplant,* 12 (1997) 11–13.
Lajeunesse, *Kidney Int.,* 50 (1996) 1531–1538.
Lyles, *Ann Intern. Med.,* 93 (1980) 275–278.
Meyer, *J. Bone Miner. Res.,* 4 (1989) 493–500.
Meyer, *J. Bone Miner. Res.,* 4(4) 1989) 523–532.
Miyauchi, *J. Clin. Endocrinol. Metab.,* 67 (1988) 46–53.
Morgan, *Arch. Intern. Med.,* 134 (1974) 549–552.
Nesbitt, *J. Clin. Invest.,* 89 (1992) 1453–1459.
Nesbitt, *J. Bone Miner. Res.,* 10 (1995) 1327–1333.
Nesbitt, *Endocrinology,* 137 (1996) 943–948.
Popovtzer, *Clin. Res.* 29 (1981), 418A (Abstract).
Qui, *GEnet. Res. Camb.,* 62 (1993) 39–43.
Rowe, *Hum. Genet.,* 94 (1994) 457–467.
Rowe, *Bone,* 18 (1996) 159–169.
Rowe, *Hum. Genet.,* 97 (1996) 345–352.
Rowe, *Hum. Mol. Genet.,* 6 (1997) 539–549.
Rowe, *Exp. Nephrol.,* 5 (1997) 355–363.
Rowe, *Current Opinion in Nephrology & Hypertension,* 7(4) (1977) 367–376.
Shane, *Journal of Bone and Mineral Research,* 12 (1997) 1502–1511.
Weidner, *Cancer,* 59 (1987) 1442–1454.

*Primary Examiner*—Yvonne Eyler
*Assistant Examiner*—Janet L. Andres
(74) *Attorney, Agent, or Firm*—Karl Bozicevic; Bozicevic, Field & Francis LLP

(57) ABSTRACT

The present invention relates to a novel human protein called phosphatonin, and isolated polynucleotides encoding this protein. Also provided are vectors, host cells, antibodies, and recombinant methods for producing this human protein. The invention further relates to diagnostic and therapeutic methods useful for diagnosing and treating disorders related to this novel human protein.

1 Claim, 19 Drawing Sheets

```
V  N  K  E  Y  S  I  S  N  K  E  N  T  H  N  G  L  R  M  S
GTGAATAAAGAATATAGTATCAGTAACAAAGAGAATACTCACAATGGCCTGAGGATGTCA    60

I  Y  P  K  S  T  G  N  K  G  F  E  D  G  D  D  A  I  S  K
ATTTATCCTAAGTCAACTGGGAATAAAGGGTTTGAGGATGGAGATGATGCTATCAGCAAA   120

L  H  D  Q  E  E  Y  G  A  A  L  I  R  N  N  M  Q  H  I  M
CTACATGACCAAGAAGAATATGGCGCAGCTCTCATCAGAAATAACATGCAACATATAATG   180

G  P  C  T  A  I  K  L  L  G  E  E  N  K  E  N  T  P  R  N
GGGCCAGTGACTGCGATTAAACTCCTGGGGGAAGAAAACAAAGAGAACACACCTAGGAAT   240

V  L  N  I  I  P  A  S  M  N  Y  A  K  A  H  S  K  D  K  K
GTTCTAAACATAATCCCAGCAAGTATGAATTATGCTAAAGCACACTCGAAGGATAAAAAG   300

K  P  Q  R  D  S  Q  A  Q  K  S  P  V  K  S  K  S  T  H  R
AAGCCTCAAAGAGATTCCCAAGCCCAGAAAAGTCCAGTAAAAAGCAAAAGCACCCATCGT   360

I  Q  H  N  I  D  Y  L  K  H  L  S  K  V  K  K  I  P  S  D
ATTCAACACAACATTGACTACCTAAAACATCTCTCAAAAGTCAAAAAAATCCCCAGTGAT   420

F  E  G  S  G  Y  T  D  L  Q  E  R  G  D  N  D  I  S  P  F
TTTGAAGGCAGCGGTTATACAGATCTTCAAGAGACAGGGGACAATGATATATCTCCTTTC   480

S  G  D  G  Q  P  F  K  D  I  P  G  K  G  E  A  T  G  P  D
AGTGGGGACGGCCAACCTTTTAAGGACATTCCTGGTAAAGGAGAAGCTACTGGTCCTGAC   540

L  E  G  K  D  I  Q  T  G  F  A  G  P  S  E  A  E  S  T  H
CTAGAAGGCAAAGATATTCAAACAGGGTTTGCAGGCCCAAGTGAAGCTGAGAGTACTCAT   600

L  D  T  K  K  P  G  Y  N  E  I  P  E  R  E  E  N  G  G  N
CTTGACACAAAAAAGCCAGGTTATAATGAGATCCCAGAGAGAGAAGAAAATGGTGGAAAT   660

T  I  G  T  R  D  E  T  A  K  E  A  D  A  V  D  V  S  L  V
ACCATTGGAACTAGGGATGAAACTGCGAAAGAGGCAGATGCTGTTGATGTCAGCCTTGTA   720

E  G  S  N  D  I  M  G  S  T  N  F  K  E  L  P  G  R  E  G
GAGGGCACCAACGATATCATGGGTAGTACCAATTTTAAGGAGCTCCCTGGAAGAGAAGGA   780
```

*FIG. 8*

```
      N  R  V  D  A  G  S  Q  N  A  H  Q  G  K  V  E  F  H  Y  P
      AACAGAGTGGATGCTGGCAGCCAAAATGCTCACCAAGGGAAGGTTGAGTTTCATTACCCT      840

P  A  P  S  K  E  K  R  K  E  G  S  S  D  A  A  E  S  T  N
      CCTGCACCCTCAAAAGAGAAAAGAAAAGAAGGCAGTAGTCATGCAGCTCAAAGTACCAAC      900

Y  N  E  I  P  K  N  G  K  G  S  T  R  K  G  V  D  H  S  N
      TATAATGAAATTCCTAAAAATGGCAAAGGCAGTACCAGAAAGGGTGTAGATCATTCTAAT      960

R  N  Q  A  T  L  N  E  K  Q  R  F  P  S  K  G  K  S  Q  C
      CTGCCCATTCCTTCTCGTGGTCTTGATAATGAAATCAAAAACGAAATGGATTCCTTTAAT     1080

G  P  S  H  E  N  I  I  T  H  G  R  K  Y  H  Y  V  P  H  R
      GGCCCCAGTCATGAGAATATAATAACACATGGCAGAAAATATCATTATGTACCCCACAGA     1140

Q  N  N  S  T  R  N  K  G  M  P  Q  G  K  G  S  W  G  R  Q
      CAAAATAATTCTACACGGAATAAGGGTATGCCACAAGGGAAAGGCTCCTGGGGTAGACAA     1200

P  H  S  N  R  R  F  S  S  R  R  R  D  D  S  S  E  S  S  D
      CCCCATTCCAACAGGAGGTTTAGTTCCCGTAGAAGGGATGACAGTAGTGAGTCATCTGAC     1260

S  G  S  S  S  E  S  D  G  D  *
      AGTGGCAGTTCAAGTGAGAGCGATGGTGACTAGTCCACCAGGAGTTCCCAGCGGGGTGAC     1320

AGTCTGAAGACCTCGTCACCTGTGAGTTGATGTAGAGGAGAGCCACCTGACACCTGACCA     1380

GGTGAAGAGAGGATAGAGTGAAGAACTGAGTGAGCCAAGAATCCTGGTCTCCTTGGGGGA     1440

ATTTTTGCTATCTTAATAGTCACAGTATAAAATTCTATTAAAGGCTATAATGTTTTTAAG     1500

CAAAAAAAAATCATTACAGATCTATGAAATAGGTAACATTTGAGTAGGTGTCATTTAAAA     1560

ATAGTTGGTGAATGTCACAAATGCCTTCTATGTTGTTTGCTCTGTAGACATGAAAATAAA     1620

CAATATCTCTCGATGATAAAAAAAAAAAAAAAAA                              1655
```

FIG. 8 (continued)

Regions of homology to C-terminus of MEPE and C-terminal end of DSSP (dentin phoshoryn portion)

Three regions of homology to C-terminus of MEPE and C-terminal end of DSSP (dentin phoshoryn portion)

SEQUENCE LISTING

<160> NUMBER OF SEQ ID NOS: 30

<210> SEQ ID NO 1
<211> LENGTH: 1655
<212> TYPE: DNA
<213> ORGANISM: Homo sapien

<400> SEQUENCE: 1

```
gtgaataaag aatatagtat cagtaacaaa gagaatactc acaatggcct gaggatgtca      60
atttatccta agtcaactgg gaataaaggg tttgaggatg gagatgatgc tatcagcaaa     120
ctacatgacc aagaagaata tggcgcagct ctcatcagaa ataacatgca acatataatg     180
gggccagtga ctgcgattaa actcctgggg gaagaaaaca aagagaacac acctaggaat     240
gttctaaaca taatcccagc aagtatgaat tatgctaaag cacactcgaa ggataaaaag     300
aagcctcaaa gagattccca agcccagaaa agtccagtaa aaagcaaaag cacccatcgt     360
attcaacaca acattgacta cctaaaacat ctctcaaaag tcaaaaaaat ccccagtgat     420
tttgaaggca gcggttatac agatcttcaa gagagagggg acaatgatat atctcctttc     480
agtggggacg gccaacctttt taaggacatt cctggtaaag gagaagctac tggtcctgac     540
ctagaaggca aagatattca aacagggttt gcaggcccaa gtgaagctga gagtactcat     600
cttgacacaa aaaagccagg ttataatgag atcccagaga gagaagaaaa tggtggaaat     660
accattggaa ctagggatga aactgcgaaa gaggcagatg ctgttgatgt cagccttgta     720
gagggcagca acgatatcat gggtagtacc aattttaagg agctccctgg aagagaagga     780
aacagagtgg atgctggcag ccaaaatgct caccaaggga aggttgagtt tcattaccct     840
cctgcaccct caaaagagaa aagaaaagaa ggcagtagtg atgcagctga aagtaccaac     900
tataatgaaa ttcctaaaaa tggcaaaggc agtaccagaa agggtgtaga tcattctaat     960
aggaaccaag caaccttaaa tgaaaaacaa aggtttccta gtaagggcaa aagtcagggc    1020
ctgcccattc cttctcgtgg tcttgataat gaaatcaaaa acgaaatgga ttcctttaat    1080
ggccccagtc atgagaatat aataacacat ggcagaaaat atcattatgt accccacaga    1140
caaaataatt ctacacggaa taagggtatg ccacaaggga aaggctcctg gggtagacaa    1200
ccccattcca acaggaggtt tagttcccgt agaagggatg acagtagtga gtcatctgac    1260
agtggcagtt caagtgagag cgatggtgac tagtccacca ggagttccca gcggggtgac    1320
agtctgaaga cctcgtcacc tgtgagttga tgtagaggag agccacctga cagctgacca    1380
ggtgaagaga ggatagagtg aagaactgag tgagccaaga atcctggtct ccttggggga    1440 attttttgcta tcttaatagt cacagtataa aattctatta aaggctataa tgtttttaag    1500
caaaaaaaaa tcattacaga tctatgaaat aggtaacatt tgagtaggtg tcatttaaaa    1560
atagttggtg aatgtcacaa atgccttcta tgttgtttgc tctgtagaca tgaaaataaa    1620
caatatctct cgatgataaa aaaaaaaaaa aaaaa                               1655
```

<210> SEQ ID NO 2
<211> LENGTH: 430
<212> TYPE: PRT
<213> ORGANISM: Homo sapien

<400> SEQUENCE: 2

```
Val Asn Lys Glu Tyr Ser Ile Ser Asn Lys Glu Asn Thr His Asn Gly
 1               5                  10                  15
Leu Arg Met Ser Ile Tyr Pro Lys Ser Thr Gly Asn Lys Gly Phe Glu
            20                  25                  30
Asp Gly Asp Asp Ala Ile Ser Lys Leu His Asp Gln Glu Glu Tyr Gly
        35                  40                  45
Ala Ala Leu Ile Arg Asn Asn Met Gln His Ile Met Gly Pro Val Thr
    50                  55                  60
Ala Ile Lys Leu Leu Gly Glu Glu Asn Lys Glu Asn Thr Pro Arg Asn
65                  70                  75                  80
Val Leu Asn Ile Ile Pro Ala Ser Met Asn Tyr Ala Lys Ala His Ser
                85                  90                  95
Lys Asp Lys Lys Lys Pro Gln Arg Asp Ser Gln Ala Gln Lys Ser Pro
           100                 105                 110
Val Lys Ser Lys Ser Thr His Arg Ile Gln His Asn Ile Asp Tyr Leu
       115                 120                 125
Lys His Leu Ser Lys Val Lys Lys Ile Pro Ser Asp Phe Glu Gly Ser
   130                 135                 140
Gly Tyr Thr Asp Leu Gln Glu Arg Gly Asp Asn Asp Ile Ser Pro Phe
145                 150                 155                 160
Thr Gly Pro Asp Leu Glu Gly Lys Asp Ile Gln Thr Gly Phe Ala Gly
                165                 170                 175
Ser Gly Asp Gly Gln Pro Phe Lys Asp Ile Pro Gly Lys Gly Glu Ala
           180                 185                 190
Pro Ser Glu Ala Glu Ser Thr His Leu Asp Thr Lys Lys Pro Gly Tyr
       195                 200                 205
Asn Glu Ile Pro Glu Arg Glu Asn Gly Gly Asn Thr Ile Gly Thr
   210                 215                 220
Arg Asp Glu Thr Ala Lys Glu Ala Asp Ala Val Asp Val Ser Leu Val
225                 230                 235                 240
Glu Gly Ser Asn Asp Ile Met Gly Ser Thr Asn Phe Lys Glu Leu Pro
                245                 250                 255
Gly Arg Glu Gly Asn Arg Val Asp Ala Gly Ser Gln Asn Ala His Gln
           260                 265                 270
Gly Lys Val Glu Phe His Tyr Pro Pro Ala Pro Ser Lys Glu Lys Arg
       275                 280                 285
Lys Glu Gly Ser Ser Asp Ala Ala Glu Ser Thr Asn Tyr Asn Glu Ile
   290                 295                 300
Pro Lys Asn Gly Lys Gly Ser Thr Arg Lys Gly Val Asp His Ser Asn
305                 310                 315                 320
Arg Asn Gln Ala Thr Leu Asn Glu Lys Gln Arg Phe Pro Ser Lys Gly
                325                 330                 335
Lys Ser Gln Gly Leu Pro Ile Pro Ser Arg Gly Leu Asp Asn Glu Ile
           340                 345                 350
Lys Asn Glu Met Asp Ser Phe Asn Gly Pro Ser His Glu Asn Ile Ile
       355                 360                 365
Thr His Gly Arg Lys Tyr His Tyr Val Pro His Arg Gln Asn Asn Ser
   370                 375                 380
```

```
Thr Arg Asn Lys Gly Met Pro Gln Gly Lys Gly Ser Trp Gly Arg Gln
385                 390                 395                 400

Pro His Ser Asn Arg Arg Phe Ser Ser Arg Arg Arg Asp Asp Ser Ser
                405                 410                 415

Glu Ser Ser Asp Ser Gly Ser Ser Ser Glu Ser Asp Gly Asp
                420                 425                 430

<210> SEQ ID NO 3
<211> LENGTH: 4
<212> TYPE: PRT
<213> ORGANISM: Artificial Sequence
<220> FEATURE:
<223> OTHER INFORMATION: synthesized peptide

<400> SEQUENCE: 3

Ser Gly Asp Gly
 1

<210> SEQ ID NO 4
<211> LENGTH: 7
<212> TYPE: PRT
<213> ORGANISM: Artificial Sequence
<220> FEATURE:
<223> OTHER INFORMATION: synthesized peptide

<400> SEQUENCE: 4

Ala Asp Ala Val Asp Val Ser
 1               5

<210> SEQ ID NO 5
<211> LENGTH: 22
<212> TYPE: PRT
<213> ORGANISM: Artificial Sequence
<220> FEATURE:
<223> OTHER INFORMATION: synthesized peptide

<400> SEQUENCE: 5

Ser Ser Arg Arg Arg Asp Asp Ser Ser Glu Ser Ser Asp Ser Gly Ser
 1               5                  10                  15

Ser Ser Glu Ser Asp Gly
                20

<210> SEQ ID NO 6
<211> LENGTH: 21
<212> TYPE: PRT
<213> ORGANISM: Artificial Sequence
<220> FEATURE:
<223> OTHER INFORMATION: synthesized peptide

<400> SEQUENCE: 6

Ser Ser Arg Ser Lys Glu Asp Ser Asn Ser Thr Glu Ser Lys Ser Ser
 1               5                  10                  15

Ser Glu Glu Asp Gly
                20

<210> SEQ ID NO 7
<211> LENGTH: 28
<212> TYPE: PRT
<213> ORGANISM: Artificial Sequence
<220> FEATURE:
<223> OTHER INFORMATION: chemical synthesis in laboratory

<400> SEQUENCE: 7

Asp Ser Ser Glu Ser Ser Asp Ser Gly Ser Ser Ser Glu Ser Asp Ser
```

```
                1               5              10              15
Ser Glu Ser Ser Asp Ser Gly Ser Ser Ser Glu Ser
                20              25
```

<210> SEQ ID NO 8
<211> LENGTH: 38
<212> TYPE: DNA
<213> ORGANISM: Artificial Sequence
<220> FEATURE:
<223> OTHER INFORMATION: chemical synthesis in laboratory

<400> SEQUENCE: 8
gacgacgaca aggtgaataa agaatatagt atcagtaa                                38

<210> SEQ ID NO 9
<211> LENGTH: 35
<212> TYPE: DNA
<213> ORGANISM: Artificial Sequence
<220> FEATURE:
<223> OTHER INFORMATION: nucleotide sequence

<400> SEQUENCE: 9
ggaacaagac ccgtctagtc accatcgctc tcact                                   35

<210> SEQ ID NO 10
<211> LENGTH: 15
<212> TYPE: PRT
<213> ORGANISM: Artificial Sequence
<220> FEATURE:
<223> OTHER INFORMATION: synthesized peptide

<400> SEQUENCE: 10

```
Asp Asp Ser Ser Glu Ser Ser Asp Ser Gly Ser Ser Ser Glu Ser
 1               5              10              15
```

<210> SEQ ID NO 11
<211> LENGTH: 16
<212> TYPE: PRT
<213> ORGANISM: Artificial Sequence
<220> FEATURE:
<223> OTHER INFORMATION: synthesized peptide

<400> SEQUENCE: 11

```
Asp Asp Ser Ser Glu Ser Ser Asp Ser Gly Ser Ser Ser Glu Ser Asp
 1               5              10              15
```

<210> SEQ ID NO 12
<211> LENGTH: 22
<212> TYPE: PRT
<213> ORGANISM: Artificial Sequence
<220> FEATURE:
<223> OTHER INFORMATION: synthesized peptide

<400> SEQUENCE: 12

```
Ser Ser Arg Arg Arg Asp Asp Ser Ser Glu Ser Ser Asp Ser Gly Ser
 1               5              10              15
Ser Ser Glu Ser Asp Gly
                20
```

<210> SEQ ID NO 13
<211> LENGTH: 14
<212> TYPE: PRT
<213> ORGANISM: Artificial Sequence
<220> FEATURE:
<223> OTHER INFORMATION: synthesized peptide

<400> SEQUENCE: 13

Asp Ser Ser Asp Ser Ser Asp Ser Ser Ser Ser Asp Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: synthesized peptide

<400> SEQUENCE: 14

Asp Asp Ser Ser Asp Ser Ser Asp Ser Ser Asp Ser Ser Asp Ser
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: synthesized peptide

<400> SEQUENCE: 15

Asp Ser Ser Asp Ser Ser Asp Ser Asn Ser Ser Ser Asp Ser
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthesized peptide

<400> SEQUENCE: 16

Asp Ser Ser Glu Ser Ser Asp Ser Ser Asn Ser Ser Asp Ser
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthesized peptide

<400> SEQUENCE: 17

Asp Ser Ser Asp Ser Ser Asp Ser Ser Asn Ser Ser Asp Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: synthesized peptide

<400> SEQUENCE: 18

Asp Asp Ser His Gln Ser Asp Glu Ser His His Ser Asp Glu Ser Asp
1               5                   10                  15

<210> SEQ ID NO 19
<211> LENGTH: 11
<212> TYPE: PRT
<213> ORGANISM: Artificial Sequence
<220> FEATURE:
<223> OTHER INFORMATION: synthesized peptide

<400> SEQUENCE: 19

Ser Asp Glu Ser His His Ser Asp Glu Ser Asp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthesized peptide

<400> SEQUENCE: 20

Ser Asp Ser Ser Ser Ser Ser Asp Ser Ser Asp
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthesized peptide

<400> SEQUENCE: 21

Ser Asp Ser Ser Asp Ser Ser Asp Ser Ser Asp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthesized peptide

<400> SEQUENCE: 22

Ser Asp Ser Ser Asp Ser Ser Asp Ser Ser Asn
1               5                   10

<210> SEQ ID NO 23
<211> LENGTH: 21
<212> TYPE: PRT
<213> ORGANISM: Artificial Sequence
<220> FEATURE:
<223> OTHER INFORMATION: synthesized peptide

<400> SEQUENCE: 23

Ser Ser Arg Ser Lys Glu Asp Ser Asn Ser Thr Glu Ser Lys Ser Ser
1               5                   10                  15

Ser Glu Glu Asp Gly
            20

<210> SEQ ID NO 24
<211> LENGTH: 25
<212> TYPE: DNA
<213> ORGANISM: Artificial Sequence
<220> FEATURE:
<223> OTHER INFORMATION: synthesized peptide

<400> SEQUENCE: 24
ggttatacag atcttcaaga gagag                                         25

<210> SEQ ID NO 25
<211> LENGTH: 24
<212> TYPE: DNA
<213> ORGANISM: Artificial Sequence
<220> FEATURE:
<223> OTHER INFORMATION: synthesized peptide

```
<400> SEQUENCE: 25
gttggtactt tcagctgcat cact                                              24

<210> SEQ ID NO 26
<211> LENGTH: 2013
<212> TYPE: DNA
<213> ORGANISM: Homo sapien

<400> SEQUENCE: 26
cacacagctt tgcttagttt tctccggcac gagcaggtat tctgaaggtg aaagatacca        60
gagattctca aagatgcgag ttttctgtgt gggactactc cttttcagtg tgacctgggc       120
agcaccaaca tttcaaccac agactgagaa aactaagcaa agctgtgtgg aagagcagag       180
gcaggaagaa aaaacaaag acaatattgg ttttcaccat ttgggcaaga gaataaatca        240
agagctatca tctaaagaaa atattgtcca ggaaagaaag aaagatttgt ccctttctga       300
agccagtgag aataagggaa gtagtaaatc tcaaaattat ttcacaaata gacagagact       360
gaataaagaa tatagtatca gtaacaaaga gaatactcac aatggcctga ggatgtcaat       420
ttatcctaag tcaactggga ataaagggtt tgaggatgga gatgatgcta tcagcaaact       480
acatgaccaa gaagaatatg gcgcagctct catcagaaat aacatgcaac atataatggg       540
gccagtgact gcgattaaac tcctggggga agaaaacaaa gagaacacac ctaggaatgt       600
tctaaacata tcccagcaa gtatgaatta tgctaaagca cactcgaagg ataaaaagaa        660
gcctcaaaga gattcccaag cccagaaaag tccagtaaaa agcaaaagca cccatcgtat       720
tcaacacaac attgactacc taaaacatct ctcaaaagtc aaaaaaatcc ccagtgattt       780
tgaaggcagc ggttatacag atcttcaaga gagagggga aatgatatat ctcctttcag        840
tggggacggc caacctttta aggacattcc tggtaaagga aagctactg gtcctgacct        900 agaaggcaaa gatattcaaa cagggtttgc aggcccaagt gaagctgaga gtactcatct       960
tgacacaaaa aagccaggtt ataatgagat cccagagaga aagaaaatg gtggaaatac      1020 cattggaact agggatgaaa ctgcgaaaga ggcagatgct gttgatgtca gccttgtaga      1080
gggcagcaac gatatcatgg gtagtaccaa ttttaaggag ctccctggaa gagaaggaaa      1140
cagagtggat gctggcagcc aaaatgctca ccaagggaag gttgagtttc attaccctcc      1200
tgcaccctca aaagagaaaa gaaagaagg cagtagtgat gcagctgaaa gtaccaacta      1260
taatgaaatt cctaaaaatg gcaaaggcag taccagaaag ggtgtagatc attctaatag      1320
gaaccaagca accttaaatg aaaaacaaag gtttcctagt aagggcaaaa gtcagggcct      1380
gcccattcct tctcgtggtc ttgataatga atcaaaaac gaaatggatt cctttaatgg       1440
ccccagtcat gagaatataa taacacatgg cagaaaatat cattatgtac cccacagaca      1500
aaataattct acacggaata agggtatgcc acaagggaaa ggctcctggg gtagacaacc      1560
ccattccaac aggaggttta gttcccgtag aagggatgac agtagtgagt catctgacag      1620
tggcagttca agtgagagcg atggtgacta gtccaccagg agttcccagc ggggtgacag      1680
tctgaagacc tcgtcacctg tgagttgatg tagaggagag ccacctgaca gctgaccagg      1740
tgaagagagg atagagtgaa gaactgagtg agccaagaat cctggtctcc ttgggggaat      1800
ttttgctatc ttaatagtca cagtataaaa ttctattaaa ggctataatg ttttttaagca     1860 aaaaaaaatc attacagatc tatgaaatag gtaacatttg agtaggtgtc atttaaaaat      1920
agttggtgaa tgtcacaaat gccttctatg ttgtttgctc tgtagacatg aaaataaaca      1980
atatctctcg atgataaaaa aaaaaaaaaa aaa                                   2013
```

<210> SEQ ID NO 27
<211> LENGTH: 525
<212> TYPE: PRT
<213> ORGANISM: Homo sapien

<400> SEQUENCE: 27

```
Met Arg Val Phe Cys Val Gly Leu Leu Leu Phe Ser Val Thr Trp Ala
 1               5                  10                  15

Ala Pro Thr Phe Gln Pro Gln Thr Glu Lys Thr Lys Gln Ser Cys Val
            20                  25                  30

Glu Glu Gln Arg Gln Glu Glu Lys Asn Lys Asp Asn Ile Gly Phe His
        35                  40                  45

His Leu Gly Lys Arg Ile Asn Gln Glu Leu Ser Ser Lys Glu Asn Ile
    50                  55                  60

Val Gln Glu Arg Lys Lys Asp Leu Ser Leu Ser Glu Ala Ser Glu Asn
65                  70                  75                  80

Lys Gly Ser Ser Lys Ser Gln Asn Tyr Phe Thr Asn Arg Gln Arg Leu
                85                  90                  95

Asn Lys Glu Tyr Ser Ile Ser Asn Lys Glu Asn Thr His Asn Gly Leu
            100                 105                 110

Arg Met Ser Ile Tyr Pro Lys Ser Thr Gly Asn Lys Gly Phe Glu Asp
        115                 120                 125

Gly Asp Asp Ala Ile Ser Lys Leu His Asp Gln Glu Glu Tyr Gly Ala
    130                 135                 140

Ala Leu Ile Arg Asn Asn Met Gln His Ile Met Gly Pro Val Thr Ala
145                 150                 155                 160

Ile Lys Leu Leu Gly Glu Glu Asn Lys Glu Asn Thr Pro Arg Asn Val
                165                 170                 175

Leu Asn Ile Ile Pro Ala Ser Met Asn Tyr Ala Lys Ala His Ser Lys
            180                 185                 190

Asp Lys Lys Lys Pro Gln Arg Asp Ser Gln Ala Gln Lys Ser Pro Val
        195                 200                 205

Lys Ser Lys Ser Thr His Arg Ile Gln His Asn Ile Asp Tyr Leu Lys
    210                 215                 220

His Leu Ser Lys Val Lys Lys Ile Pro Ser Asp Phe Glu Gly Ser Gly
225                 230                 235                 240

Tyr Thr Asp Leu Gln Glu Arg Gly Asp Asn Asp Ile Ser Pro Phe Ser
                245                 250                 255

Gly Asp Gly Gln Pro Phe Lys Asp Ile Pro Gly Lys Gly Glu Ala Thr
            260                 265                 270

Gly Pro Asp Leu Glu Gly Lys Asp Ile Gln Thr Gly Phe Ala Gly Pro
        275                 280                 285

Ser Glu Ala Glu Ser Thr His Leu Asp Thr Lys Lys Pro Gly Tyr Asn
    290                 295                 300

Glu Ile Pro Glu Arg Glu Glu Asn Gly Gly Asn Thr Ile Gly Thr Arg
305                 310                 315                 320

Asp Glu Thr Ala Lys Glu Ala Asp Ala Val Asp Val Ser Leu Val Glu
                325                 330                 335
```

```
Gly Ser Asn Asp Ile Met Gly Ser Thr Asn Phe Lys Glu Leu Pro Gly
                340                 345                 350

Arg Glu Gly Asn Arg Val Asp Ala Gly Ser Gln Asn Ala His Gln Gly
            355                 360                 365

Lys Val Glu Phe His Tyr Pro Pro Ala Pro Ser Lys Glu Lys Arg Lys
        370                 375                 380

Glu Gly Ser Ser Asp Ala Ala Glu Ser Thr Asn Tyr Asn Glu Ile Pro
385                 390                 395                 400

Lys Asn Gly Lys Gly Ser Thr Arg Lys Gly Val Asp His Ser Asn Arg
                405                 410                 415

Asn Gln Ala Thr Leu Asn Glu Lys Gln Arg Phe Pro Ser Lys Gly Lys
            420                 425                 430

Ser Gln Gly Leu Pro Ile Pro Ser Arg Gly Leu Asp Asn Glu Ile Lys
        435                 440                 445

Asn Glu Met Asp Ser Phe Asn Gly Pro Ser His Glu Asn Ile Ile Thr
    450                 455                 460

His Gly Arg Lys Tyr His Tyr Val Pro His Arg Gln Asn Asn Ser Thr
465                 470                 475                 480

Arg Asn Lys Gly Met Pro Gln Gly Lys Gly Ser Trp Gly Arg Gln Pro
                485                 490                 495

His Ser Asn Arg Arg Phe Ser Ser Arg Arg Arg Asp Asp Ser Ser Glu
                500                 505                 510

Ser Ser Asp Ser Gly Ser Ser Ser Glu Ser Asp Gly Asp
            515                 520                 525

<210> SEQ ID NO 28
<211> LENGTH: 21
<212> TYPE: DNA
<213> ORGANISM: Artificial Sequence
<220> FEATURE:
<223> OTHER INFORMATION: synthesized peptide

<400> SEQUENCE: 28
tcttccccca ggagtttaat c                                      21

<210> SEQ ID NO 29
<211> LENGTH: 25
<212> TYPE: DNA
<213> ORGANISM: Artificial Sequence
<220> FEATURE:
<223> OTHER INFORMATION: synthesized peptide

<400> SEQUENCE: 29
ggccgcaatt aaccctcact aaagg                                  25

<210> SEQ ID NO 30
<211> LENGTH: 24
<212> TYPE: DNA
<213> ORGANISM: Artificial Sequence
<220> FEATURE:
<223> OTHER INFORMATION: synthesized peptide

<400> SEQUENCE: 30
cacacagctt tgcttagttt tctc                                   24
```

POLYPEPTIDE HORMONE-PHOSPHATONIN

CROSS-REFERENCE

This application is a continuation of earlier filed U.S. patent application Ser. No. 09/434,185, filed Nov. 4, 1999, now abandoned, which is incorporated herein by reference in its entirety and to which application we claim priority under 35 USC §120.

FIELD OF THE INVENTION

The present invention relates to a polypeptide which is involved in the regulation of phosphate metabolism. More specifically, the present invention relates to a novel polypeptide Metastatic-tumor Excreted Phosphaturic-Element (MEPE) or "phosphatonin". This invention also relates to genes and polynucleotides encoding phosphatonin polypeptides, as well as vectors, host cells, antibodies directed to phosphatonin polypeptides, and the recombinant methods for producing the same. Also provided are diagnostic methods for detecting disorders relating to phosphate metabolism, and therapeutic methods for treating such disorders. The invention further relates to screening methods for identifying agonists and antagonists of phosphatonin activity.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

Phosphate plays a central role in many of the basic processes essential to the cell and the mineralization of bone. In particular, skeletal mineralization is dependent on the regulation of phosphate and calcium in the body and any disturbances in phosphate-calcium homeostasis can have severe repercussions on the integrity of bone. In the kidney, phosphate is lost passively into the glomerular filtrate and is actively reabsorbed via a sodium (Na+) dependent phosphate cotransporter. In the intestine, phosphate is absorbed from foods. A sodium (Na+) dependent phosphate cotransporter was found to be expressed in the intestine and recently cloned (Hilfiker, PNAS 95(24) (1998), 14564–14569). The liver, skin and kidney are involved in the conversion of vitamin D3 to its active metabolite, calcitriol, which plays an active role in the maintenance of phosphate balance and bone mineralization.

Vitamin D deficiency causes rickets in children and osteomalacia in adults. Both conditions are characterized by failure of calcification of osteoid, which is the matrix of bone. There are also several non-dietary conditions which can lead to rickets, including X-linked vitamin D resistant hypophosphatemic rickets (HYP), hereditary hypercalciuria with hypophosphatemic rickets (HHRH), Dent's disease including certain types of renal Fanconi syndrome, renal I alpha-hydroxylase deficiency (VDDR 1), defects in 1,25-dihydroxy vitamin D3 receptor (end organ resistance, VDDR II), and oncogenic hypophosphatemic osteomalacia (OHO). Thus, a number of familial diseases have been characterized that result in disorders of phosphate uptake, vitamin D metabolism and bone mineralization. Recently a gene has been cloned and characterized that is defective in patients with X-linked hypophosphatemic rickets (PHEX) (Francis, Nat. Genet. 11 (1995), 130–136; Rowe, Hum. Genet. 97 (1996), 345–352; Rowe, Hum. Mol. Genet. 6 (1997), 539–549). The PHEX gene is a type II glycoprotein and a member of a family (M13), of Zn metalloendopeptidases. PHEX is proposed to function by processing a factor that plays a role in phosphate homeostasis and skeletal mineralization (Rowe, Exp. Nephrol. 5 (1997), 355–363; Rowe, Current Opinion in Nephrology & Hypertension 7(4) (1998), 367–376). Oncogenic hypophosphatemic osteomalacia (OHO), has many similarities to HYP with an overlapping pathophysiology, but different primary defects (Rowe, Exp. Nephrol. 5 (1997), 355–363; Rowe, Current Opinion in Nephrology & Hypertension 7(4) (1998), 367–376; Drezner in Primer on Metabolic Bone Diseases and Disorders of Mineral Metabolism (ed. Favus, M. J.) 184–188 (Am. Soc. Bone and Min. Res., Kelseyville, Calif., 1990)). Osteomalacia is the adult equivalent of rickets, and a key feature of tumour-acquired osteomalacia is softening of the bones. The softened bones become distorted, resulting in bow-legs and other associated changes reminiscent of familial rickets. Low serum phosphate, and abnormal vitamin D metabolism are also key features shared with HYP. Tumour acquired osteomalacia is rare, and the tumours are mainly of mesenchyrnal origin, although a number of different tumour types have also been reported (Rowe, Exp. Nephrol. 5 (1997), 355–363; Francis, Baillieres Clinical Endocrinology and metabolism 11 (1997), 145–163; loakimidis, The J. Rheumatology 21(6) (1994), 1162–1164; Lyles, Ann. Intem. Med. 93 (1980), 275–278; Rowe, Hum. Genet. 94 (1994), 457–467; Shane, Journal of Bone and Mineral Research 12 (1997), 1502–1511; Weidner, Cancer 59 (1987), 1442–1442). Surgical removal of the tumour(s) when possible, results in the disappearance of disease symptoms and bone healing, suggesting the role of a circulating phosphaturic factor(s) in the pathogenesis of the disease. Also, hetero-transplantation of tumours into nude mice (Miyauchi, J. Clin. Endocrinol. Metab. 67 (1988), 46–53) infusion of saline extracts into rats and dogs (Aschinberg, J. Paediatr. 91 (1977), 56–60; Popovtzer, Clin. Res. 29 (1981), 418A (Abstract)), and the use of tumour conditioned medium (TCM), of human and animal renal cell lines all confirm that a circulating phosphaturic factor is secreted by these tumours.

Although the primary-defect in X-linked rickets is confirmed as a mutated Zn metalloendopeptidase (PHEX), there is considerable evidence that implicates a circulating phosphaturic factor(s) (Ecarot, J. Bone Miner. Res. 7 (1992), 215–220; Ecarot, J. Bone Miner. Res. 10 (1995), 424–431; Morgan, Arch. Intern. Med. 134 (1974), 549–552; Nesbitt, J. Clin. Invest. 89 (1992), 1453–1459; Nesbitt, J. Bone. Miner. Res. 10 (1995), 1327–1333; Nesbitt, Endocrinology 137 (1996), 943–948; Qiu, Genet. Res., Camb. 62 (1993), 39–43; Lajeunesse, Kidney Int. 50 (1996), 1531–1538; Meyer, J. Bone. Miner. Res. 4(4) (1989), 523–532; Meyer, J. Bone. Miner. Res. 4 (1989), 493–500). The overlapping pathophysiology of HYP and OHO raises the intriguing possibility that the tumour-factor may be processed in normal subjects by the PHEX gene product. Also, it is likely that proteolytic processing by PHEX may act by either degrading this undefined phosphaturic factor(s), or by activating a phosphate-conserving cascade (Carpenter, Pediatric Clinics of North America 44 (1997), 443–466; Econs, Am. J. Physiol. 273 (1997), F489–F498; Glorieux, Arch. Pediatr. 4 (1997), 102s–105s; Grieff, Current Opinion in Nephrology & Hypertension 6 (1997), 15–19; Hanna, Current Therapy in Endocrinology & Metabolism 6 (1997), 533–540; Kumar, Nephrol. Dial. Transplant. 12 (1997), 11–13; Takeda, Ryoikibetsu Shokogun Shirizu (1997), 656–659). The cloning and characterization of the tumour-phosphaturic factor is thus prerequisite to establishing any links between tumour osteomalacia and familial X-linked rickets as well as other disorders in the phosphate metabolism.

Rowe et al (1996) have reported candidates 56 and 58 kDa protein (s) responsible for mediating renal defects in OHO (Rowe, Bone 18, (1996), 159–169). A patient with OHO was treated by tumor removal and pre- and post-operative antisera from the patient were used in a Western blotting identification of tumor conditioned media proteins. Neither the tumor cells nor the antisera were ever made available to the public, however.

In a review in Exp. Nephrol. 5 (1997), 335–363, Rowe (1997) discusses the above diseases and the role of the PHEX gene (previously known as the PEX gene). The PHEX gene product has been identified as a zinc metalloproteinase. In disease states such as familial rickets, defective PHEX results in uncleaved phosphatonin which would result in down regulation of the sodium dependent phosphate cotransporter and up regulation of renal mitochondrial 24-hydroxylase. However, no purification of phosphatonin was reported by Rowe (1997). Thus, no source material for phosphatonin was made available to the public. Moreover, purification, identification and characterization of phosphatonin has not been possible.

Thus, there is a need for polypeptides that regulate phosphate metabolism, since disturbances of such a regulation may be involved in hypo- and hyperphosphatemic diseases, including osteomalacia, particularly osteoporosis and renal failure. Furthermore, there is a need for identifying and characterizing such polypeptides which may play a role in the detection, prevention and/or correction of such disorders and may be useful in diagnosing those disorders.

SUMMARY OF THE INVENTION

The present invention relates to novel phosphatonin polypeptides and the encoding polynucleotides of phosphatonin. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The present invention further relates to screening methods for identifying binding partners of phosphatonin.

BRIEF DESCRIPTION OF THE DRAWINGS

FIG. 8: cDNA sequence (SEQ ID NO. 1) and amino acid sequence (SEQ ID NO: 2) of the largest MEPE clone isolated (PHO11.1). The five other clone isolated are encompassed by this larger clone and all clone are in frame with the cloning vehicle pBSCPT SK II-. Primers used for PCR are highlighted, and the total number of residues are 430 and 1655 bp respectively. The prokaryotic expression vector pCal-n-EK contained all in frame residues from MEPE residue V, to the MEPE stop codon (TAG), at 1291–93 bp. The single polyadenylation sequence AA{T/U}AAA is double underlined. The region of shared localized homology with DMA-1, DSSP, and OPN is underlined in wavy line format (MEPE-motif C-terminus), RGD residues are enclosed in an ellipsoid), glycosaminoglycan attachment site is boxed (complete line format), Tyrosine Kinase site is underlined once, and N-glycosylation motifs are boxed in dotted line format. For a complete list of motifs including casein kinase II, protein kinase C etc. please refer to prosite screen Table 1.

DETAILED DESCRIPTION OF THE PRESENT INVENTION

Figure 1A:
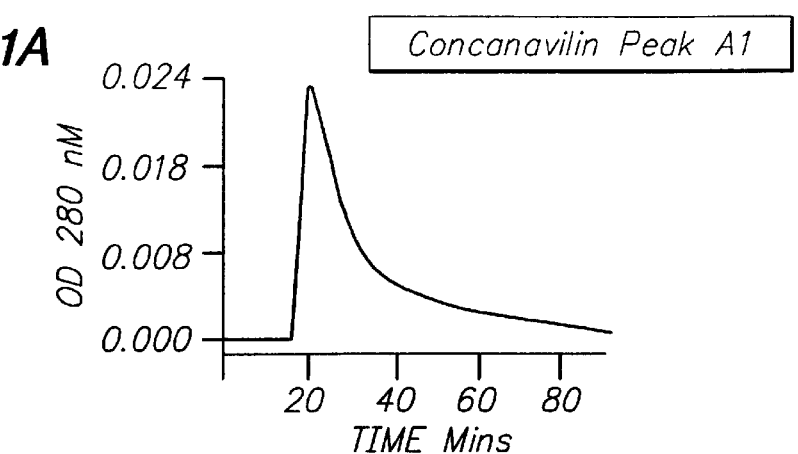
FIGS. 1(a) and (b) show respectively chromatograms with low affinity and high affinity protein-containing peaks from a concanavalin A column.

In view of the need of diagnostic and therapeutic means for the treatment of diseases related to disorders in the phosphate metabolism in the human body, the technical problem of the invention is to provide means and methods for the modulation of phosphate metabolism which are particularly useful for the treatment of bone mineral and renal diseases.

The above-defined technical problem is solved by the present invention by providing the embodiments characterized in the claims. Accordingly, in one aspect the present invention relates to an isolated polypeptide having phosphatonin activity.

Unless otherwise stated, the terms used herein are defined as described in "A multilingual glossary of biotechnological terms: (IUPAC Recommendations)", Leuenberger, H. G. W., Nagel, B. and K÷lbl, H. eds. (1995), Helvetica Chimica Acta, CH-4010 Basle, Switzerland, ISBN 3-906 390-13-6. The following definitions are provided to facilitate understanding of certain terms used throughout this specification.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease. The present invention is directed towards treating patients with medical conditions relating to a disorder of phosphate metabolism. Accordingly, a treatment of the invention would involve preventing, inhibiting or relieving any medical condition related to phosphate metabolism disorders.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

The phosphatonin polypeptide isolated in accordance with the present invention typically has an approximate molecular weight of 53 to 60 kDa, more preferably 58–60 kDa, as measured on SDS-PAGE, particularly on a 12.5% gel at pH 8.6 in TRIS-Glycine SDS buffer, see Example 1. An approximate molecular weight of 200 kDa may be measured on bis-tris-SDS-PAGE at pH 7 using a 4–12% gradient gel with MOPS running buffer. It is possible on such a gel also to see lower molecular weight bands of 53 to 60 kDa. The polypeptide is generally glycosylated, and preferably comprises phosphatonin in substantially pure form.

Surprisingly, it has been found that the phosphatonin is obtainable, following purification according to the protocol given in Example 1 from Saos-2 cells, which are available from the European Collection of Cell Culture under Deposit No. ECACC 89050205. Accordingly, in a further aspect of the invention, there is provided use of Saos-2 cells or HTB-96 cells for the production of phosphatonin. Other transformed or immortalized cell lines may be capable of overexpression of phosphatonin, such as transformed osteoblast or bone cell lines.

The present invention also describes the characterization and cloning of a gene that is a candidate for the above-described tumour-derived phosphaturic factor and that is named phosphatonin or MEPE (Metastatic-tumour Excreted Phosphaturic-Element). To summarize, expression screening of a λ ZAPII-cDNA library constructed from mRNA extracted from an OHO tumour using antisera specific to tumor conditioned media (TCM) phosphaturic-factor was used. The protein is glycosylated and resolves as two bands on SDS-PAGE electrophoresis (58–60 kDa), with evidence of possible splicing or post translational cleavage. The first cloned cDNA codes for a protein of 430 residues (SEQ ID NO: 2) and 1655 bp in length (SEQ ID NO: 1). The entire 3' end of the gene is present, with part of the 5' end missing. Secondary structure prediction confirms that the protein is highly hydrophilic with small localized regions of hydrophobicity and no cysteine residues. A number of helical regions are present, with two distinct N-glycosylation motifs at the carboxy-terminus. A key feature is the presence of a cell attachment sequence in the same structural context found in osteopontin. Proteolytic-sites adjacent to this motif may result in altered receptor specificity for specific integrins as found in osteopontin. Screening of the trembl database with MEPE sequence also demonstrated sequence homology with Dentin phosphoryn (DPP). In particular there is striking localized residue homology at the C'-terminus of MEPE with DPP, dentin-matrix protein-1 (DMA-1) and osteopontin (OPN). This region of MEPE contains a recurring series of Aspartate and serine residues (SEQ ID NO: 11, i.e. DDSSESSDSGSSSESD) with 80%, 65% and 62% homology with DSP, DMA-1 and OPN respectively. Moreover, when residue physicochemical character is considered this homology rises to 93%, suggesting a shared or related biological-functionality. It is also of note that this structural motif overlaps a casein kinase II phosphorylation motif in MEPE. Skeletal casein kinase II activity is defective in rickets, and results in under phosphorylation of osteopontin (Rifas, Calcif. Tissue Int. 61 (1997), 256–259). The casein kinase II defect has thus been proposed to play a role in the under-mineralization of bone matrix (Rifas, loc. cit.).

Dentin phosphoryn (DPP), is one part of a cleavage product derived from dentin sialophosphoprotein (DSSP), with the other part known as dentin sialoprotein (DSP) (MacDougall, J. Biol. Chem. 272 (1997), 835–842). It is of particular interest that DSSP, DMA-1, OPN and MEPE are RGD containing phospho-glycoproteins with distinct structural similarities and major roles in bone-tooth mineralization (Linde, Crit. Rev. Oral Biol. Med. 4 (1993), 679–728).

The new OHO tumour-derived phosphaturic factor named phosphatonin or MEPE described in the present invention, effects bone mineral homeostasis by regulating Na+ dependent phosphate co-transport, vitamin D metabolism, and bone mineralization.

As set out in further detail below, a polynucleotide has been isolated which encodes polypeptides according to the present invention; see Example 2. The nucleotide and amino acid sequences of phosphatonin are set out in FIG. 8 (SEQ ID NO: 1 and SEQ ID NO: 2, respectively). In the continuous research efforts on phosphatonin, a further polynucleotide has been isolated which encodes the N-terminus of the phosphatonin polypeptide; see Example 13. The nucleotide and amino acid sequences of the full-length phosphatonin protein are set out in SEQ ID NO: 26 and SEQ ID NO: 27, respectively. The amino acid sequence described in SEQ ID NO: 27 differs from the one shown in FIG. 8 by an additional 95 amino acid residues and a correction of the first valine to leucine on the N-terminus end of the amino acid sequence set out in FIG. 8 (SEQ ID NO: 2) (total length 525 vs. previous 430), and the N-terminus contains a signal peptide of about 17 amino acid residues preceded by a consensus methionine start codon. Primer extension and Northern blot analysis confirm that the nucleotide sequence shown in SEQ ID NO: 26 is 4 to 6 nucleotides short of the complete cDNA. Also the corresponding extended N-terminal sequence contains two cysteines (the only cysteines found in the entire phosphatonin molecule). One of the cysteines, at position 31 of SEQ ID NO: 27, is optimally placed for the formation of homodimers or heterodimers and the other is five residues downstream from the methionine start codon (at the edge of the signal peptide). This indicates that after cleavage of signal peptide and release of phosphatonin into the extracellular milieu the N-terminus may be involved in covalent protein—protein interactions. The truncated form of Rec-MEPE used in the experiments described in Example 12 lacks this portion of the molecule (95 residues missing including signal peptide and the residue on the N-terminus end was valine instead of leucine) and, thus, is incapable of forming covalent cysteine—cysteine inter-protein bridges. Moreover, the region upstream of the truncated rec-MEPE protein contains a proteolytic cleavage site that is a candidate for cleavage by PHEX, NEP and Nardilysin. The PHEX, NEP proteolytic site is at residue 46 of SEQ ID NO: 27 (KDNIG(FHHLG) and would result in removal of a portion of the N-terminus containing the cysteine. It should be emphasized that these proteolytic-sites are highly conserved and occur infrequently. The remaining molecule (missing cleaved N-terminus) is, thus, similar to the truncated form of rec-MEPE. The implication is that the rec-MEPE used in Example 12 cannot form dimers resulting in phosphate-retaining properties. Tumor derived MEPE is thus predicted to form dimers and interfere with renal-phosphate handling resulting in inhibition of phosphate uptake.

In accordance with this additional data, obtained in accordance with the present invention, shows that 24-hydroxylase expression (an enzyme involved in the catabolism of 1.25 (OH)2 vitamin D3, and up-regulated in X-linked rickets (Hyp)), is suppressed in a human renal cell-line exposed to rec-MEPE. Thus, both phosphate uptake and vitamin D metabolism expression are consistent with the above interpretation. Accordingly, the polypeptide of the present invention comprises the amino acid sequence of SEQ ID NO: 27, optionally including mutations or deletions which do not substantially affect the activity thereof. Such mutations include substitution of one or more amino acids, particularly by homologues thereof, as well as additions of one or more amino acids, especially at the N or C termini. For example, a polymorphism at amino acid residue 106 in the amino acid sequence of SEQ ID NO: 27 has been found where the glutamate can also be glycine. There appears to be an equal distribution in the clones thus far analyzed. Deletions include deletions from the N or C termini. Substitutions by both naturally-occurring and synthetic amino acids are possible. Also included are polypeptides modified by chemical modification or enzymatic modification. Further, fragment peptides, whether chemically synthesized or produced by a biological method, whether modified or unmodified, are included within the scope of this invention.

Accordingly the present invention relates to a phosphatonin polypeptide or an immunologically and/or biologically active fragment thereof, which comprises an amino acid sequence encodable by a polynucleotide selected from the group consisting of (a) polynucleotides encoding at least the mature form of the polypeptide comprising the amino acid sequence depicted in SEQ ID NO: 2 (FIG. 8) or SEQ ID NO: 27;

(b) polynucleotides comprising the coding sequence as depicted in SEQ ID NO: 1 (FIG. 8) or SEQ ID NO: 26 encoding at least the mature form of the polypeptide;

(c) polynucleotides comprising at least a nucleotide sequence encoding amino acid residues 1 to 46, 1 to 96, 18 to 46, 18 to 96, 47 to 96, 47 to 525, and 18 to 525 of SEQ ID NO: 27;

(d) polynucleotides encoding a polypeptide derived from the polypeptide encoded by a polynucleotide of (a), (b) or (c) by way of substitution, deletion and/or addition of one or several amino acids of the amino acid sequence encoded by the polynucleotide of (a), (b) or (c);

(e) polynucleotides comprising the complementary strand which hybridizes with a polynucleotide of any one of (a) to (d);

(f) polynucleotides encoding a polypeptide the sequence of which has an identity of 60% or more to the amino acid sequence of the polypeptide encoded by a polynucleotide of any one of (a) to (e);

(g) polynucleotides encoding a polypeptide capable of regulating phosphate metabolism comprising a fragment or an epitope-bearing portion of a polypeptide encoded by a polynucleotide of any one of (a) to (f);

(h) polynucleotides encoding an epitope-bearing portion of a phosphatonin polypeptide comprising amino acid residues from about 1 to 40, 141 to 180 and/or 401 to 429 in SEQ ID NO: 2 (FIG. 8) and/or amino acid residues from about 18 to 46 and/or 47 to 96 of SEQ ID NO: 27;

(i) polynucleotides comprising at least 15 nucleotides of a polynucleotide of any one of (a) to (h) and encoding a polypeptide capable of regulating phosphate metabolism;

(j) polynucleotides encoding a polypeptide capable of regulating phosphate metabolism comprising the cell and/or glycosaminoglycan attachment motif and/or the bone mineral motif of a polypeptide encoded by a polynucleotide of any one of (a) to (i);

(k) polynucleotides of any one of (a) to (j) wherein the encoded polypeptide is capable of forming a homo- and/or heterodimer; and (l) polynucleotides the nucleotide sequence of which is degenerate as a result of the genetic code to a nucleotide sequence of a polynucleotide of any of (a) to (k).

As used herein, a phosphatonin "polynucleotide" refers to a molecule having a nucleic acid sequence contained in SEQ ID NO: 1 or 26 or encoding the phosphatonin polypeptide of the present invention. For example, the phosphatonin polynucleotide can contain the nucleotide sequence of the full length cDNA sequence, including the 5' and 3' untranslated sequences, the coding region, as well as fragments, epitopes, domains, and variants of the nucleic acid sequence. Moreover, as used herein, a phosphatonin "polypeptide" refers to a molecule having the translated amino acid sequence generated from the polynucleotide as broadly defined.

A phosphatonin "polynucleotide" also includes those polynucleotides capable of hybridizing, under stringent hybridization conditions, to sequences contained in SEQ ID NO: 1 or 26 or the complement thereof. "Stringent hybridization conditions" refers to an overnight incubation at 42 C in a solution comprising 50% formamide, 5× SSC (750 mM NaCl, 75 mM sodium citrate), 50 mM sodium phosphate (pH 7.6), 5×Denhardt's solution, 10% dextran sulfate, and 20=g/ml denatured, sheared salmon sperm DNA, followed by washing the filters in 0.1× SSC at about 65 C. Further suitable hybridization conditions are described in the examples.

Also contemplated are nucleic acid molecules that hybridize to the phosphatonin polynucleotides at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 C in a solution comprising 6×SSPE (20×SSPE=3M NaCl; 0.2M NaH2PO4; 0.02M EDTA, pH 7.4), 0.5% SDS, 30% formamide, 100 (g/ml salmon sperm blocking DNA; followed by washes at 50 C with 1×SSPE, 0.1% SDS. In addition, to achieve even lower stringency, washes performed following stringent hybridization can be done at higher salt concentrations (e.g. 5× SSC). Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Of course, a polynucleotide which hybridizes only to polyA+sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

The phosphatonin polynucleotide can be composed of any polyribonucleotide or polydeoxribonucleotide, which may be unmodified RNA or DNA or modified RNA or DNA. For example, phosphatonin polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the phosphatonin polynucleotides can be composed of triple-stranded regions comprising RNA or DNA or both RNA and DNA. Phosphatonin polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

Phosphatonin polypeptides can be composed of amino acids joined to each other by peptide bonds or modified peptide bonds, i.e., peptide isosteres, and may contain amino acids other than the 20 gene-encoded amino acids. The phosphatonin polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the phosphatonin polypeptide, including the peptide backbone, the amino acid side-chains and the amino or carboxyl termini. It will be appreciated that the same type of modification may be present in the same or varying degrees at several sites in a given phosphatonin polypeptide. Also, a given phosphatonin polypeptide may contain many types of modifications. Phosphatonin polypeptides may be branched, for example, as a result of ubiquitination, and they may be cyclic, with or without branching. Cyclic, branched, and branched cyclic phosphatonin polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivatives covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pages. 1–12; Seifter, Meth. Enzymol. 182 (1990); 626–646, Rattan, Ann. NY Acad. Sci. 663 (1992); 48–62. For example, it is possible that phosphatonin is expressed as a preproprotein and after processing of the pre-sequence and optionally pro-sequence is cleaved into two or more fragments which remain together due to the formation of, for example, hydrogen bonds and/or disulfide bridges. The processing and/or cleavage of the prepro- and even mature form of the phosphatonin polypeptide may be accompanied by the loss of one or more amino acids at the cleavage site. It is to be understood that all such forms of the phosphatonin protein are encompassed by the term "phosphatonin polypeptide", "polypeptide" or "protein".

"SEQ ID NO: 1" and "SEQ ID NO: 26" refer to a phosphatonin polynucleotide sequence while "SEQ ID NO: 2" and "SEQ ID NO: 27" refer to a phosphatonin polypeptide sequence.

A phosphatonin polypeptide "having biological activity" refers to polypeptides exhibiting activity similar, but not necessarily identical to, an activity of a phosphatonin polypeptide as measured in a particular biological assay such as described below, with or without dose dependency. In the case where dose dependency does exist, it need not be identical to that of the phosphatonin polypeptide, but rather substantially similar to the dose-dependence in a given activity as compared to the phosphatonin polypeptide (i.e., the candidate polypeptide will exhibit greater activity or not more than about 25-fold less and, preferably, not more than about ten-fold less activity, and most preferably, not more than about three-fold less activity relative to the phosphatonin polypeptide).

The term "immunologically active" or "immunological activity" refers to fragments, analogues and derivatives of the phosphatonin polypeptide of the invention the essential characteristic immunological properties of which remain unaffected in kind, that is that the polynucleotides of the invention include all nucleotide sequences encoding proteins or peptides which have at least a part of the primary and/or secondary structural conformation for one or more epitopes capable of reacting specifically with antibodies unique to phosphatonin proteins which are encodable by a polynucleotide as set forth above. Preferably, the peptides and proteins encoded by a polynucleotide of the invention are recognized by an antibody that specifically reacts with an epitope of the phosphatonin polypeptide comprising the amino acid residues of about 20 to 30, 100 to 130, 145 to 160, 300 to 310, 320 to 340 or 380 to 430 of SEQ ID NO: 2 or with an epitope of the phosphatonin polypeptides described herein below. Residues 380–430 peptides/antibodies are particularly useful for the study of mineralization processes, residues 145–160 peptides/antibodies for the study of receptor ligand interactions (inter gins etc.) and residues 20–30 and 100–130, are of particular interest for phosphate regulations studies. Further preferred epitopes that are present in the phosphatonin polypeptide of the present invention comprise amino acid residues 1 to 46, 1 to 96, 18–46, 18 to 96, 47–96, 47 to 525, and/or 18–525 of SEQ ID NO: 27. In a particular preferred embodiment, the phosphatonin peptide of the present invention comprises the amino acid sequence from amino acid position 18 to 46, 47 to 525 of SEQ ID NO: 27.

Preferably, the immunologically active phosphatonin peptide fragments, analogues and derivatives of the phosphatonin polypeptide of the invention are capable of eliciting an immune response in a mammal, preferably in mouse or rat.

In a preferred embodiment of the present invention the phosphatonin polypeptide is biologically active in that it is capable of regulating or modulating phosphate metabolism, preferably it has "phosphatonin activity".

Phosphatonin Activity

The term "capable of regulating or modulating phosphate metabolism" as used herein means that the presence or absence, i.e. the level of the phosphatonin polypeptide of the invention in a subject modulates Na+-dependent phosphate co-transport, vitamin D metabolism and/or bone mineralization. Depending on whether the mentioned activities are up- or down-regulated by the polypeptide of the invention, said "capability of regulating or modulating phosphate metabolism" is referred to as "phosphatonin activity" and "anti-phosphatonin activity", respectively.

Phosphatonin activity may be measured by routine assay, particularly as the ability to down-regulate sodium dependent phosphate co-transport and/or up-regulate renal 25-hydroxy vitamin D3–24-hydroxylase and/or down-regulate renal 25-hydroxy-D-1 (-hydroxylase. In each case, regulation of the relevant enzyme activity may be effected directly or indirectly by the phosphatonin; e.g., by measurement of radioactive Na-dependent uptake of phosphate. These activities may be assayed using a suitable renal cell line such as CL8 or OK (deposited at the European Collection of Cell Cultures under ECACC 91021202). A suitable assay methodology is found in Rowe et al (1996). Phosphatonin activity may further be measured by the ability to promote osteoblast-mediated mineralization in tissue culture; see, e.g., Santibanez, Br. J Cancer 74 (1996), 418–422; Stringa, Bone 16 (1995), 663–670; Aronow, J. Cell Physiol. 143 (1990), 213–221; or as described in the appended examples.

In a further aspect, the present invention provides a polypeptide comprising a bioactive fragment of the polypeptide described above. Without intending to be bound by theory, it is thought that phosphatonin may function as a polyhormone which may be cleaved in vivo to form one or more fragments at least some of which possess biological activity such as hormonal activity. In vivo it is thought that phosphatonin may be cleaved proteolytically, for example by the PHEX gene product to produce at least one functional fragment. In a preferred embodiment, the polypeptide comprising the bioactive fragment is capable of regulating phosphate metabolism, for example by possessing phosphatonin activity as discussed above, or by possessing the opposite of phosphatonin activity as discussed in further detail below. The bioactive fragment may be an N-terminal, C-terminal or internal fragment. The polypeptide comprising the bioactive fragment may further comprise additionally amino acid sequence provided that the activity of the bioactive fragment is not substantially affected.

Figure 15:
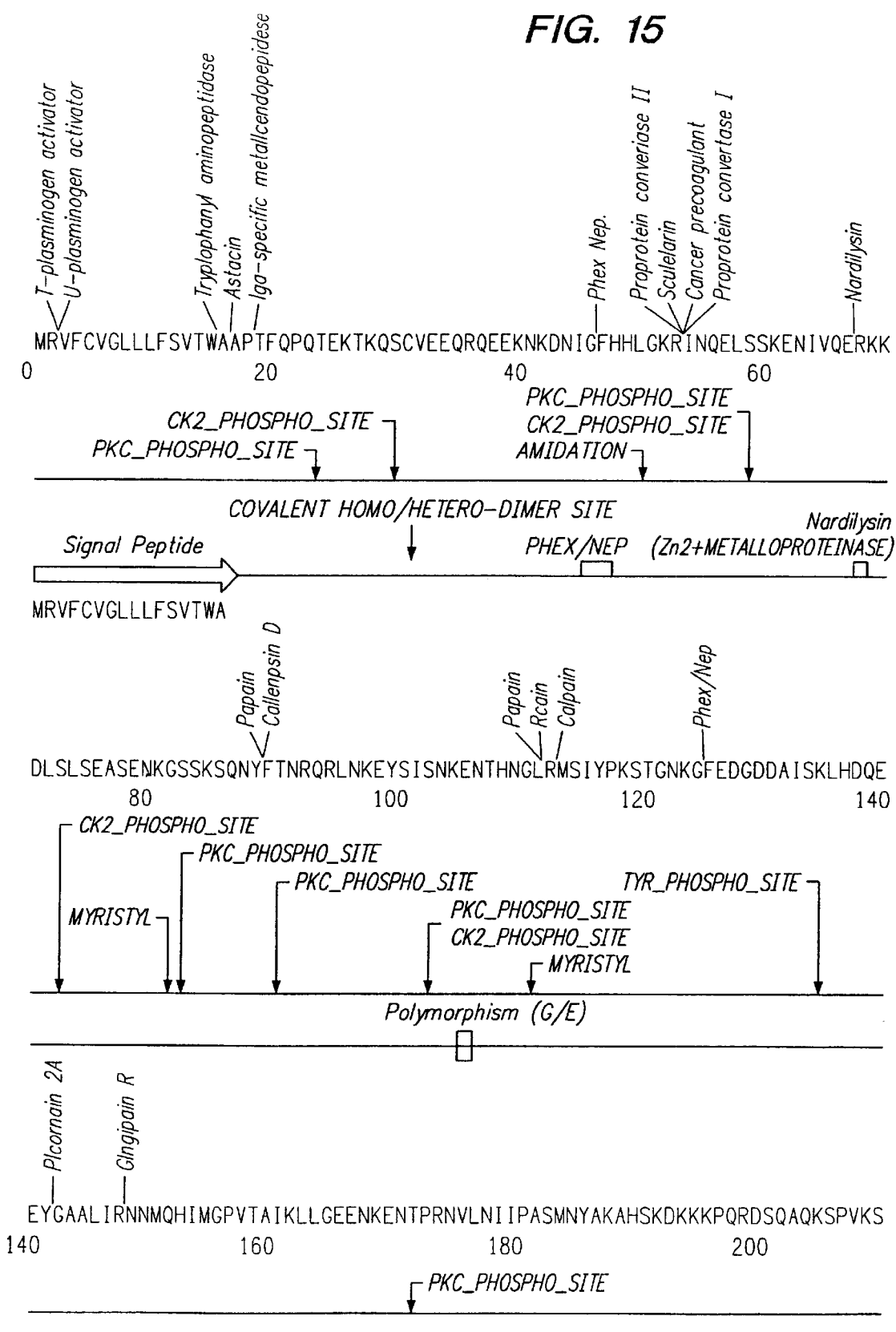
FIG. 15: Primary structure of the entire phosphatonin molecule. Structural and functional motifs in the amino acid sequence (SEQ ID NO: 27) of phosphatonin are indicated. For further explanations see text and legend to FIG. 8 and Table 1.
Figure 15:
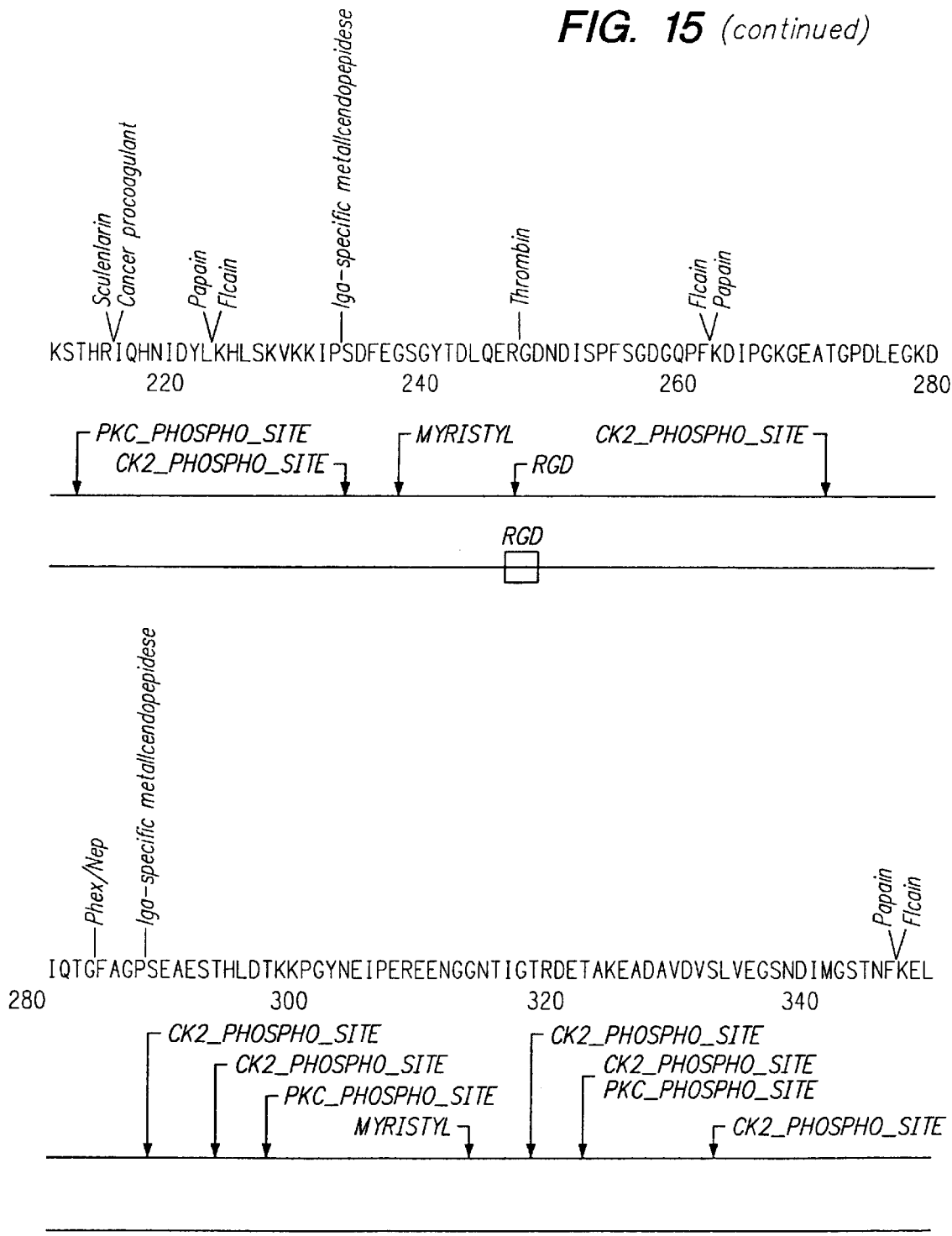
Figure 15:
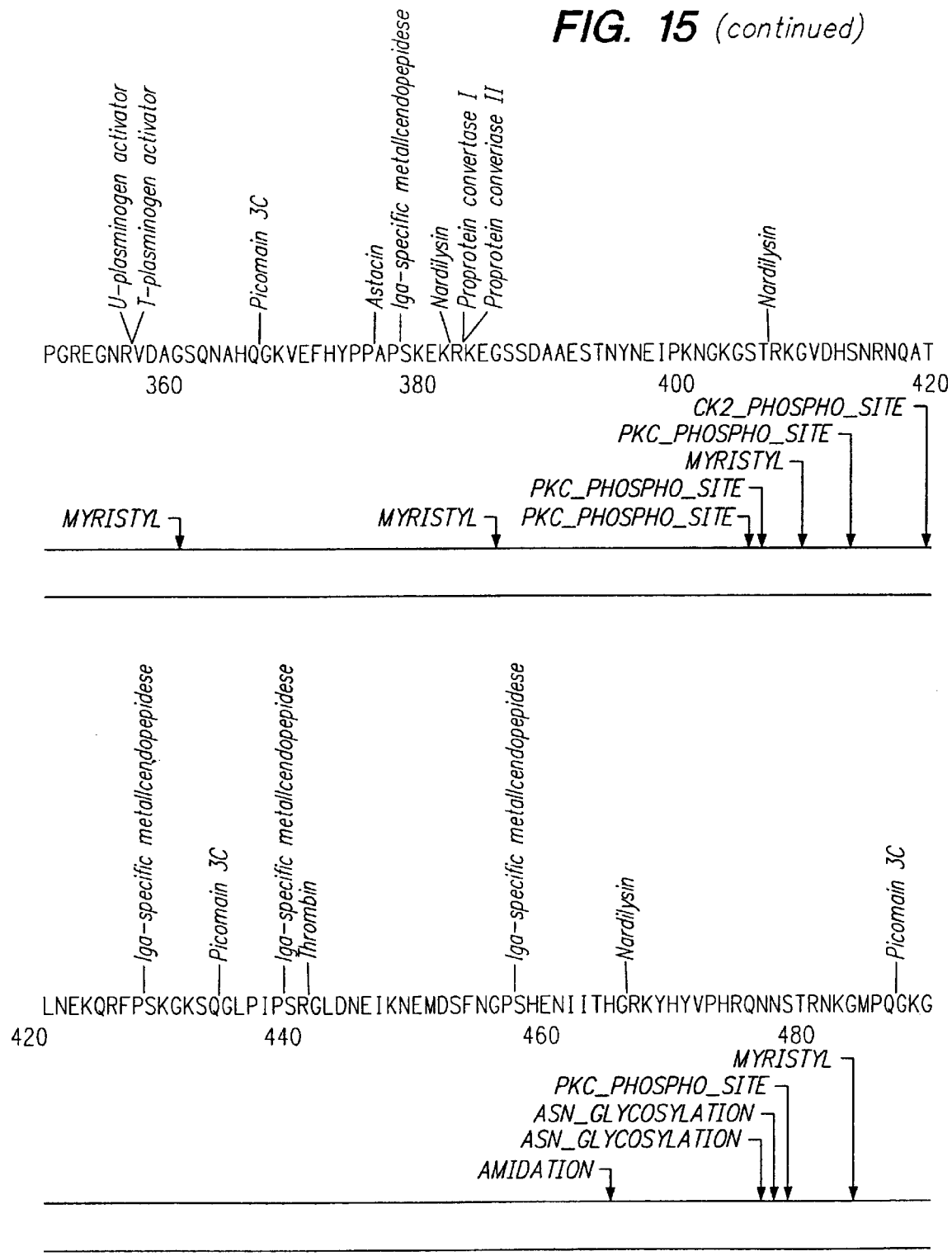
Figure 15:
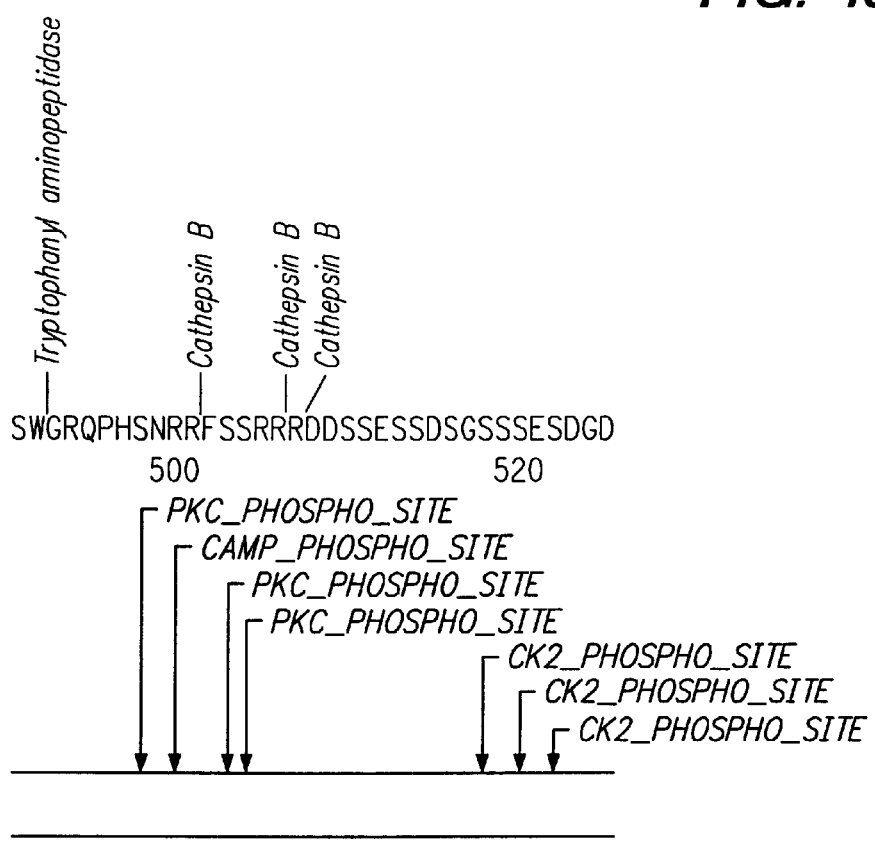

Advantageously, the bioactive fragment has a cell attachment motif which preferably comprises RGD. As discussed in further detail below, this motif may be involved in receptor and/or bone mineral matrix interaction. Advantageously, the bioactive fragment has a glycosaminoglycan attachment motif, which preferably comprises SGDG (SEQ ID NO: 3). Attachment of glycosaminoglycan is thought to permit the fragment to resemble a proteoglycan. Proteoglycans are known to be involved in bone bioactivity, particularly in cell signaling. These motifs are discussed in greater detail below. The primary structure of the entire phosphatonin molecule including structural and functional motifs is shown in FIG. 15. Any bioactive and/or immunologically active fragment of phosphatonin can be generated therefrom by recombinant DNA technology and/or (bio)chemical means, for example subjecting the phosphatonin molecule or derivatives thereof to enzymes such as endopeptidase and phosphatase in vitro or in vivo.

In one embodiment of the present invention, the polypeptide comprising the bioactive fragment possesses phosphatonin activity: Without intending to be bound by theory, such activity is expected in phosphatonin uncleaved by PHEX metalloproteinase and some bioactive fragments carrying a PHEX metalloproteinase cleavage site such as the site ADAVDVS (SEQ ID NO: 4) where cleavage is proposed to occur between residues VD (residues 235 and 236 in the amino acid sequence of FIG. 8 corresponding to position 330 and 331 of SEQ ID NO: 27) and/or between residues GF at position 46 and 47 in the amino acid sequence of SEQ ID NO:. 27. The bioactive fragment may comprise at least the first 236 residues of the amino acid sequence of FIG. 8 so that this PHEX metalloproteinase cleavage site is part of the fragment. Such polypeptides and fragments thereof having phosphatonin activity will be useful in treating hyperphosphatemic conditions.

It is to be understood that with regards to PHEX specificity in accordance with the present invention preferably a tighter definition is used that includes glycine and phenylalanine (GF) as conserved and good candidate sites for cleavage. In this regard there are only three such sites in the entire phosphatonin molecule at amino acid residue-positions (46, 125, and 283 in SEQ ID NO: 27); see also FIG. 15.

Also the bioactive fragment(s) may include the entire molecule downstream from the first PHEX site comprising of 479 residues of SEQ ID NO: 27 and the uncleaved molecule minus the putative signal peptide 508 residues (particularly with regards to phosphate uptake). In this regard it is proposed that the cysteine (residue 31), N-terminal to the original truncated rec-MEPE is prerequisite for the formation of Phosphatonin homodimers and/or heterodimers.

Again, without intending to be bound by theory it is believed that uncleaved dimerised phosphatonin is associated with phoshatonin activity (renal phosphate leak, phosphaturia, down-regulation of Na+ dependent phosphate co-transporters, and increase in 24-hydroxylase activity, hypophosphataemia etc.). Undimerised N-terminal cleaved phosphatonin is proposed to be associated with anti-phosphatonin activity, (increase in renal phosphate uptake, up-regulation of Na+ dependent phosphate co-transporters, and suppression of 24-hydroxylase, hyperphosphataemic and increase in 1-a-hydroxylase activity etc.).

With regard to bone mineralisation, it is surmised that the C-terminal region containing the MEPE-motif (probably after phosphorylation) interacts with the bone matrix (hydroxyapatite, collagen type I, fibronectin, osteocalcin), and the RGD motif interacts with cells via integrin receptors (osteoblasts and/or osteoclasts). The matrix cell interaction may play a key role in the nuclear-mineralsation and phosphatonin may also have an autocrine or paracrine effect on osteoblasts/osteoclasts gene-regulation and renal endocrine function.

Another possible scenario is the cleavage of phosphatonin into defined segments that each has specific bioactivity (as occurs with a number of hormones and bone morphogenic proteins). Moreover, post-translational modification via phosphorylation may also play a key role in modulating phosphatonin bioactivity. For example, a fragment (158 residues) encompassing the RGD motif could theoretically be generated by PHEX cleavage in the phosphatonin molecule at residues 125 and 283 of SEQ ID NO: 27 and this may have defined bioactivity. An N-terminal fragment generated by cleavage at residues 46 and 125 (79 residues) in SEQ ID NO: 27 may also play a role in phosphate homeostasis, and the possibility of a C-terminal fragment of 242 residues generated by cleavage at residue 283 in the amino acid sequence of SEQ ID NO: 27 playing a role in bone-mineralisation is envisaged as well.

From the above observations and facts it is reasonable to propose that pro-phosphatonin on conversion to phosphatonin (signal peptide cleavage) is cleaved by PHEX or other endopeptidases resulting in a loss of the cysteine-containing N-terminal peptide. Homodimers or heterodimers of the remaining C-terminal protein would thus not be possible (no other cysteines in the entire phosphatonin-molecule). Formation of phosphatonin dimers may result in defective renal phosphate handling by blocking renal NPT2 receptors (competing with processed phosphatonin), down-regulating NPT2 expression, affecting NPT2 mRNA stability, or altering intravesicular mobilisation of Na+ dependent phosphate co-transporters (either directly or indirectly). Removal of the N-terminal cysteine-containing region by PHEX or other endopeptidases would result in a truncated or processed form of the molecule with phosphate retaining activity. The recombinant fusion-protein used in the experiments of Example 12 lacks the N-terminal "cysteine-containing" region (N-terminal 95 residues of SEQ ID NO: 27 are missing and the leucine residue next to such 95 residues was valine) and may therefore act by imitating the phosphate-conserving or processed-form of MEPE (PHEX or metalloendopeptidase cleaved). Relevant to the presence of a unique zinc endopeptidase cleavage site in the N-terminal MEPE region for PHEX/NEP and the proposed dimerisation model, is the presence of a single site for proprotein convertases I and II. The regulation of bone morphogenetic protein (BMP) activity and a number of other hormones activities (pro-melanin, profibrillin, prothyrotropin-releasing hormone) by proprotein-convertases (PACE4 etc.) via endoproteolytic-cleavage of inactive precursor proteins has been demonstrated (Constam, J. Cell Biol. 144 (1999), 139–149; Raghunath, J. Cell Sci. 112 (1999), 1093–1100; Viale, J. Biol. Chem. 274 (1999), 6536–6545; Schaner, J. Biol. Chem. 272A (1997), 19958–19968). Also, the expression pattern of specific pro-convertases during embryogenesis are dynamic and colocalisation with BMP's occurs (Tsuji, J. Biochem. 126 (1999), 591–603).

In summary, it is believed that MEPE or phosphatonin is sequentially processed by proteolytic cleavage and optionally phosphorylation to generate a number of bioactive peptides. Removal of the first 46 residues appears to alter phosphatonin activity to anti-phosphatonin activity (phosphatonin defined as hypophosphataemic and anti-phosphatonin as hyperphosphataemic). PHEX is likely to play a key role in this process but the possibility of the involvement of other proteases is not excluded. For example the proprotein convertases have two possible cleavage sites at residues 54 and 383 in the amino acid sequence of SEQ ID NO: 27 and could generate a much larger RGD containing peptide (329 residues). There may also be alternative splicing and there is some evidence that suggests that the phosphatonin transcript in bone-marrow is of a different size to that found in the OHO-tumours.

Related Proteins

Figure 12A:
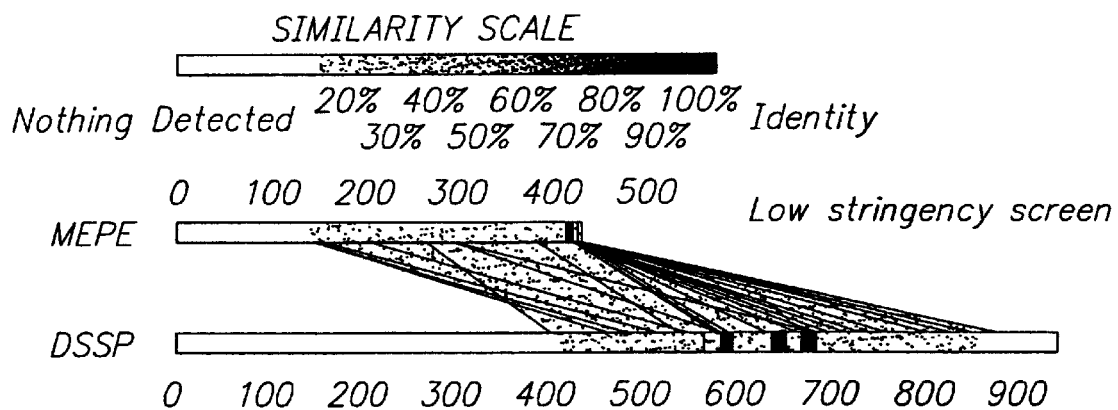
FIG. 12: Sequence similarity analysis using "sim" and lalnjview mathematical and software tools (Duret, Comput. Appl. Biosci. 12 (1996), 507–510) or MEPE and DSSP (dentin sialophosphoprotein). In each computation the gap between open penalty was set to 12, and the gap extension penalty was 4. Comparison matrix for B was PAM40 and BLOSUM 62 for A, C and D (see Duret, Comput. Appl. Biosci. 12 (1996), 507–510; Huang, Comput. Appl. Biosci. 8 (1992), 155–165; Huang, Co put. Appl. Biosci. (1990) 6,373–381). The similarity score threshold was 40% in, C and D and 70% in B. The highlighted blocks shown on each protein scheme represent sequence homologies of >62% in A, C and D and >80% in B. Note that in MEPE versus DSSP (B) there are five homology blocks in DSSP of >80% sequence similarity to a single motif in MEPE (SEQ ID. NO.: 7, i.e. DSSESSDSGSSSES). A similar sequence homology is also apparent for DMA1 (dentin matrix protein-1) and osteopontin (OPN) versus MEPE. The sequence block is designated an ASARM motif (Acidic Serine-Aspartate-Rich MEPE Associated Motif).
Figure 12B:
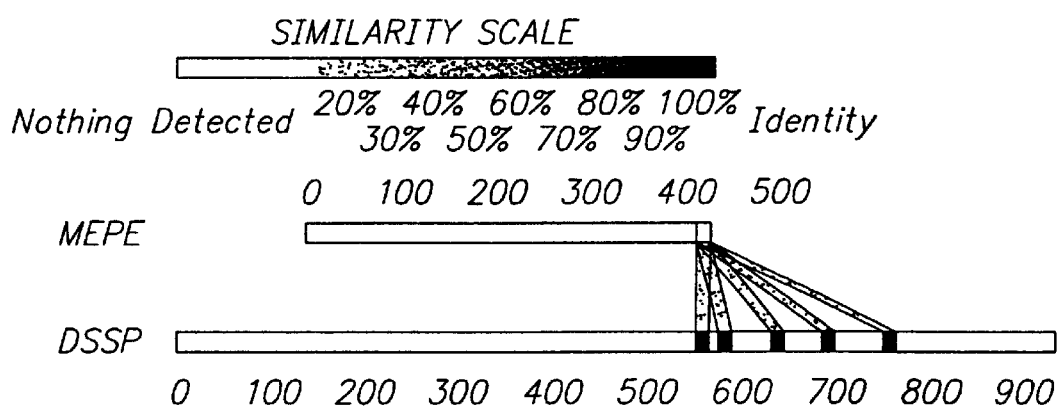
Figure 12C:
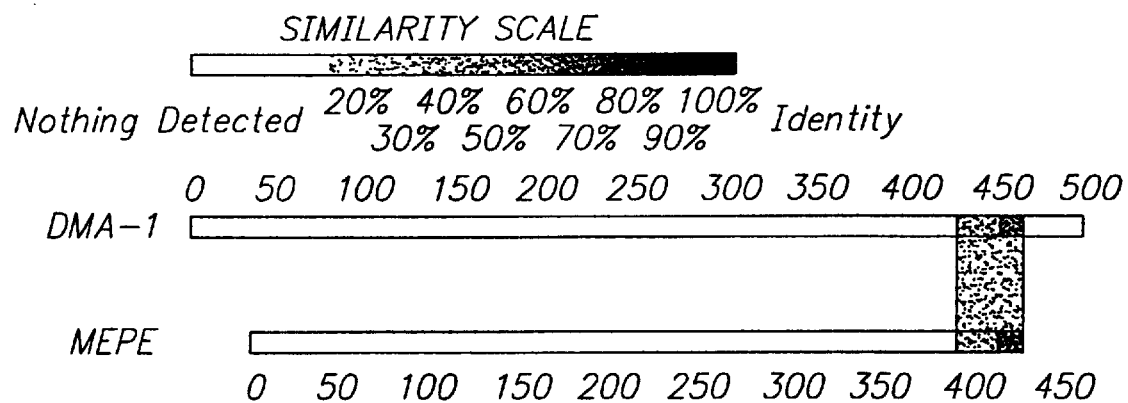
Figure 12D:
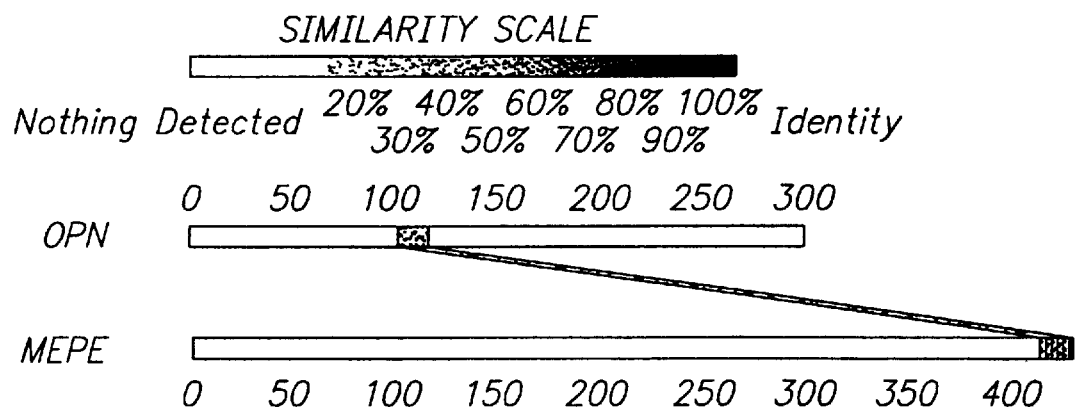

Further studies carried out in accordance with the present invention revealed a number of distinct similarities between phosphatonin (MEPE), dentin matrix protein-1 (DMP1), dentin sialo phosphoprotein (DSSP; more specifically the dentin phosphoryn C-terminus), bone sialoprotein (BSP) and osteopontin (OPN). In particular all the aforementioned matrix proteins have RGD motifs, are glycosylated with unusually high aspartate and serine contents. Casein kinase II phosphorylation motifs are a common feature and there are localized regions of homology shared between each of the proteins. Lanview-sim analyses Swissprot software (Duret, LALNVIEW: a graphical viewer for pairwise sequence alignments. Comput. Biosci. 12 (1996), 507–510) graphically illustrate the regions of high homology as dot matrix comparisons between phosphatonin and DSSP. The motif is repeated five times in the dentin phosphoryn (DP) portion of DSSP (FIG. 12a), and this motif has 80% homology to a C-terninal residue in phosphatonin. Based on physiochemical parameters a 93% homology can be deduced and this sequence homologue is present in the other bone/dentin molecules described with 60% to 65% sequence similarity. There is also in the same region extended sequence homology with a run of residues between DMA-1 and phosphatonin as is shown in Table 2 and in the sequence comparison below:

```
408 SSRRRDDSSESSDSGSSSESDG    429 MEPE    (SEQ ID NO:5)

443 SSRSKEDSN-STESKSSSEEDG    463 DMA-1   (SEQ ID NO:6)
```

Figure 13A:
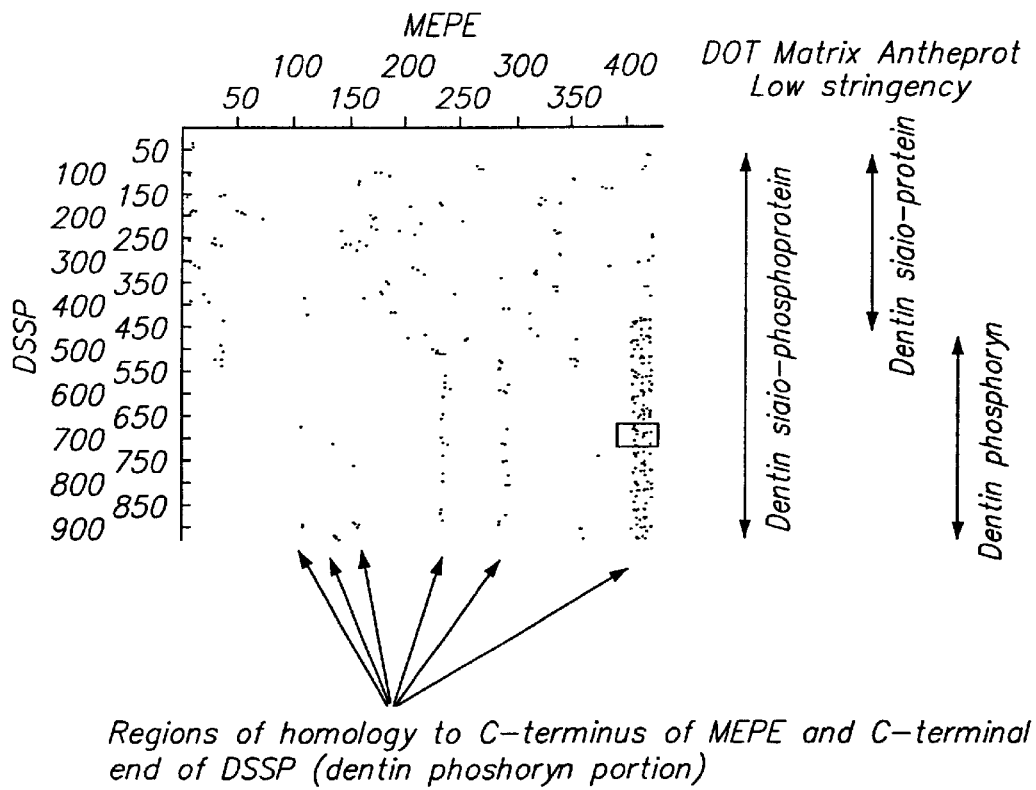
FIG. 13: Dot matrix comparison of DSSP versus MEPE using Antheprot statistical analysis (Deleague, G. Software for protein analysis: Antheroplot V2.5e. Microsoft group. (7 Passage du Vercours 69–367 Vercors Lyon Cedex 07, 1997)). In (A) a lower stringency comparison with a window set to 13 is used as screen parameters and in (B) a wider window of 15 is used. The colors indicate unity matrix scores as indicated on the diagram. C-terminal residues of MEPE-motif have >80% sequence homology and the repeat nature of the motif is illustrated by the striped pattern.
Figure 13B:
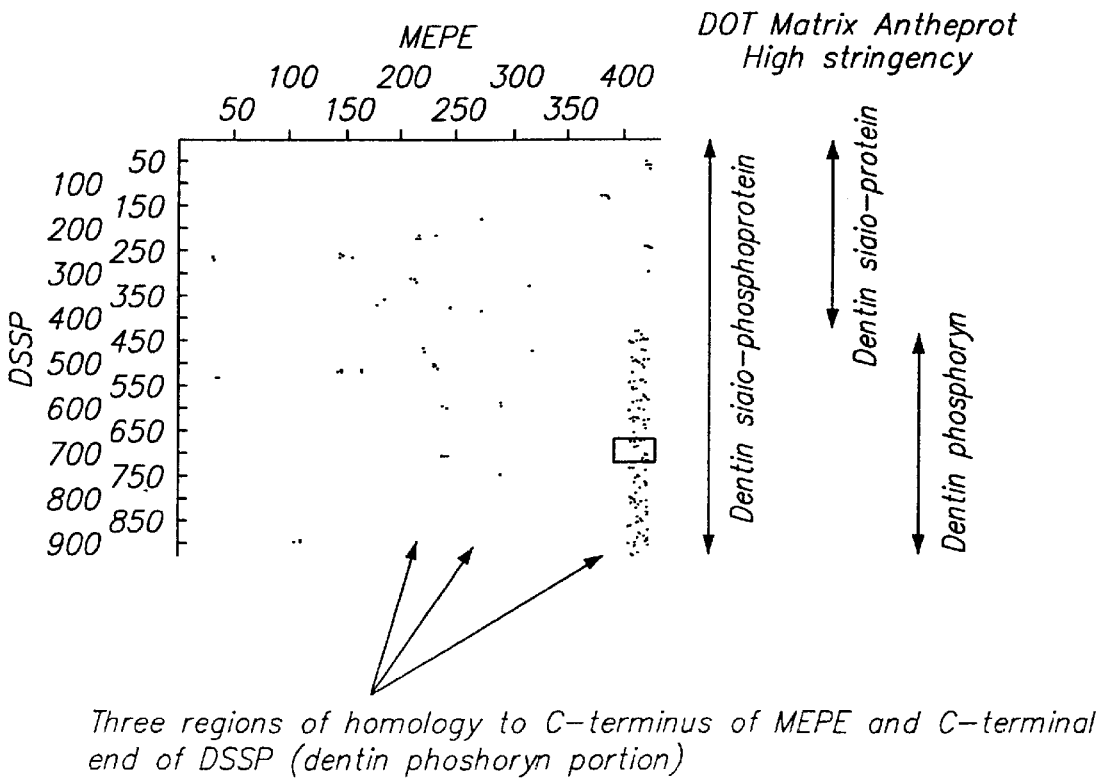

Dentin sialo-phosphoprotein (DSSP) is a large RGD-containing glycoprotein that in-vivo is cleaved to generate two proteins known as dentin sialoprotein (DSP) and dentin phosphoryn (DP), respectively (MacDougall, J. Biol. Chem. 272 (1997), 853–842). DSP is the N-terminal peptide and DP the C-terninal and both were originally thought to be derivatives of different genes. A statistical dot-matrix comparison of phosphatonin versus DSSP at high and low stringency comparison is shown in FIG. 13. The repeat nature of the "motif-homologue" (DSSESSDSGSSSES (SEQ ID NO: 7)) in DSSP and its striking homology is clearly displayed in both graphical presentations. The motif is present only once in MEPE at the C-terminus. Moreover, overall low level sequence-similarity to the C-terminal portion of DSSP (or the DP component) is clearly displayed. It is thus believed that a novel "unique" feature has now been discovered that is likely to play a role in bone-mineral interactions in bone-tooth matrix class of proteins.

In conclusion, all the proteins discussed appear to form integral associations with bone mineral or tooth extracellular matrix and the interactions are thought to be mediated via integrin/RGD associations. Moreover, the new regional motif (rich in serines and aspartate) would be ideal for phosphate calcium interactions. This therefore supports the hypothesis that the C-terninus of phosphatonin plays a role in bone mineral homeostasis, and the N-terminus on renal phosphate regulation. In summary, the shared features of the proteins comprise:

1. RGD motif in similar structural context.
2. Glycoproteins.
3. Rich in aspartate and serine.
4. Casein kinase and protein kinase motifs.
5. Distinct aspartate-serine rich MEPE motif (repeated in DPP).
6. Large number of phosphorylation motif and myristoylation motifs.
7. Evidence of cleavage and/or alternative splicing.
8. All associated with bone or tooth extracellular matrix.

Thus, in a preferred embodiment of the present invention, the phosphatonin polypeptide comprises the above-described bone mineral motif, preferably the amino acid sequence of SEQ ID NO: 5 or 7 or an amino acid sequence corresponding to the same such as those from the mentioned DMP1, DSSP, BSP, OPN or DMA-1 proteins.

Bioactive Fragments

In another embodiment of the present invention, the polypeptide comprising the bioactive fragment has the reverse of phosphatonin activity and may be suitable for treating hypophosphatemic conditions. In this embodiment, the polypeptide is directly or indirectly capable of up-regulating sodium dependent phosphate cotransport and/or down-regulating 25-hydroxy vitamin D3–24-hydroxylase and/or up-regulating renal 25-hydroxy-D-1(-hydroxylase. The mentioned activities will also be referred to herein as "anti-phosphatonin" activity. However, use of the term "anti-phosphatonin" activity does not exclude the possibility that said activity is the one which is predominant of genuine phosphatonin in phosphate metabolism. These "anti-phosphatonin" activities are also readily measurable using the methodology of Rowe et al (1996) by assay using a suitable renal cell line such as CL8 or OK (deposited at the European Collection of Cell Cultures under ECACC 91021202); see also the methods referred to supra and in the appended examples. Thus, the phosphatonin polypeptides of the invention can be easily tested for phosphatonin or "anti-phosphatonin" activity according to any one of the methods referred to above or described further herein, e.g., in the appended examples; see, e.g., Example 12. Preferably, the fragment is obtainable by proteolytic cleavage of phosphatonin by a PHEX metallopeptidase. A PHEX gene has been cloned and found to encode a zinc metalloendopeptidase as discussed in Rowe (1997). Again, without intending to be bound by theory, structurally, bioactive fragments having these activities are thought to lack at least a part of the N or C terminal portion of the amino acid sequence of FIG. 8 or FIG. 15, preferably lacking the N and/or C terminal portion up to at least the putative PHEX metalloproteinase cleavage site at residues 235/236 in the amino acid sequence of SEQ ID NO: 2 or at residues 46, 125 and/or 283 of SEQ ID NO: 27. This polypeptide therefore preferably comprises no more than approximately the first 235 residues of the amino acid sequence of FIG. 8 or a fragment of the amino acid sequence of SEQ ID NO: 27 generated by PHEX cleavage at any one the mentioned amino acid positions. Naturally, further modifications of such fragments such as those described above are included within the scope of the present invention.

As is explained in Example 4, the phosphatonin polypeptide of the invention was cloned via the use of an expression library, wherein the target cDNA is fused to a portion of the (-galactosidase enzyme. In the cDNAs so obtained the N-terminal methionine was not included. However, as described in Example 13 genuine phosphatonin has an N-terminal methionine present in its amino acid sequence. Therefore, in one embodiment of the phosphatonin polypeptide of the invention the amino acid sequence of the polypeptide includes the amino acid Met added to the N-terminus.

In another embodiment, the polypeptide of the invention can be part of a fusion protein. This embodiment will be discussed further below.

The present invention further provides a polynucleotide encoding a phosphatonin polypeptide as described herein. Such polynucleotide may be a DNA such as a cDNA, or an RNA such as mRNA or any other form of nucleic acid including synthetic or modified derivatives and may encode the polypeptide in a continuous sequence or in a number of sequences interrupted by intervening sequences. In whichever form it is present, the polynucleotide is an isolated polynucleotide in that it is removed from its naturally-occurring state. This aspect of the invention is based on the cloning of the gene for human phosphatonin. In a preferred embodiment, the polynucleotide comprises the nucleotide sequence of FIG. 8 or the one depicted in SEQ ID NO: 26, optionally including one or more mutations or deletions which do not substantially affect the activity of the polypeptide encoded thereby. Such mutations include those arising from the degeneracy of the genetic code, as well as those giving rise to any of the amino acid mutations or deletions discussed above. Accordingly, by the employment of techniques routine to those skilled in molecular biology, it is possible to use the nucleotide sequence of FIG. 8 or SEQ ID NO: 26 to generate suitable polynucleotide sequences which encode polypeptides useful in the present invention. As mentioned herein before, the present invention also encompasses phosphatonin polynucleotides, wherein the nucleotide sequence comprises sequential nucleotide deletions from either the C-terminus or the N-terminus such as those described in more detail below.

Extending the Polynucleotide Sequence of the Invention

As discussed in Example 4 and 13, the phosphatonin polynucleotide obtained by the expression library was not full-length at the 5'-end. The polynucleotide sequences encoding the phosphatonin polypeptides can thus be extended utilizing partial nucleotide sequence and various methods known in the art to detect upstream sequences such as promoters and regulatory elements; see also Example 13. Gobinda, (PCR Methods Applic. 2 (1993), 318–322) discloses "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia, Nucleic Acids Res. 16 (1988), 8186). The primers may be designed using OLIGO(r) 4.06 Primer Analysis Software (1992; National Biosciences Inc, Plymouth Minn.), or another appropriate program to be preferably 22–30 nucleotides in length, to have a GC content of preferably 50% or more, and to anneal to the target sequence at temperatures preferably about 68–72 C. The method uses several restriction enzymes to generate a suitable fragment in the known region of a gene. The fragment is then circularized by intramolecular ligation and used as a PCR template.

Capture PCR (Lagerstrom, PCR Methods Applic. 1 (1991), 111–119) is a method for PCR amplification of DNA fragments adjacent to a known sequence in, e.g., human yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker, (Nucleic Acids Res. 19 (1991), 3055–3060). Additionally, one can use PCR, nested primers and PromoterFinder libraries to walk in genomic DNA (PromoterFinder™ Clontech (Palo Alto Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Furthermore, direct sequencing of primer extension products may be employed. Genomic libraries are useful for extension into the 5' nontranslated regulatory region. Capillary electrophoresis may be used to analyze the size or confirm the nucleotide sequence of sequencing or PCR products; see, e.g., Sambrook, supra. Systems for rapid sequencing are available from Perkin Elmer, Beckmann Instruments (Fullerton Calif.), and other companies.

Computer-assisted Identification of Phosphatonin Polypeptides and their Encoding Genes BLAST2, which stands for Basic Local Alignment Search Tool (Altschul, Nucleic Acids Res. 25 (1997), 3389–3402; Altschul, J. Mol. Evol. 36 (1993), 290–300;-Altschul, J. Mol. Biol. 215 (1990), 403–410), can be used to search for local sequence alignments. BLAST produces alignments of both nucleotide and amino acid sequences to determine sequence similarity. Because of the local nature of the alignments, BLAST is especially useful in determining exact matches or in identifying homologs. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul, 1997, 1993 and 1990, supra) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or homologous. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

Examples of the different possible applications of the phosphatonin polynucleotides and polypeptides according to the invention as well as molecules derived from them will be described in detail in the following.

Phosphatonin Polynucleotides and Polypeptides

The phosphatonin was isolated from a cDNA library constructed from MRNA extracted from a meningeal phosphaturic-mesenchymal-tumour resected from a patient suffering from oncogenic hypophosphatemic osteomalacia; see Example 4 and 13.

The phosphatonin nucleotide sequence identified as SEQ ID NO: 1 was assembled from partially homologous ("overlapping") sequences obtained from related DNA clones. The overlapping sequences were assembled into a single contiguous sequence of high redundancy (usually three to five overlapping sequences at each nucleotide position), resulting in a final sequence identified as SEQ ID NO: 1. SEQ ID NO: 26 containing the additional nucleotide sequence encoding the 5'-terminus of phosphatonin has been isolated from the same tumor cDNA library constructed for the isolation of the clones resulting in SEQ ID NO: 1. Therefore, SEQ ID NO: 1 and 26 and the translated SEQ ID NO:2 and 27, respectively, are sufficiently accurate and otherwise suitable for a variety of uses well known in the art and described further below. For instance, SEQ ID NO: 1 and 26 are useful for designing nucleic acid hybridization probes that will detect nucleic acid sequences contained in SEQ ID NO: 1 and 26. These probes will also hybridize to nucleic acid molecules in biological samples, thereby enabling a variety of forensic and diagnostic methods of the invention. Similarly, polypeptides identified from SEQ ID NO:2 or 27 may be used to generate antibodies which bind specifically to phosphatonin.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO: 1 and 26 and the predicted translated amino acid sequence identified as SEQ ID NO:2 and 27, respectively, but also means for the cloning of the cDNA and genomic DNA corresponding to the nucleotide sequence in SEQ ID NO:1 and 26. The nucleotide sequence of the so obtained phosphatonin clones can readily be determined by sequencing the clone in accordance with known methods. The predicted phosphatonin amino acid sequence can then be verified from such cDNA or genomic clones. Moreover, the amino acid sequence of the protein encoded by the obtained clones can also be directly determined by peptide sequencing or by expressing the protein in a suitable host cell, collecting the protein, and determining its sequence and function according to the methods described herein.

The present invention also relates to the phosphatonin gene corresponding to SEQ ID NO: 1 and 26. The phosphatonin gene can be isolated in accordance with known methods using the sequence information disclosed herein. Such methods include preparing probes or primers from the disclosed sequence and identifying or amplifying the phosphatonin gene from appropriate sources of genomic material.

Also provided in the present invention are species homologs of phosphatonin. Species homologs may be isolated and identified by making suitable probes or primers from the sequences provided herein and screening a suitable nucleic acid source for the desired homologue.

Thus, by the provision of the nucleotide sequence of SEQ ID NO: 1 and 26 as well as those encoding the amino acid sequence depicted in SEQ ID NO: 2 and 27, it is possible to isolate identical or similar nucleic acid molecules which encode phosphatonin proteins from other species or organisms, in particular orthologous phosphatonin genes from mammals other than human. The term "orthologous" as used herein means homologous sequences in different species that arose from a common ancestor gene during speciation. Orthologous genes may or may not be responsible for a similar function; see, e.g., the glossary of the "Trends Guide to Bioinformatics", Trends Supplement 1998, Elsevier Science.

The phosphatonin polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Phosphatonin polypeptides are preferably provided in an isolated form, and preferably are substantially purified. A recombinantly produced version of a phosphatonin polypeptide, including the secreted polypeptide, can be substantially purified by the one-step method described in Smith and Johnson, Gene 67 (1988), 31–40. Phosphatonin polypeptides also can be purified from natural or recombinant sources using antibodies of the invention raised against the phosphatonin protein in methods which are well known in the art.

Polynucleotide and Polypeptide Variants

"Variant" refers to a polynucleotide or polypeptide differing from the phosphatonin polynucleotide or polypeptide, but retaining essential properties thereof such as the immunological and preferably biological activity referred to above. Generally, variants are overall closely similar, and, in many regions, identical to the phosphatonin polynucleotide or polypeptide.

Such polynucleotides comprise those which encode fragments, analogues or derivatives and in particular orthologues of the above-described phosphatonin proteins and differ, for example, by way of amino acid and/or nucleotide deletion(s), insertion(s), substitution(s), addition(s) and/or recombination(s) or any other modification(s) known in the art either alone or in combination from the above-described amino acid sequences or their uriderlying nucleotide sequence(s). Methods for introducing such modifications in the nucleic acid molecules according to the invention are well-known to the person skilled in the art. All such fragments, analogues and derivatives of the protein of the invention are included within the scope of the present invention, as long as the essential characteristic immunological and/or biological properties as defined above remain unaffected in kind.

The term "variant" means in this context that the nucleotide and their encoded amino acid sequence, respectively, of these polynucleotides differs from the sequences of the above-described phosphatonin polynucleotides and polypeptides in one or more nucleotide positions and are highly homologous to said nucleic acid molecules. Homology is understood to refer to a sequence identity of at least 40%, preferably 50%, more preferably 60%, still more preferably 70%, particularly an identity of at least 80%, preferably more than 90% and still more preferably more than 95%. The deviations from the sequences of the nucleic acid molecules described above can, for example, be the result of nucleotide substitution(s), deletion(s), addition(s), insertion(s) and/or recombination(s); see supra. Homology can further imply that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other mammals, or mutations. These mutations may occur naturally or may be obtained by mutagenesis techniques. The allelic variations may be naturally occurring allelic variants as well as synthetically produced or genetically engineered variants; see supra.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the phosphatonin polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of SEQ ID NO: 1 or 26, the ORF (open reading frame), or any fragment specified as described herein.

As a practical matter, whether any particular nucleic acid molecule or polypeptide is at least 40%, 50%, 60%, 70%, 80%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6 (1990), 237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino, acid residues in the subject sequence may be inserted, deleted, added or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 40%, 50%, 60%, 70%, 80%; 90%, 95%, 96%, 97%, 98% or 99% identical to, for instance, the amino acid sequences shown in SEQ ID NO: 2 or 27 can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6 (1990), 237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAMO, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for ihe purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The phosphatonin variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Phosphatonin polynucleotide variants can be produced for a variety of reasons, e.g., to optimize codon expression for a particular host (change codons in the human mRNA to those preferred by a bacterial host such as *E. coli*).

Naturally occurring phosphatonin variants are called "allelic variants," and refer to one of several alternate forms of a gene occupying a given locus on a chromosome of an organism. (Genes II, Lewin, B., ed., John Wiley & Sons, New York (1985) and updated versions). These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the phosphatonin polypeptides. For instance, one or more amino acids can be deleted from the N-terminus or C-terminus of the protein without substantial loss of biological function. The authors of Ron, J. Biol. Chem. 268 (1993), 2984–2988, reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli, J. Biotechnology 7 (1988), 199–216).

Moreover, ample evidence demonstrates that variants often retain a biological activity similar to that of the naturally occurring protein. For example, Gayle and coworkers (J. Biol. Chem. 268 (1993); 22105–22111) conducted extensive mutational analysis of human cytokine IL-1a. They used random mutagenesis to generate over 3,500 individual IL-1 a mutants that averaged 2.5 amino acid changes per variant over the entire length of the molecule. Multiple mutations were examined at every possible amino acid position. The investigators found that "[m]ost of the molecule could be altered with little effect on either [binding or biological activity]"; see Abstract. In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art. Furthermore, using the PESTFIND program (Rogers, Science 234 (1986), 364–368), PEST sequences (rich in proline, glutamic acid, serine, and threonine) can be identified, which are characteristically present in unstable proteins. Such sequences may be removed from the phosphatonin proteins in order to increase the stability and optionally the activity of the proteins. Methods for introducing such modifications in the nucleic acid molecules according to the invention are well-known to the person skilled in the art.

Thus, the invention further includes phosphatonin polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, Science 247 (1990), 1306–1310, wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244 (1989), 1081–1085) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of phosphatonin include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretary sequence, or a sequence facilitating purification. Such variant polypeptides are deemed to be within the scope of those skilled in the art from the teachings herein.

For example, phosphatonin polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity; see, e.g. Pinckard, Clin. Exp. Immunol. 2 (1967), 331–340; Robbins, Diabetes 36 (1987), 838–845; Cleland, Crit. Rev. Therapeutic Drug Carrier Systems 10 (1993), 307–377.

Polynucleotide and Polypeptide Fragments

In the present invention, a "polynucleotide fragment" refers to a short polynucleotide having a nucleic acid sequence contained in SEQ ID NO: 1 or 26. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the nucleotide sequence shown in SEQ ID NO: 1 or 26. These nucleotide fragments are useful as diagnostic probes and primers as discussed herein. Of course, larger fragments (e.g., 50, 150, 500, 600, 1000 nucleotides) are preferred.

Moreover, representative examples of phosphatonin polynucleotide fragments include, for example, fragments having a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, or 1901–1950 of SEQ ID NO: 26. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO: 2 or 27. Protein fragments may be "free-standing", or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, 161–180, 181–200, 201–220, 221–240, 241–260, 261–280, 281–300, 301–3201, or 321–340, 341–360, 361–380, 381–400, 401–420, 421–440, 441–460, 461–480, 481–500, and 501–520 to the end of the coding region in SEQ ID NO: 26. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the phosphatonin protein having a continuous series of deleted residues from the amino or the carboxy terminus, or both. For example, any number of amino acids, ranging from 1–60, can be deleted from the amino terminus of the phosphatonin polypeptide. Similarly, any number of amino acids, ranging from 1–30, can be deleted from the carboxy terminus of the phosphatonin protein. Furthermore, any combination of the above amino and carboxy terminus deletions are preferred. Similarly, polynucleotide fragments encoding these phosphatonin polypeptide fragments are also preferred. Particularly, N-terminal deletions of the phosphatonin polypeptide can be described by the general formula m-525, where m is an integer from 2 to 520 where m corresponds to the position of the amino acid residue identified in SEQ ID NO: 27.

Also preferred are phosphatonin polypeptide and polynucleotide fragments characterized by structural or functional domains. Preferred embodiments of the invention include fragments that comprise alpha-helix and alpha-helix forming regions ("alpha-regions"), beta-sheet and beta-sheet-forming regions ("beta-regions"), turn and turn-forming regions ("tum-regions"), coil and coil-forming regions ("coil-regions"), hydrophilic regions, hydrophobic regions, alpha amphipathic regions, beta amphipathic regions, flexible regions, surface-forrning regions, substrate binding region, and high antigenic index regions. As set out in the Figures, such preferred regions include Garnier-Robson- alpha-regions, beta-regions, turn-regions, and coil-regions, Chou-Fasman alpha-regions, beta-regions, and turn-regions, Kyte-Doolittle hydrophilic regions and hydrophobic regions, Eisenberg alpha and beta amphipathic regions, Karplus-Schulz flexible regions, Emini surface-forming regions, and Jameson-Wolf high antigenic index regions. Polyp eptide fragments of SEQ ID NO: 2 and 27 falling within conserved domains are specifically contemplated by the present invention and shown in the Figures. Moreover, polynucleotide fragments encoding these domains are also contemplated.

Other preferred fragments are biologically active phosphatonin fragments. Biologically active fragments are those exhibiting activity similar, but not necessarily identical, to an activity of the phosphatonin polypeptide. The biological activity of the fragments may include an improved desired activity, or a decreased undesirable activity.

However, many polynucleotide sequences, such as EST sequences, are publicly available and are accessible through sequence databases. Some of these sequences may be related to SEQ ID NO: 1 or 26 and may have been publicly available prior to conception of the present invention. Preferably, such related polynucleotides are specifically excluded from the scope of the present invention. To list every related sequence would be cumbersome.

Accordingly, preferably excluded from the present invention are one or more polynucleotides comprising a nucleotide sequence described by the general formula of a-b, where a is any integer between 1 to 1989 of SEQ ID NO: 26, b is an integer of 15 to 1989, where both a and b correspond to the positions of nucleotide residues shown in SEQ ID NO: 26, and where the b is greater than or equal to a +14.

Epitopes & Antibodies

In the present invention, "epitopes" refer to phosphatonin polypeptide fragments having antigenic or immunogenic activity in an animal, e.g., a rat, a rabbit, a human, a mouse (including a transgenic mouse which carry human immunoglobulin genes and produce human antibody molecules), and so on. A preferred embodiment of the present invention relates to a phosphatonin polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response; see, for instance, Geysen, Proc. Natl. Acad. Sci. USA 81 (1983); 3998–4002. Fragments which function as epitopes may be produced by any conventional means; see, e.g., Houghten, Proc. Natl. Acad. Sci. USA 82 (1985), 5131–5135 further described in U.S. Pat. No. 4,631,211.

In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope; see, for instance, Wilson, Cell 37 (1984), 767–778; Sutcliffe, Science 219 (1983), 660–666.)

Similarly, immunogenic epitopes can be used to induce antibodies according to methods well known in the art; see, for instance, Sutcliffe, supra; Wilson, supra; Chow, Proc. Natl. Acad. Sci. USA 82 (1985), 910–914; and Bittle, J. Gen. Virol. 66 (1985); 2347–2354. A preferred immunogenic epitope includes the soluble protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

Using the computer program GCG-Peptide-structure (Rice, Programme Manual for the EGCG package, Cambridge, CB10 1RQ England: Hinxton Hall; 1995) available from the Human Genome Resource Centre (http://www.hgmp.mrc.ac.uk/homepage.html), SEQ ID NO:2 was found antigenic at amino acids regions shown in FIG. 4. Thus, these regions could be used as epitopes to produce antibodies against the protein encoded by SEQ ID NO: 1. Preferably, the antibody of the present invention specifically recognizes an epitope combined in or formed with amino acid residues 1 to 96, more preferably residues 47 to 96 of SEQ ID NO: 27.

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody; see, e.g., Wahl, J. Nucl. Med. 24 (1983), 316–325. Thus, these fragments are preferred, as well as the products of a FAB or other immunoglobulin expression library. Moreover, antibodies of the present invention include chimeric, single chain, humanized antibodies, human antibodies obtainable by or from phage display, a transgenic mouse carrying human immunoglobulin genes and/or human chromosomes, isolated immune cells from human body, in vitro or ex vivo immunization of human immune cells, or any other available methods.

In another embodiment, the present invention relates to a nucleic acid molecule which hybridizes with the complementary strand of the phosphatonin polynucleotide of the invention and which encodes a mutated version of the protein as defined above which has lost its immunological, preferably one of its biological activities. This embodiment may prove useful for, e.g., generating dominant mutant alleles of the above-described phosphatonin proteins. Said mutated version is preferably generated by substitution, deletion and/or addition of 1 to 5 or 5 to 10 amino acid residues in the amino acid sequence of the above-described wild type proteins. For example, any one of the putative functional and structural motifs shown in FIG. 15 can be mutated and altered, substituted or otherwise modified, either alone or in combination.

Vectors, Host Cells and Protein Production

The present invention also relates to vectors containing the phosphatonin polynucleotide, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

Phosphatonin polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The phosphatonin polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art. Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXTI and pSG available from Stratagene; and pSVK3, pBPV, pMSG and pSVL available from Pharmacia. Other suitable vectors will be readily apparent to the skilled artisan.

Furthermore, one could use, e.g., a mammalian cell that already comprises in its genome a nucleic acid molecule encoding a phosphatonin polypeptide as described above, but does not express the same or not in an appropriate manner due to, e.g., a weak promoter, and introduce into the mammalian cell an expression control sequence such as a strong promoter in close proximity to the endogenous nucleic acid molecule encoding said phosphatonin polypeptide so as to induce expression of the same.

In this context the term "expression control sequence" denotes a nucleic acid molecule that can be used to increase the expression of the phosphatonin polypeptide, due to its integration into the genome of a cell in close proximity to the phosphatonin encoding gene. Such regulatory sequences comprise promoters, enhancers, inactivated silencer intron sequences, 3UTR and/or 5'UTR coding regions, protein and/or RNA stabilizing elements, nucleic acid molecules encoding a regulatory protein, e.g., a transcription factor, capable of inducing or triggering the expression of the phosphatonin gene or other gene expression control elements which are known to activate gene expression and/or increase the amount of the gene product. The introduction of said expression control sequence leads to increase and/or induction of expression of phosphatonin polypeptides, resulting in the end in an increased amount of phosphatonin polypeptides in the cell. Thus, the present invention is aiming at providing de novo and/or increased expression of phosphatonin polypeptides.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis, Basic Methods In Molecular Biology (1986). It is specifically contemplated that phosphatonin polypeptides may in fact be expressed by a host cell lacking a recombinant vector.

Phosphatonin polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Phosphatonin polypeptides can also be recovered from products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the phosphatonin polypeptides may be glycosylated or may be non-glycosylated. In addition, phosphatonin polypeptides may also include an initial (modified) methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In a particularly preferred embodiment, the present invention relates to a process for isolating a phosphatonin polypeptide comprising the steps of:

(a) culturing tumor-conditioned media or osteosarcoma cells to confluence in serum supplemented media (DMEM Eagles/10% FCS/glutamine/antimycotic (DMFCS);

(b) incubating the cells on alternate days in serum free media DMEM Eagles/glutamine/antimycotic antibiotic (DM) up to five hours;

(c) collecting conditioned serum free media from the cells and equilibrating the conditioned media to 0.06M sodium phosphate pH 7.2 and 0.5 M NaCl (PBS);

(d) subjecting the media from (c) to an equilibrated column of concanavilin A sepharose;

(e) washing the column extensively with PBS;

(f) eluting the concanavalin A column with PBS supplemented with 0.5 M (-methyl-D-glucopyranoside;

(g) subjecting the eluted material from (f) to cation exchange chromatography; and (h) eluting phosphatonin polypeptide containing fractions with 0.5 M NaCl.

The above-described method is illustrated in Example 1.

Another subject of the invention is a method for the preparation of phosphatonin polypeptides which comprises the cultivation of host cells according to the invention which, due to the presence of a vector or a polynucleotide according to the invention or an exogenous expression control sequence, are able to express such a polypeptide, under conditions which allow expression of the polypeptide and recovering of the so-produced polypeptide from the culture. It is also to be understood that the proteins can be expressed in a cell free system using for example in vitro translation assays known in the art.

Hence, in a still further embodiment, the present invention relates to a phosphatonin polypeptide or an immunologically and/or biologically active fragment thereof encoded by the polynucleotide of the invention or produced by a method of as described above. Likewise phosphatonin polypeptides are within the scope of the present invention which are obtainable by proteolytic cleavage of the above described phosphatonin polypeptides by a PHEX metallopeptidase.

It will be apparent to those skilled in the art that the protein of the invention can be further coupled to other moieties as described above for, e.g., drug targeting and imaging applications. Such coupling may be conducted chemically after expression of the protein to site of attachment or the coupling product may be engineered into the protein of the invention at the DNA level. The DNAs are then expressed in a suitable host system, and the expressed proteins are collected and renatured, if necessary.

As explained above, phosphatonin comprising the amino acid sequence depicted in SEQ ID. NO: 27 has an N-terminus with two cysteines, one of which is optimally placed for the formation of homo- and/or heterodimers. Thus, it is envisaged that within the cell functional phosphatonin is present as a homo- or heterodimer. Therefore, in a preferred embodiment of the present invention, phosphatonin forms a homo- or heterodimer:

On the other hand, it could be shown in accordance with the present invention, that recombinant truncated phosphatonin that lacks both cysteine residues in its amino acid sequence, has phosphate-retaining properties thus useful in therapeutic applications. Accordingly, in another preferred embodiment of the present invention, the cysteine residues in the phosphatonin polypeptide of the present invention are substituted, deleted and/or blocked, preferably such that the phosphatonin polypeptide is no longer capable of forming homo- and/or heterodimers, for example, due to disulfide bridges.

Regulation of a Phosphate Metabolism

As mentioned hereinbefore, the phosphatonin polypeptide of the present invention is capable of regulating phosphate metabolism in different ways. Thus, in one embodiment, the present invention relates to a phosphatonin polypeptide having phosphatonin activity in that it has at least one of the following activities:

(a) it is capable of down-regulating sodium dependent phosphate co-transport;

(b) it is capable of up-regulating renal 25-hydroxy vitamin D3–24-hydroxylase; and/or (c) it is capable of down-regulating renal 25-hydroxy-D-1-α-hydroxylase.

In another embodiment, the present invention relates to a phosphatonin polypeptide having anti-phosphatonin activity in that it has at least one of the following activities:

(a) it is capable of up-regulating sodium dependent phosphate co-transport;

(b) it is capable of down-regulating renal 25-hydroxy vitamin D3–24-hydroxylase; and/or (c) it is capable of up-regulating renal 25-hydroxy-D-1-α-hydroxylase.

In a particularly preferred embodiment of the present invention, the phosphatonin polypeptide comprises a bone mineral motif as described above and positively regulates bone mineralization.

In a still further embodiment, the present invention relates to phosphatonin polypeptides which have lost at least one of the above described activities. Such polypeptides may be mutant forms of the phosphatonin polypeptide of the present invention and can, e.g., be used for studying the effect of mutations in the phosphatonin encoding gene. In particular, such mutants may prove useful for the development of drugs that are capable of compensating a deficiency caused by the loss of one of the biological activities of the wildtype phosphatonin. Such mutant forms of phosphatonin polypeptides may best be studied in the screening methods described in more detail hereinbelow.

Phosphatonin Antibodies

Furthermore, as described above, the provision of the phosphatonin polypeptide of the present invention enables the production of phosphatonin specific antibodies. In this respect, hybridoma technology enables production of cell lines secreting antibody to essentially any desired substance that produces an immune response. RNA encoding the light and heavy chains of the immunoglobulin can then be obtained from the cytoplasm of the hybridoma. The 5' end portion of the MRNA can be used to prepare cDNA to be inserted into an expression vector. The DNA encoding the antibody or its immunoglobulin chains can subsequently be expressed in cells, preferably mammalian cells. Depending on the host cell, renaturation techniques may be required to attain proper conformation of the antibody. If necessary, point substitutions seeking to optimize binding may be made in the DNA using conventional cassette mutagenesis or other protein engineering methodology such as is disclosed herein.

Thus, the present invention also relates to an antibody specifically recognizing the phosphatonin polypeptide of the invention.

In a preferred embodiment of the invention, said antibody is a monoclonal antibody, a polyclonal antibody, a single chain antibody, human or humanized antibody, primatized, chimerized or fragment thereof that specifically binds said peptide or polypeptide also including bispecific antibody, synthetic antibody, antibody fragment, such as Fab, Fv or scFv fragments etc., or a chemically modified derivative of any of these. The general methodology for producing antibodies is well-known and has been described in, for example, K÷hler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982), as well as that taught by L. T. Mimms et al., Virology 176 (1990), 604–619. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988.

For the production of antibodies in experimental animals, various hosts including goats, rabbits, rats, mice, and others, may be immunized by injection with polypeptides of the present invention or any fragment or oligopeptide or derivative thereof which has immunogenic properties. Techniques for producing and processing polyclonal antibodies are known in the art and are described in, among others, Mayer and Walker, eds., "Immunochemical Methods in Cell and Molecular Biology", Academic Press, London (1987). Polyclonal antibodies also may be obtained from an animal, preferably a mammal. Methods for purifying antibodies are known in the art and comprise, for example, immunoaffinity chromatography. Depending on the host species, various adjuvants or immunological carriers may be used to increase immunological responses. Such adjuvants include, but are not limited to, Freund's, complete or incomplete adjuvants, mineral gels such as aluminium hydroxide, and surface active substances such as lysolecithin, pluronic polyols, polyanions, peptides, oil emulsions and dinitrophenol. An example of a carrier, to which, for instance, a peptide of the invention may be coupled, is keyhole limpet hemocyanin (KLH).

The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735.

In a preferred embodiment, the antibody of the invention has an affinity of at least about 10-7 M, preferably at least about 10-8 M more preferably at least about 10-9 M and most preferably at least about 10—10 M. On the other hand, the phosphatonin antibody may have a binding affinity of about 105 M-1, preferably not higher than 107 M-1 if stimulation of phosphatonin activity is envisaged and advantageously up to 1010 M-1 or more in case phosphatonin activity should be suppressed. As mentioned hereinbefore, the antibody of the present invention preferably specifically recognizes an epitope contained or formed with amino acid residues 1 to 46 and 47 to 525, and more preferably 1 to 46, and 47 to 96 of the amino acid sequence depicted in SEQ ID NO: 27.

Uses of the Phosphatonin Polynucleotides

The phosphatonin polynucleotides identified herein can be used in numerous ways as reagents. The, following description should be considered exemplary and utilizes known techniques.

There exists an ongoing need to identify new chromosome markers, since few chromosome marking reagents, based on actual sequence data (repeat polymorphisms), are presently available. Phosphatonin related polynucleotides (genomic and/or CDNA) can be used to carry out restriction analysis as described in detail (Rowe, Hum. Genet. 94:5 (1994), 457–467; Benham, Genomics 12 (1992), 368–376; Gillett, Ann. Hum. Genet. 60(3) (1996), 201–211; Rowe, Nucleic Acids Res. 22(23) (1994), 5135–5136). In particular, the use of microsatellites (Rowe, Hum. Genet. 94:5 (1994), 457–467; Rowe, Nucleic Acids Res. 22(23) (1994), 5135–5136; Rowe, Hum. Genet. 93 (1994), 291–294; Rowe, Hum. Genet. 91 (1993), 571–575; Rowe, Hum. Genet. 97 (1996), 345–352; Rowe, Hum. Genet. 89 (1992), 539–542), and the isolation of informative markers using irradiation-fusion-gene-transfer hybrids and ALU-PCR (Benham, Genomics 12 (1992), 368–376) will enable the rapid isolation of highly informative methods for the screening of phosphatonin and derivative inherited diseases. The above methodologies have been particularly successful in the mapping and localization of the PHEX gene (MEPE is proposed to a PHEX substrate), and extensive mutation analysis has revealed structural regions and motifs prerequisite for PHEX bio-activity (Rowe, Hum. Mol. Genet. 6 (1997), 539–549; Rowe, Exp. Nephrol. 5 (1997), 355–363; Rowe, Current Opinion in Nephrology & Hypertension 7(4) (1998), 367–376; Rowe, Clinical and Experimental Nephrology 2(3) (1998), 183–193), these same approaches can be used for phosphatonin. More recently powerful genome-wide linkage and screening techniques have been developed that rely on single nucleotide polymorphisms (SNP's), and the use of a combination of gel-based sequencing and high-density variation-detection DNA chips (Wang, Science 280 (1998), 1077–1082). Recently SNP data has been made available on the internet by the Center for Genome Research at the Whitehead Institute for Biomedical Research in Cambridge, Mass., USA (Whitehead-MIT) at http://www-genome.wi.mit.edu/SNP/human/index.html. This powerful new oligonucleotide-array based methodology will be the future route for molecular expression analysis, polymorphism and genotyping, and disease management (Wang, Science 280 (1998), 1077–1082; Chee, Science 274 (1996), 610–614; Gentalen, Nucleic Acids Res. 27 (1999), 1485–1491; Hacia, Nucleic Acids Res. 26 (1998), 3865–3866; Lipshutz, Nat. Genet. 21 (1999), 20–24; Fan, Eur. J. Hum. Genet. 6 (1998), 134). Given the sequence information for MEPE in this application the above new approaches and technology will be used to address the areas described. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price (Blood Rev. 7 (1993), 127–134) and Trask (Trends Genet. 7 (1991), 149–154). The technique of fluorescent in situ hybridization of chromosome spreads has been described, among other places, in Verma, (1988) Human Chromosomes: A Manual of Basic Techniques, Pergamon Press, New York N.Y. Fluorescent in situ hybridization of chromosomal preparations and other physical chromosome mapping techniques may be correlated with additional genetic map data. Extensive mapping data accessible to the scientific community can be found on the internet at sites sponsored by the Human-Genome-Mapping-Project United Kingdom (HGMP-RC) http://www.hgmp.mrc.ac.uk/homepage.html, the National Collection of biological information (NCBI) sponsored by the National Institute of Health USA (NIH), http://ww.ncbi.nlm.nih.gov/, also the Center for Genome Research at the Whitehead Institute for Biomedical Research in Cambridge, Mass., USA (Whitehead-MIT) http://www-genome.wi.mit.edu/. Moreover, extensive microsatellite-maps and related mapping tools covering the entire human genome can also be accessed via Genethon (French Government sponsored database) http://www.genethon.fr/genethon_en.html. Seminal maps have also been published in Science and Nature (see, for example, Dib, Nature 380 (1996), 152–154), but for up to date data the internet sites should be consulted. Correlation between the location of the gene encoding a phosphatonin polypeptide of the invention on a physical chromosomal map and a specific feature, e.g., a hypo- or hyperphosphatemic disease may help to delimit the region of DNA associated with this feature. The nucleotide sequences of the subject invention may be used to detect differences in gene sequences between normal, carrier or affected individuals. Furthermore, the means and methods described herein can be used for marker-assisted animal breeding. The nucleotide sequence of the subject invention may also be used to detect differences in the chromosomal location due to translocation, inversion, etc. among normal, carrier or affected individuals.

In the very least, the phosphatonin polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response. In a preferred embodiment, the described phosphatonin oligonucleotide comprises at least 15, preferably 20 nucleotides of nucleotides 1 to 335 of SEQ ID NO: 26 or of corresponding nucleotide sequences degenerate to this nucleotide sequence and/or capable of specifically hybridizing to this nucleotide sequence. In the latter, it is preferred that the nucleotide sequence is at least 70% or more, preferably 80%, and most preferably 90% identical to the corresponding sequence in SEQ ID NO: 26 or its degenerated nucleotide sequence.

Uses of Phosphatonin Polypeptides and Antibodies

Phosphatonin polypeptides and antibodies thereto can be used in numerous ways. The following description should be considered exemplary and utilizes known techniques.

Phosphatonin polypeptides can be used to assay protein levels in a biological sample using antibody-based techniques. For example, protein expression in tissues can be studied with classical immunohistological methods; see, e.g., Jalkanen, J. Cell. Biol. 101 (1985), 976–985; Jalkanen, J. Cell. Biol. 105 (1987), 3087–3096.) Other antibody based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14 C), sulfur (35S), tritium (3H), indium (112In), and technetium (99 mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 121In, 99 mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in, e.g., Burchiel, "Immunopharmacokinetics of Radiolabeled Antibodies and Their Fragrnents", Chapter 13 in Tumor Imaging: The Radiochemical Detection of Cancer, Burchiel and Rhodes, eds., Masson Publishing Inc. (1982).

Thus, the invention provides a diagnostic method of a disorder, which involves (a) assaying the expression of phosphatonin polypeptide in cells or tissues, or the level of phosphatonin or its active fragments or epitopes in the body fluid of an individual; (b) comparing the level of gene expression with a standard gene expression level, whereby an increase or decrease in the assayed phosphatonin polypeptide gene expression level compared to the standard expression level is indicative of a disorder.

Moreover, phosphatonin polypeptides can be used to treat disease. For example, patients can be administered phosphatonin polypeptides in an effort to increase or decrease serum phosphate level and/or improve the impaired bone formation (X-Linked Hyophosphatemic Rickets, Oncogenic Hypophosphatemic Osteomalacia, Renal Failure, Osteoporosis, Renal Osteodystrophy, and so forth). It can activate or inhibit its receptors to up- or down-regulate the expression of sodium dependent phosphate co-transporters. In addition, the phosphatonin gene promoter and/or enhancer element can be used in gene therapy applications for treating phosphate metabolism-specific disorders, particularly X-Linked Hypophosphatemic Rickets. Also, possibly in skeletal-mineral loss disorders where inappropriate gene regulation and/or post-translational modification of MEPE occurs due to undefined secondary or primary changes (e.g., postmenopausal women, osteoposis, age related), where supplementation of the hormone (and/or agonists-antagonists to receptor or hormone) perhaps as an adjunct to hormone replacement therapy would restore phosphate and bone-mineral balance. A key feature of MEPE bio-activity and, thus, disease-treatment is the prediction that N-terminal sequence regulates renal phosphate uptake, and the C-terminus (notably regions associated with the MEPE-motif described earlier) is pre-requisite for normal bone mineralization and growth.

After renal-transplantation, chronic hyperphosphatemia or in some cases hypophosphatemia are key features that result in major clinical complications. For example, renal transplantation of a normal kidney into a male HYP patient was reported to result in pathophysiological changes in the normal transplanted kidney such that a "rickets-type" renal phosphate leak developed (Morgan, Arch. Intern. Med. 134 (1974), 549–552). The clinical use of N-terminal-cleaved processed-fragments of MEPE could result in effective anti-hypophosphatemic therapy. In contrast, renal-transplantation cases that result in hyperphosphatemia could be treated with whole recombinant MEPE or active derivative peptides modeled on distinct N-terminal residues. Other diseases that could benefit from treatment with MEPE, MEPE derivative peptides, receptor antagonists-agonists (peptides could be modified to increase potency and specificity of action) include renal osteodystrophy, renal toxicity, Pagets disease of bone, autosomal-forms of rickets, certain forms of renal Fanconi syndrome. Moreover, if receptors are expressed in a range of tissues (intestines, etc.) as well as the kidney, then the potential for treating patients with end stage renal disease exists (i.e. complete loss of kidney function).

Similarly, antibodies directed to phosphatonin polypeptides can also be used to treat disease. For example, administration of an antibody directed to a phosphatonin polypeptide can bind and reduce overproduction of the polypeptide. Similarly, administration of an antibody can activate the polypeptide, such as by binding to a polypeptide and cleaving it to a different activity form.

At the very least, the phosphatonin polypeptides can be used as molecular weight markers on SDS-PAGE gels or on molecular sieve gel filtration columns using methods well known to those of skill in the art. Phosphatonin polypeptides can also be used to raise antibodies, which in turn are used to measure protein expression from a recombinant cell, as a way of assessing transformation of the host cell.

Furthermore, phosphatonin polynucleotides and polypeptides can be used in assays to test for one or more biological activities. If phosphatonin polynucleotides and polypeptides do exhibit activity in a particular assay, it is likely that phosphatonin may be involved in the diseases associated with the biological activity. Therefore, phosphatonin could be used to treat the associated disease.

Regulatory Sequences of Phosphatonin Genes

In a further aspect the present invention relates to a regulatory sequence of a promoter naturally regulating the expression of a polynucleotide encoding the phosphatonin polypeptide of the invention described above or of a polynucleotide homologous to a polynucleotide of the invention. With methods well known in the art it is possible to isolate the regulatory sequences of the promoters that naturally regulate the expression of the above-described DNA sequences. For example, using the above described nucleic acid molecules as probes a genomic library consisting of human genomic DNA cloned into phage or bacterial vectors can be screened by a person skilled in the art. Such a library consists e.g. of genomic DNA prepared from human blood cells, fractionized in fragments ranging from 5 kb to 50 kb, cloned into the lambda GEM11 (Promega) phages. Phages hybridizing with the probes can be purified. From the purified phages DNA can be extracted and sequenced. For example, a human genomic P1 library (Genomic Systems, Inc.) is screened by a labeled cDNA probe as described in Example 11. Having isolated the genomic sequences corresponding to the genes encoding the above-described phosphatonin proteins, it is possible to fuse heterologous DNA sequences to these promoters or their regulatory sequences via transcriptional or translational fusions well known to the person skilled in the art. In order to identify the regulatory sequences and specific elements of these phosphatonin genes, 5'-upstream genomic fragments can be cloned in front of marker genes such as luc, gfp or the GUS coding region and the resulting chimeric genes can be transfected into cells or animals for transient or stable expression. The expression pattern observed in the transgenic animals or transfected mammalian cells containing the marker gene under the control of the regulatory sequences of the invention can be compared with that of the phosphatonin gene described in Example 10 and reveals the boundaries of the promoter and its regulatory sequences. Usually, said regulatory sequence is part of a recombinant DNA molecule, e.g., a vector see supra. The present invention furthermore relates to host cells transformed with a regulatory sequence or a DNA molecule or vector containing the regulatory sequence of the invention. Said host cell may be a prokaryotic or eukaryotic cell; see supra.

Diagnosing Disorders of Phosphate Metabolism

Another object of the present invention concerns the pharmacogenomic selection of drugs and prodrugs for patients suffering from disorders in phosphate metabolism (see, e.g., Example 6) and which are possible candidates to drug therapy. Thus, the findings of the present invention provide the options of development of new drugs for the pharmacological intervention with the aim of restituting the function of genetically modified phosphatonin proteins. Also a gene therapeutical approach can be envisaged with the aid of the present invention.

Thus, the invention provides a diagnostic method of a disorder, which involves:

(a) assaying phosphatonin gene expression level in cells or body fluid of an individual; and (b) comparing the phosphatonin gene expression level with a standard phosphatonin gene expression level, whereby an increase or decrease in the assayed phosphatonin gene expression level compared to the standard expression level is indicative of disorder in phosphate metabolism, e.g., the kidney or bone system, or other tissues.

More particularly, the present invention relates to a method of diagnosing a pathological condition or a susceptibility to a pathological condition in a subject related to a disorder of phosphate metabolism comprising:

(a) determining the presence or absence of a mutation in the polynucleotide encoding phosphatonin; and (b) diagnosing a pathological condition or a susceptibility to a pathological condition based on the presence or absence of said mutation.

In another embodiment, the present invention relates to a method of diagnosing a pathological condition or a susceptibility to a pathological condition in a subject related to a disorder of phosphate metabolism comprising:

(a) determining the presence or amount of expression of a phosphatonin polypeptide or a mutant form thereof in a biological sample; and (b) diagnosing a pathological condition or a susceptibility to a pathological condition based on the presence or amount of expression of the polypeptide.

It is evident that the above-described nucleic acid probes and antibodies of the invention are preferably used for the mentioned methods.

The above described diagnosis method can also be employed to determine the status of said disorders. In connection with the present invention, the term "pathological condition" include the options that the gene, MRNA, protein or a transcription control element, e.g. promoter/enhancer sequence may bear a mutation, deletion or any other modifications which would affect the overall activity of the gene when compared to the wild-type normal gene product. Included in this term are post-translational modifications of the protein.

In a preferred embodiment of the method of the present invention said status in said subject is indicative of a certain form of the disorder in phosphate metabolism. Furthermore, it can be advantageous that in the method of the invention said status in said subject is determined in the embryonic status or in the newborn status, for example using aminocentesis.

The specific analysis of the status of (potential) disorder of phosphate metabolism at the embryonic, newborn or adult stage will provide further insights into, e.g., specific disease states associated with the respective stages. For example, it is expected that the etiology of, e.g., X-linked Hypophosphatemic Rickets (XHL) or Oncogenic Hypophosphatemic Osteomalacia (OHO) will be elucidated by applying the methods of the present invention. Upon the basis of this knowledge, new pharmaceutical active drugs will be developed and tested. The method of the invention can also be applied to a variety of animals, depending on the purpose of the investigation. Thus, in a preferred embodiment, the animal is a mouse. This embodiment is particularly useful for basic research to understand more clearly the functional interrelationship of different proteins which regulate the phosphate metabolism. In a further embodiment the animal is a human. In this embodiment, preferably diagnostic and therapeutic applications are envisaged.

In a preferred embodiment of the above-described method a further step comprising treating said newborn with a medicament to abolish or alleviate a disorder in phosphate metabolism is performed. Early diagnosis of a disorder in phosphate metabolism or susceptibility to this disorder is particularly advantageous and of considerable medical importance. This preferred embodiment can be used to diagnose the status in, e.g., the coronar villi, i.e. prior to the implantation of the embryo. Furthermore, the status can, with the method of the present invention, be diagnosed via amniocentesis. The early diagnosis of disorders in the phosphate uptake and/or reabsorption in accordance with all applications of the method of the invention allows treatment directly after birth before the onset of clinical symptoms.

X-linked rickets patients and tumour osteomalacia patients (prior to tumour resection, or if resection is not possible), are treated with high doses of calcitriol or 1,25 dihydroxy vitamin D3 (also known commercially as RocaltrolR and is available from Roche; see web site for detailed information on administration http://www.rochecanada.com/rocaltrol_pml_e.html, and oral phosphate supplements (dibasic sodium phosphate and/or phosphoric acid). Vitamin D analogs are also occasionally used (e.g., dihydrotachysterol), and urinary loss of phosphorus and calcium is reported to be further reduced by the additional use of thiazide diuretics such as hydrochlorothiazide and amiloride (Alon, Paediatrics 75 (1985), 754–763). For an extensive review of current treatments refer to (Carpenter, Pediatric Clinics of North America 44 (1997), 443–466). In children bones need to be reset by breaking deformed limbs (osteotomy), and the medications described above result in severe vomiting and diarrhea. Growth defects associated with familial rickets cannot be satisfactorily addressed using current treatments.

Replacing the above medications with phosphatonin and/or phosphatonin-peptide derivatives would correct the clinical symptoms and normalize the growth defects without the unpleasant side effects and surgical osteotomies.

In another preferred embodiment of the above-described methods, said methods further comprise introducing the functional and expressible phosphatonin gene into cells of a subject having a disorder or susceptibility to a disorder in phosphate metabolism. In this context and as used throughout this specification, "functional" phosphatonin gene means a gene wherein the encoded protein having part or all of the primary structural conformation of the phosphatonin polypeptide possessing the biological activity described above. The detection of an expression of a mutant form of phosphatonin would allow the conclusion that said expression is interrelated to the generation or maintenance of a disorder in phosphate metabolism. Accordingly, one alternative or additional step would be applied to reduce the expression level to low levels of the mutant phosphatonin or abolish the same. This can be done, for example, by at least partial elimination of the expression of the mutant gene by biological means, for example, by the use of ribozymes, antisense nucleic acid molecules or intracellular antibodies against the mutant forms of these proteins. Furthermore, pharmaceutical products may be developed that reduce the expression levels of the corresponding mutant genes.

Binding Activity

In a further aspect the present invention relates to a method for identifying a binding partner to a phosphatonin polypeptide comprising:

(a) contacting a phosphatonin polypeptide of the invention with a compound to be screened; and (b) determining whether the compound effects an activity of the polypeptide.

Phosphatonin polypeptides may be used to screen for proteins that bind to phosphatonin or for proteins to which phosphatonin binds. The binding of phosphatonin and the molecule may activate (agonist), increase, inhibit (antagonist), or decrease activity of the phosphatonin or the molecule bound. Examples of such molecules include antibodies, oligonucleotides, proteins (e.g., receptors), or small molecules.

Preferably, the molecule is closely related to the natural ligand of phosphatonin, e.g., a fragment of the ligand, or a natural substrate, a ligand, a structural or functional mimetic; see, e.g., Coligan, Current Protocols in Immunology 1(2) (1991); Chapter 5. Similarly, the molecule can be closely related to the natural receptor to which phosphatonin binds, or at least, a fragment of the receptor capable of being bound by phosphatonin (e.g., active site). In either case, the molecule can be rationally designed using known techniques; see also supra.

Preferably, the screening for these molecules involves producing appropriate cells which express phosphatonin, either as a secreted protein or on the cell membrane. Preferred cells include cells from mammals, yeast, Drosophila, or E. coli. Cells expressing phosphatonin (or cell membrane containing the expressed polypeptide) are then preferably contacted with a test compound potentially containing the molecule to observe binding, stimulation, or inhibition of activity of either phosphatonin or the molecule.

The assay may simply test binding of a candidate compound to phosphatonin, wherein binding is detected by a label, or in an assay involving competition with a labeled competitor. Further, the assay may test whether the candidate compound results in a signal generated by binding to phosphatonin.

Alternatively, the assay can be carried out using cell-free preparations, polypeptide/molecule affixed to a solid support, chemical libraries, or natural product mixtures. The assay may also simply comprise the steps of mixing a candidate compound with a solution containing phosphatonin, measuring phosphatonin/molecule activity or binding, and comparing the phosphatonin/molecule activity or binding to a standard.

Preferably, an ELISA assay can measure phosphatonin level or activity in a sample (e.g., biological sample) using a monoclonal or polyclonal antibody. The antibody can measure phosphatonin level or activity by either binding, directly or indirectly, to phosphatonin or by competing with phosphatonin for a substrate.

All of these above assays can be used as diagnostic or prognostic markers. The molecules discovered using these assays can be used to treat disease or to bring about a particular result in a patient (e.g., increase of phosphate level in the blood) by activating or inhibiting the phosphatonin/molecule. Moreover, the assays can discover agents which may inhibit or enhance the production of phosphatonin from suitably manipulated cells or tissues.

Therefore, the invention includes a method of identifying compounds which bind to phosphatonin comprising the steps of:

(a) incubating a candidate binding compound with phosphatonin; and (b) determining if binding has occurred.

Moreover, the invention includes a method of identifying agonists/antagonists comprising the steps of:

(a) incubating a candidate compound with phosphatonin;

(b) assaying a biological activity as described above, and (c) determining if a biological activity of phosphatonin has been altered.

As mentioned hereinbefore, the polynucleotides and polypeptides of the present invention provide a basis for the development of mimetic compounds that may be inhibitors or activators of phosphatonin or their encoding genes. It will be appreciated that the present invention also provides cell based screening methods that allow a high-throughput-screening (HTS) of compounds that may be candidates for such inhibitors and activators.

In a further embodiment, the present invention relates to a method of identifying and obtaining a drug candidate for therapy of disorders in phosphate metabolism comprising the steps of (a) contacting the polypeptide of the present invention or a cell expressing said polypeptide in the presence of components capable of providing a detectable signal in response to phosphate uptake, with said drug candidate to be screened under conditions to permit phosphate metabolism, and (b) detecting presence or absence of a signal or increase of the signal generated from phosphate metabolism, wherein the presence or increase of the signal is indicative for a putative drug.

For example, renal cell line CL8, human primary renal cells, or primary human osteoblast cells can be used to measure radioactive Na+-dependent phosphate uptake and/or vitamin D metabolism using methods described by, e.g., Rowe, 1996; supra.

Furthermore, poly A+ RNA or total RNA extracted from cells described in (a), and oligonucleotide primers complementary to sequence for phosphate transporter genes (NPTII etc), renal 24-hydroxylase, a α hydroxylase, PTH, or osteopontin to measure expression of these genes using, e.g., the polymerase chain reaction can be employed.

In addition, the measurement of mineralization of human primary osteoblast cells using von kossa stain is feasible. This method comprises, for example, growing human primary-osteoblasts (obtainable from Clonetics-Biowhitaker) to confluence using media supplements and conditions recommended by Clonetics;

for mineralization experiments supplementing the cells with phosphate donor β-glycerphosphate, and for controls hydrocortisone-11-hemisuccinate;

supplementing experimental cells with β-glycerphosphate and MEPE 25 ng/ml;

After 3 weeks in culture and serial changes of media staining the osteoblasts for bone mineralization using the Von-Kossa stain as described by Clonetics ($AgNO_3$; silver salt precipitation).

Furthermore, assays comprising the following measures can be employed:

Rat perfusion experiments and measuring effects of phosphatonin on renal phosphate uptake;

determining the expression of a range of relevant genes in human-renal cell line CL8 and the effects of MEPE supplementation, such as:
Na+ Phosphate transporters,
24 and 1-α hydroxylase,
Osteopontin and osteocalcin;

co-transfection system in COS cells with MEPE and PHEX;

Bio-assay studies using peptide fragments comprising at least one of the above described motifs. Hence, another detection method comprises the measurement of protein kinase C, casein kinase II, tyrosines kinase or other signal transduction pathways in cells exposed to phosphatonin and derivative peptides using contemporary techniques. Furthermore, the methods as described in the appended examples can be easily adapted to the above-described screening methods.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating phosphatonin polypeptides or other components in the phosphate metabolism. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into a cell or otherwise applied to the transgenic animal. The cell or tissue that may be employed in the method of the invention preferably is a host cell, mammalian cell or non-human transgenic animal of the invention described in the embodiments hereinbefore.

If a sample containing a compound or a plurality of compounds is identified in the method of the invention, then it is either possible to isolate the compound from the original sample identified as containing the compound capable of suppressing or activating phosphatonin, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879–880; Hupp, Cell 83 (1995), 237–245; Gibbs, Cell 79 (1994), 193–198 and references cited supra). Furthermore, genes encoding a putative regulator of phosphatonin protein and/or which exert their effects up- or downstream the phosphatonin protein of the invention may be identified using, for example, insertion mutagenesis using, for example, gene targeting vectors known in the art (see, e.g., pShooter plasmid series that target expression to the nucleus, mitochondria, or cytoplasm pEF/myc/nuc, pCMV/myc/nuc, pEF/myc/mito, pCMV/myc/mito, pEF/myc/cyto, pCMV/myc/cyto, or pDISPLAY expression vector that targets recombinant proteins to the surface of mammalian cells. All the vectors are obtainable from Invitrogen (http://www.invitrogen.com/)).

Determining whether a compound is capable of suppressing or activating phosphatonin proteins can be done, for example, by monitoring Na+-dependent phosphate uptake or bone mineralization; see supra. It can further be done by monitoring the phenotypic characteristics of the cell of the invention contacted with the compounds and compare it to that of wild-type cells. In an additional embodiment, said characteristics may be compared to that of a cell contacted with a compound which is either known to be capable or incapable of suppressing or activating phosphatonin proteins.

Once the described compound has been identified and obtained, it is preferably provided in a therapeutically acceptable form. Thus, the present invention also relates to a method of producing a therapeutic agent comprising the steps of the methods of the invention described above; and (i) synthesizing the compound obtained or identified in step (b) of a method of the invention or an analog or derivative thereof in an amount sufficient to provide said agent in a therapeutically effective amount to a patient; and/or (ii) combining the compound obtained or identified in step (b) of a method of the invention or an analog or derivative thereof with a pharmaceutically acceptable carrier.

Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be synthesized and tested for their effects according to methods known in the art; see also supra and infra.

In summary, the present invention provides methods for identifying compounds which are capable of modulating phosphate metabolism due to their direct or indirect activation or phosphatonin. Accordingly compounds identified in accordance with the method of the present invention to be inhibitors and activators, respectively, of phosphatonin activity are also within the scope of the present invention.

As is evident from the above, the present invention generally relates to compositions comprising at least one of the aforementioned polynucleotides, nucleic acid molecules, vectors, proteins, regulatory sequences, recombinant DNA molecules, antibodies or compounds. Preferably, said composition comprises ingredients such as buffers, cryoprotectants etc. which are not naturally associated with the mentioned components of the invention and render the same suitable for a particular use.

Advantageously, said composition is for use as a medicament, a diagnostic means or a kit. Pharmaceutical compositions are described in more detail in Examples 6 and 7. In particular, bioactive fragments as described above may be useful as a medicament in the treatment of a disorder of phosphate metabolism such as X-linked rickets and osteomalacia as well as other diseases of bone mineral metabolism. There is further provided phosphatonin and PHEX metallopeptidase as a combined preparation for simultaneous, separate or sequential use as a medicament. In this way, the PHEX metallopeptidase may be used to cleave phosphatonin so as to produce active phosphatonin fragments which may be used for the treatment of disorders of phosphate metabolism as discussed herein. Whilst all of these diseases are particularly important in humans, other mammals may also be treated in accordance with the invention.

The present invention has provided for the first time phosphatonin in a substantially isolated or purified form which is suitably free of contaminants. Native phosphatonin and native fragments of phosphatonin, which are free of contaminants such as SDS and/or other interfering proteins are capable of regulating phosphate metabolism and of providing active ingredients in pharmaceutical compositions for the treatment of diseases associated with disorders of phosphate metabolism.

Hence, the present invention relates to the use of a phosphatonin polypeptide of the present invention or a DNA encoding and capable expressing said polypeptide, the antibody, the activator/agonist, inhibitor/antagonist or binding partner of the present invention, for the preparation of a medicament for treatment of a disorder of phosphate metabolism.

In particular, the present invention relates to the use of a phosphatonin polypeptide having phosphatonin activity or a DNA encoding and capable expressing said polypeptide, the antibody, the activator/agonist or binding partner of the invention whose presence in the cell leads to phosphatonin activity, for the preparation of a medicament for the treatment of hyperphosphatemia, preferably for the treatment of renal osteodystrophy, hyperphosphatemia in renal dialysis/pre-dialysis, secondary hyperparathyrodism or osteitis fibrosa cystica.

In another embodiment, the present invention relates to the use of a phosphatonin polypeptide having anti-phosphatonin activity or a DNA encoding and capable expressing said polypeptide, the antibody of the invention, the nucleic acid molecule or the inhibitor/antagonist of the present invention, for the preparation of a medicament for the treatment of hypophosphatemia, preferably for the preparation of a medicament for the treatment of X-linked hypophosphatemic rickets, hereditary hypophosphatemic rickets with hypercalcuria (HHRH), hypomineralized bone lesions, stunted growth in juveniles, oncogenic hypophosphatemic osteomalacia, renal phosphate leakage, renal osteodystrophy, osteoporosis, vitamin D resistant rickets, end organ resistance, renal Fanconi syndrome, autosomal rickets, Paget's disease, kidney failure, renal tubular acidosis, cystic fibrosis or sprue.

In a preferred embodiment of the present invention, the phosphatonin polypeptide having anti-phosphatonin activity or a DNA encoding and capable expressing said polypeptide, the antibody of the invention, the nucleic acid molecule of the invention or the inhibitor/antagonist of the invention are used for the manufacture of a medicament for the treatment of a bone mineral loss disorder.

In another preferred embodiment, the present invention relates to the use of a phosphatoninpolypeptide and PHEX metallopeptidase for the manufacture of a combined preparation for simultaneous, separate or sequential use for the treatment of a disorder of phosphate metabolism.

The above-mentioned uses and methods are described in more detail in Example 6.

In another embodiment, the present invention relates to the use of a transformed osteoblast or bone cell line capable of phosphatonin overexpression for the production and isolation of phosphatonin.

The following examples are put forth so as to provide those skilled in the art with a complete disclosure and description of how to carry out various aspects of the invention and are not intended to limit the scope of what the inventors regard as their invention, nor are they intended to represent or imply that the experiments below are all of or the only experiments performed. Efforts have been made to ensure accuracy with respect to numbers used (e.g., amounts, temperatures, etc.) but some experimental error and deviation should be accounted for. Unless indicated otherwise parts are parts by weight, molecular weight is weight average molecular weight and temperature is in degrees centigrade.

EXAMPLE 1

Purification of Phosphatonin from Tumor

A mesenchymal tumor with phosphaturic expression was removed from a patient and the following samples taken:

A: Sample of pure tumor tissue, size of two large peas, was placed into a 2 ml vial containing DMEM Eagles/10%/oFCS/glutamine/antibiotic antimycotic Gibco-BRL.

B: Sample of sub-dura tumor approximately the same size possibly smaller. Placed in same media as A.

C: Sample of abnormal dura: tough white material: Placed in same media as A.

D: Sample of tumor fluid.

Processing of Samples:

Day 1:

The samples were each cut into small 0.5 cm cubes using a sterile scalpel. Half of each sample was placed into a cryotube and frozen down in N2(1) immediately. The fluid surrounding the tissue (DMEM/10% FCS etc.), was also collected and frozen down. The other half of each sample was added to DMEM Eagles/10% FCS/glutamine/antimycotic antibiotic supplemented with collagenase Al 0.2 mg/ml (~15 ml), and left at 37° C. overnight.

Day 2:

1. After overnight incubation in serum supplemented DMEM, the cells appeared to be predominantly RBC's and very few adherent cells were observed. The cells were spun down at room temp and the supernatants collected and immediately frozen down (~15 ml).

2. The pellets were then resuspended in 10 ml of DMEM Eagles supplemented with antibiotic/antimycotic (medium flasks), and then incubated for a further 8 h 10 min.

3. The serum-free supernatants were collected as described in 1 (~10 ml), and the cells were resuspended in DMEM EAGs with 10% FCS etc., (~15 ml), and incubation continued. The supernatants were stored at −80° C.

Day 6:
1. After incubation from Day 2, cells were spun down as described for I of Day 2. 10% FCS samples were collected and frozen.
2. Pellets were resuspended in serum free DMEM (10 ml), as for Day 2 and this time left for four hours.
3. Same as for 3 of Day 2.

Day7:
1. The subdura and tumor culture in particular, had developed innumerable foci containing clumps of cells which appeared attached to the plastic of the tissue culture plates. Underneath these polyp like protuberances was a monolayer of fibroblast like cells which spread out radially from underneath the tumor like structures. This layer of cells appeared to act as a matrix to anchor the polyp like tumors. None of this was seen in the dura sample, which appeared to lack cells at this stage, and contained fibrous like matted structures.
2. Cultures were spun down, and the supernatants collected (10% FCS). The pellets were then placed to one side.
3. The plates were then incubated with 10 ml of trypsin EDTA soln Gibco/BRL 1/10 dilution in PBS for −15 min. Plates were then tapped vigorously and 5 ml of FCS added.
4. The resuspended cells were then added to the pellets obtained in 2, resuspended and spun down. The supernatant was discarded.
5. Cells were then plated out in 18 ml of 10% FCS DMEM Eagles medium with glutamine and antibiotic antimycotic supplements (large flakes were used.)
6. Finally cells were incubated at 37° C. in $CO_2$ atmosphere.

Day 9:
1. Tumor cells and to some extent the subdura cells appeared as innumerable clumps of cells, and appeared to have the same morphology as the cells prior to trypsin treatment. Some of the clumps were quite large, and visible to the naked eye.
2. The serum supplemented media was collected and stored down. Large flasks were used and 18 ml of media per flask added (DMEM 10% FCS antimycotic/antibiotic/glutamine).

Day 13:
1. Cells were frozen down (−15 ml), and stored in falcons as 10% FCS DMEM conditioned media.
2. Cells resuspended in serum free DMEM Eags (−11 ml) 11.10 am, and left for 6 h at 37° C. ($CO_2$ incubator).
3. Cells were then spun down and the supernatants collected (serum free control media). 10% FCS DMEM EAG was then added to the remaining cells.

Day 16:
The above process was repeated and Tumor Conditioned Medium (TCM) collected over several weeks. Alternatively, TCM may be collected from Saos-2 cells (ECACC 89050205) or U-2 OS cells (ATCC HTB-96).

Figure 1B:
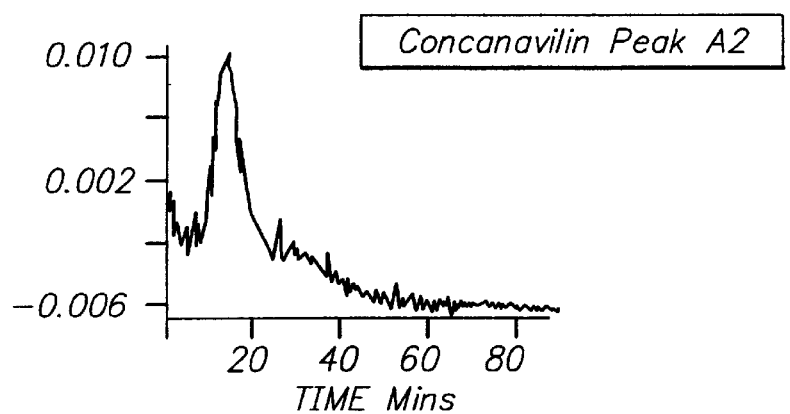
FIG. 1.

Purification of Phosphatonin:
Concanavalin A Sepharose Affinity Chromatography:
1. 3 ml of TCM was adjusted with IM sodium phosphate pH 7.2 and SM NaCl to give a final concentration of 0.06M Sodium phosphate pH 7.2 and 0.5M NaCl plus 0.01% sodium azide.
2. Con A Sepharose (Pharmacia Code No: 17–0440–01), arrived in 20% Ethanol, and this was first washed with several column volumes of water, and then equilibrated in the running buffer. A small C10/10 column (Pharmacia code No: C10/10 id 10 mm), was packed with Con A to a height of 5.5 cm (approx. volume 4.3 to 5.0 ml). Equilibration was carried out at max flow rate of 0.5 ml/min.
3. The sample (adjusted to pH 7.2 sodium phosphate/0.5M NaCl/0.01% sodium azide), was then added to the column by gravity feed, and reloaded three times. The color of the sample enabled visualization of the passage through the column. Unbound material was then collected and stored for future reference.
4. Waters LC system was then connected and the sample was washed with several column volumes of loading buffer.
5. After loading and washing, elution was carried out using sodium phosphate buffer 60 mM pH 7.2/0.5M NaCl/0.5M α-methyl-D-glucopyranoside/0.01% azide buffer. See FIG. 1a. A single peak was detected and this was collected.
6. The column was then run to base line approximately 40 ml max, and then left overnight.
7. After overnight incubation in methyl glycoside buffer, a second peak was eluted (see FIG. 1b), which peaked at −5 ml.
8. The second peak was collected and dialyzed against 0.05M acetic acid, and then lyophilized. Both Concanavalin peaks Al (low affinity), and concanavalin A2 (high affinity), are potent at inhibiting Na+ dependent phosphate co-transport and vitamin D metabolism in a human renal cell line (CL8). The high affinity fraction, the human renal cell line (CL8), and the conditions used for assay are described in Rowe et al 1996. A further suitable known renal cell line for this assay is the OK cell line deposited as ECACC 91021202.

Cation Exchange Chromatography using HiTrap SP Cation Exchange 1 ml Column (Code No 17–1151–01; Pharmacia):
1. The lyophilized protein was then re-dissolved in 0.05M ammonium acetate pH 5 and the applied to an equilibrated 1 ml HiTrap SP sepharose cation exchange column.
2. The column was equilibrated prior to sample addition by washing with water, and then 5 volumes of start buffer (0.02 M ammonium acetate pH 5).
3. Sample was eluted using the following protocol;

| Num | Time Min | Flow rate ml/min | % $NH_4$ acetate pH 5 | % $NH_4$ acetate/ 0.5 M NaCl pH 5 |
| --- | --- | --- | --- | --- |
| 1 |    | 0.5 | 100 | 0 |
| 2 | 15 | 0.5 | 25  | 75 |
| 3 | 20 | 0.5 | 0   | 100 |
| 4 | 25 | 0.5 | 0   | 100 |
| 5 | 35 | 0.5 | 100 | 0 |
| 6 | 50 | 0.5 | 100 | 0 |

Figure 2:
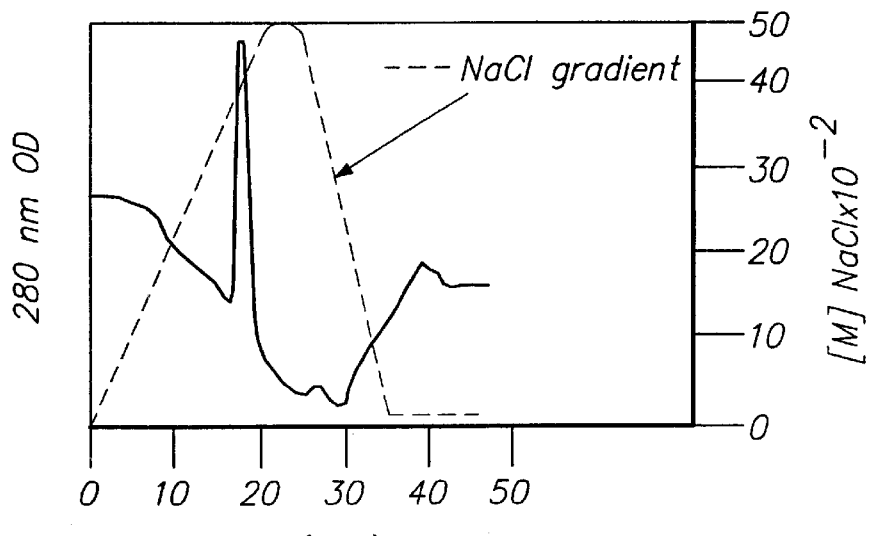
FIG. 2: Cation exchange chromatogram of fractions from the concanavalin A column.
Figure 3:
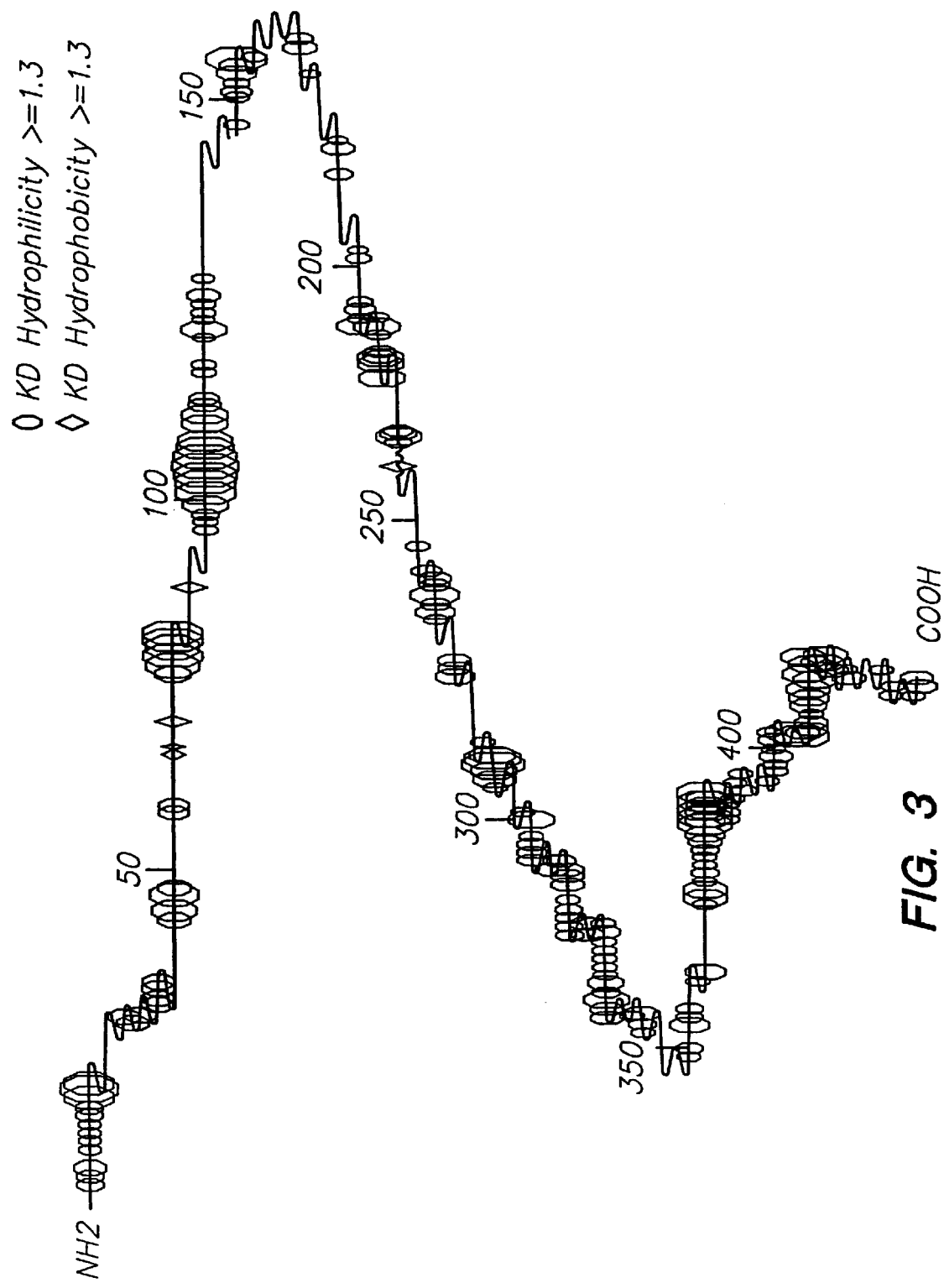
FIG. 3: Computer prediction of hydrophilicity and hydrophobicity of phosphatonin.

A Single sharp peak was obtained, and the sample was then dialyzed against 0.05M acetic acid and lyophilized; see FIG. 2.

After resuspending in 10 mM phosphate buffer pH 7.2 20 μl, aliquots were resuspended in SDS-PAGE sample buffer (to a final concentration=125 mM TRIS-HCL pH6; 2.5% glycerol; 0.5% w/v SDS: 5% β-mercaptoethanol; 0.01% bromophenol blue), boiled (5 mins), cooled and then run on an SDS PAGE gel 12.5% (see chromatogram), and a double band of 55 kD was resolved (see Rowe et al 1996). Both the Concanavalin A and cation bands also have an aggregated form. All fractions including the tumor conditioned media were potent at inhibiting Na+ dependent phosphate co-transport in a human renal cell line (1/1000 diln), and also altered vitamin D metabolism. For a full description of the methods used to measure phosphate transport and vitamin D metabolism see Rowe et al 1996. All purification modalities were carried out on a waters HPLC/FPLC system programmed by computer-millennium software. The most active fraction was the concanavalin Al fraction from OHO tumor. Anti pre-operation antisera was used to screen the immobilized purified fraction. The fraction is also potent at inhibiting NaPi, and affects vitamin D metabolism in a human renal cell line (CL8).

EXAMPLE 2

Screening of Tumor Conditioned-medium (TCM), and Purified Fractions with Pre/Post- Operation Antisera; Plus Glycoprotein Screen Pre-operation and post-operation antisera from a patient has been described previously in Rowe et al 1996. Only pre-operation antisera detected the purified fractions and hormone in TCM in which Western and glycoprotein detection of TCM and purified fractions was achieved using enhanced chemiluminescence. Protein markers were biotinylated, and tagged with streptavidin peroxidase conjugate. The arrows show the aggregate and active glycoprotein. Post-operation antisera and rabbit pre-immune sera did not detect any of the fractions. Also, only those tumors secreting phosphaturic factor were positive. Media and skin controls were negative. A distinct feature of the Con A1, Con A2 and CA1 samples was their potent ability to inhibit NaPi, and alter vitamin D metabolism in a human renal cell line (CL8). All the purified fractions have a tendency to aggregate into a lower mobility form on SDS-PAGE. Also, the purified fractions and TCM active fractions are heavily glycosylated. The extent of glycosylation was confirmed by periodate oxidation of immobilized proteins on PVDF membranes followed by biotinylation of carbohydrate moieties. These were then screened with streptavidin conjugated to horse radish peroxidase and enhanced chemiluminescence. The active form (inhibits NaPi etc.), is associated with the 58 to 60 kDa fraction. An additional and powerful way of purifying the protein to homogeneity is the use of a neutral pH 7 SDS-PAGE system using a 4–12% Bis-Tris Gel with MOPS running buffer. Pre-caste gels can be purchased from Novex.

EXAMPLE 3

SDS-PAGE at Neutral pH using 4–12% Polyacrylamide Gradient and Bis-Tris Gel with MOPS Running Buffer (Nu-PAGE System from NOVEX): Reduced Mobility of Hormone On this system a fraction of the glycosylated hormone has a reduced mobility, and runs at ~200 kDa. The lower molecular weight form is also visible at 58/60 kDa. Appearance of the ~200 kDa protein may be due to the isoelectric point of the protein (different charge at neutral pH), and the interaction of carbohydrate moiety with the gel matrix. Also, increased efficiency of electro-blotting of high molecular weight components occurs due to the low % acrylamide (4–12% gradient), at the top of the gradient gel. Running fractions through this system increases the purity and homogeneity of the molecule. A Western blot using this system and including the following samples (pre-operation antiserum was used to screen the blots using enhanced chemiluminescence detection): 1. protein markers; 2. intracranial tumor cell line OHO; 3. cells from sub-dura adjacent to tumor; 4. cells from dura adjacent to sub-dura; 5. HTB6 cell line; 6. Saos-2 cell line; 7. defined medium control; 8. Skin fibroblast control; 9. Linear sebaceous naevus polyp tumor demonstrated that Naevus polyp tumor showed a specific phosphaturic band at ~200 kDa on SDS-PAGE Neutral gels.

EXAMPLE 4

Cloning and Sequencing of Phosphatonin

1. Library Construction:

A tumor derived from a patient described in an earlier publication (BD, Rowe et al., 1996), was sectioned and mRNA extracted using standard techniques. The mRNA was copied using reverse transcriptase to generate a cDNA population that was then subsequently subcloned into a bacteriophage vector λ-ZAP II uni (vector purchased from Stratagene Ltd., Unit 140, Cambridge Science Park, Milton Road, Cambridge, CB4 4GF United Kingdom). The cloning was uni-directional and the 5' end of the gene was adjacent to the T3 promoter and abutted an EcoRI site. The 3' end of the cDNA's abutted an Xho-1 site upstream of a bacterial T7 promoter. Briefly, resected tumour from patient BD was cut into 1 mm blocks and poly A+ RNA extracted directly using Streptavidin-Magnesphere paramagnetic particle technology (PolyATract® system Promega). The purified mRNA was then used to generate a cDNA template using the cDNA synthesis kit from Stratagene. Linker primers were added to the CDNA to generate a 5' EcoRI compatible CDNA end, and an XhoI compatible 3' cDNA end, to facilitate forced orientation cloning into λZAP II uni bacteriophage vector. Recombinant bacteriophages were plated out and amplified on E. coli XL1-Blue mrf'. Total primary clones numbered 800000 with 6% wild type representation.

2. Screening with Pre-operative Antisera:

The cDNA bacteriophage library was plated out of NZY agar plates and the β-galactosidase operon induced using IPTG. Expressed fusion proteins were then transferred to hybond-C membranes (Amersham) and the membranes were then screened with pre-operation antisera from the patient. The antisera used has been described (Rowe et al., 1996). Prior to use the antisera was extensively pre-absorbed with E. coli lysate, and whole blood to reduce signal to noise. Rabbit antisera raised against patient BD pre-operation serum (Rowe, Bone 18 (1996), 159–169), was extensively pre-absorbed with normal human serum and E. coli lysate in order to remove E. coli antibodies and background human-serum derived antibodies. Briefly, five 80 mm diameter nitrocellulose filters were added to whole E. coli lysate (Stratagene), and a second set of five filters were soaked with normal human serum (10 ml). The impregnated filters were each incubated for 10 min at room temperature in sequence with 250 ml of 1:1000 diluted anti rabbit pre-operation antisera in 1% BSA; 20 mM Tris-HCl (pH7.5), 150 mM NaCl (TBS); 0.02% NaN$_3$. The preabsorbed pre-operation antisera (pre-Aanti-op) was then used to screen the cDNA library. Bacteriophage λZAP II uni OHO cDNA-clones were plated out on E. coli XL1-Blue mrf' and incubated for 3 hours at 37° C. Hybond N$^+$ filters preincubated with 10 mM IPTG were then placed on top of the developing plaques and incubated a further 3 h at 42° C. Filters were then removed and washed with TBS supplemented with Tween 20 (TBST), and then blocked with 1% BSA in TBS with 0.02% NaN3 overnight at 4° C. Pre-Aanti-op was then added to the blocked filters and left for 1 h at room temperature. Subsequent washes of the filters and incubation with goat-anti-rabbit alkaline phosphatase conjugate, followed by visualization using 5-bromo-4- chloro-3-indolyl phosphate/nitroblue tetrazolium was as described by Stratagenes picoblue™ immunoscreening kit. After screening ~600,000 clones, nine positives were selected and purified by secondary and tertiary screening. The bacteriophage clones were rescued as phagemids using ExAssist helper phage and cloned into *E. coli* SOLR cells. ExAssist helper phage and SOLR cells were purchased from Stratagene Ltd., Suite 140, Cambridge Science Park, Milton Road, Cambridge, CB4 4GF, United Kingdom.

3. Sequencing Clone:

Phagemids were prepared and the DNA sequenced. All nine clones were sequenced. Positive bacteriophage-plaques were removed from agarose plates after tertiary screening with a sterile hollow quill. The agarose plugs containing the lytic plaques was then added to 0.5 ml of SM buffer supplemented with 0.02% chloroform, and left at 4° C. overnight. Rescue and transformation of bacteriophage clones to BSCPT SKII- phagemids was carried out using ExAssist phage as described by Stratagene. The host cells for the purified phagemid were *E. coli* SOLR cells. Plasmid DNA was then prepared using standard techniques (Rowe, Nucleic Acids Res. 22 (1994), 5134–5136), and sequenced using ABI fluorescent automated sequencing and standard vector specific primers. Six of the clones were overlapping and in fiame with the bacterial β-galactosidase promoter to give contiguous/overlapping epitopes and expressed proteins with identical overlapping DNA sequences. The longest sequenced clone encompassed the cDNA sequences of the five others and is shown in FIG. 8. This sequence (amino acid/cDNA) is a complete sequence for phosphatonin. There are 430 amino acid residues cloned (SEQ ID NO: 2) and 1655 bp of DNA sequence (SEQ ID NO: 1). Secondary structure prediction indicates a highly hydrophilic protein with glycosylation at the COOH end, and the presence of a cell attachment tripeptide at the amino end (RGD), see FIG. 8. The protein is also highly antigenic with a number of major helical domains (FIG. 10). Extensive screening of all available databases using BLAST has not-revealed any statistically relevant homology to known genes or protein sequences.

4. Purification of Recombinant Human Phosphatonin:

The isolated cDNA clone is represented as rescued phagemids in Bscpt SKII—vector (Stratagene vector), and contained within SOLR *E. coli* host cells. Low level fusion protein expression via induction of the β-galactosidase promoter by IPTG has been achieved. The phosphatonin clone fusion-product reacts with pre-operation antisera on western blots. Increased expression and bioactivity of the fusion proteins can be achieved by sub-cloning into the pCAL-n-EK vector (Stratagene vector) (see below). The construct containing human phosphatonin is contained in *E. coli* (BL21 (DE3) pLysS) cells (purchased from Stratagene). IPTG induction of fusion protein is much higher, and essentially pure protein can be obtained by calmodulin affinity-chromatography of cell lysates. Recombinant phosphatonin with filsion-tag binds to the calmodulin resin in the presence of $Ca^{2+}$. Phosphatonin fusion protein is then released after washing with EGTA. The small microbial fusion-tag is removed by treatment with enterokinase, leaving pure human phosphatonin.

4a. Subcloning Phosphatonin into pCAL-n-EK Vector

The entire deduced cDNA coding sequence (deduced from the largest cDNA clone pOHO11.1), of phosphatonin (MEPE) was subcloned into the prokaryote expression vector plasmid pCAL-n-EK (Stratagene vector), and the construct transformed into *E. coli* BL21 (DE3) pLysS and *E. coli* XL1-Blue mrf' respectively (strains obtained from Stratagene). The method of ligation independent cloning (LIC) was used as described by Stratagene Affinity™ cloning and protein purification kit (cat No: #214405 and #214407). Two primers were designed from the phosphatonin sequence 5' and 3' end respectively with additional overhang linker sequence as follows (bold sequence represents linker):

```
Forward                              (SEQ ID NO:8)
5' GACGACGACAAG.GTGAATAAAGAATATAGTATCAGTAA 3'
   Linker Reverse                              (SEQ ID NO:9)
5' GGAACAAGACCCGT.CTAGTCACCATCGCTCTCACT 3'
   Linker
```

Figure 14:
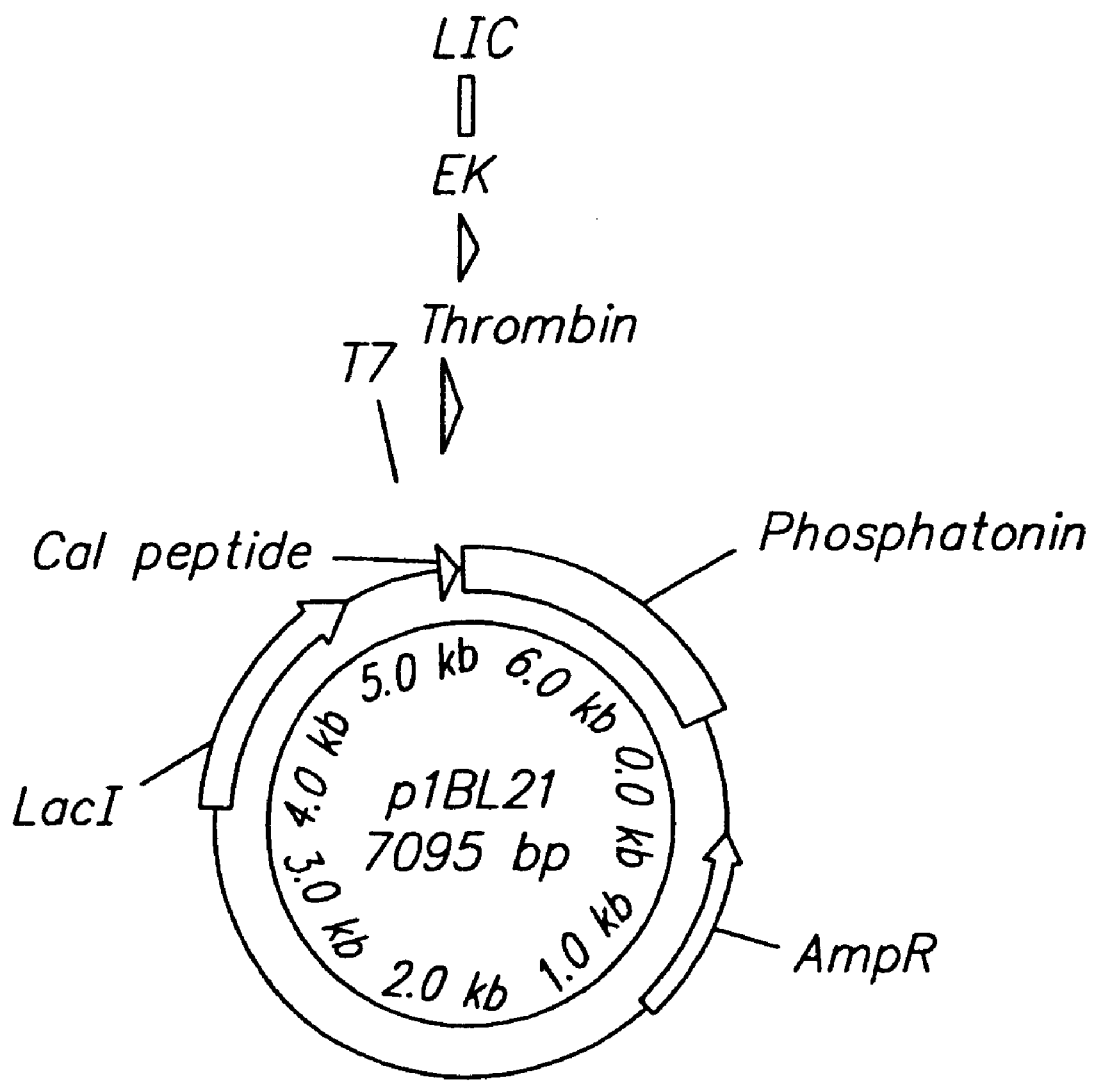
FIG. 14: p1BL21 and also p6XL1 recombinant plasmids containing phosphatonin fusion construct. LacI: (lac promoter); LIC: (Ligation independent cloning sequence); EK: Enterokinase cleavage site; Thrombin (thrombin target sequence); Amp: Ampicillin resistance: Cal peptide (calmodulin peptide sequence); Phosphatonin (phosphatonin coding sequence).

PCR amplification of phosphatonin includes DNA sequence coding for the first valine residue to the stop codon of phosphatonin (see FIG. 8), plus linker sequence. A 5' overhang of the linker sequence is then generated by treating the PCR fragment with Pfu polymerase and dATP. Induction of fusion protein is carried by growing the cells and adding IPTG. The PCR conditions were as follows. Predenaturation; 95° C. 3 min, followed by 20 cycles of Denaturation; 95° C. 45 sec, Annealing 59° C. 60 sec, 72° C. 2 min, and then 72° C. 7 min final extension; followed by cooling 4° C. A Perkin Elmer 9600 thernocycler was programmed to carry out the PCR, and the following PCR buffer (PB), was used: 10 mM Tris-HCl pH 8, 50 mM KCl, 1 $\mu$M primers, 200 $\mu$M dNTP's. PB buffer was supplemented with 2 mM $MgCl_2$. For ligation independent cloning (LIC), the amplified product was then treated with pfu polymerase and dATP as described by Stratagene, and then directly annealed to linearized pCAL-n-EK plasmid vector with complementary linker overhangs. The construct was then transformed into competent *E. coli* XL1-blue mrf' cells, and competent *E. coli* BL21 (DE3) Clones were then selected on ampicillin plates, and plasmids prepared and sequenced. A summary of the vector and fusion construct is shown in FIG. 14. High copy number plasmid is achieved with *E. coli* XL1-blue mrf' host, and high recombinant protein expression is obtained with *E. coli* BL21 (DE3).

4b. Purifying Phosphatonin by Calmodulin Affinity Resin

The method as described by Stratagene (cat~214405), can be used. Sequence upstream from the phosphatonin specific residues will contain a calmodulin binding sequence. Calmodulin resin is added to the crude cell lysate in the presence of calcium, and the protein allowed to bind. The slurry is then washed with calcium containing buffer, and the phosphatonin fusion protein eluted by addition of EGTA 2 mM in a Tris buffer (50 mM Tris-HCl pH 8). Removal of the calmodulin binding protein tag is then accomplished by digestion with site-specific protease EK, leaving pure recombinant human phosphatonin. Preferably, the method may be performed as follows (See table below for buffer compositions):

1. Cells are cultured and induced as described by the Stratagene protocol for pCAL-n-EK vectors (Cat No: #214405), using BL23 (DE3) *E. coli* host cells comprising plasmid p1BL21; see FIG. 14.
2. Protein lysate is also prepared as described by the Stratagene protocol but using CCBB-II as resuspension buffer (resuspend cell pellet from 500 ml in 10 ml of CCBB-II). It is essential to sonicate in 30 sec pulses followed by 4 min cooling with ice. Tubes containing cells are kept on ice during sonication.
3. After sonication cells are spun at 10000 g and the supernatant decanted. Most of the recombinant MEPE remains in the supematant (protein-lysate).

4. The protein-lysate is then concentrated by using a VIVASCIENCE VIVASPIN (Cat No: VS1521 called 30,000 MWCO PES) concentrator with a 30000 molecular weight cut off. Approximately 8 ml of supernatant from 500 ml of cells concentrates down to 3.2 ml (X2.5 conc.). Further concentration is not advisable.
5. For protein-lysate prepared from 190–200 ml of cells (~1.3 ml of equivalent protein-lysate), 1 ml of equilibrated calmodulin resin is then added (equilibrate resin as described by Stratagene using CCBB-II buffer).
6. The suspension is rotated overnight at 4° C.
7. The suspension is spun down (~3000 rpm on eppendorf centrifuge for 2 min), the supernatant removed and the resin resuspended in 1 ml of CCBB-II buffer.
8. The resin is spun down again and the first wash removed. This is repeated twice more (total of three washes in CCBB-II).
9. It is then washed once with WB-III; note non of the buffers including the final wash buffer contain detergents. The cells used for bio-assay are extremely sensitive to detergents even in trace amounts. WB-III is the same as CCBB-II but without protease inhibitors.
10. Non-specific proteins are eluted by washing with buffer EB-I twice (1 ml).
11. MEPE is eluted with EB-II 2–3 times (1 ml).
12. Protein is concentrated using a flowgen 10K microsep concentrator at 4° C. Generally 3 ml of MEPE eluate can be concentrated down to ~170 μl in 2 hr.
13. After running samples on an SDS-PAGE gel to assess purity and quantity multiple aliquots are made and frozen at –80° C. Repeated freeze thaw is avoided.

Buffers:

| Component | CCBB-II | WBIII | EBI | EBII |
|---|---|---|---|---|
| TrisOBuffer pH 8 | 50 mM | 50 mM | 50 mM | 50 mM |
| NaCl | 300 mM | 300 mM | 150 mM | 1 M |
| MgAcetate | 1 mM | 0 | 0 | 0 |
| Imidazole | 1 mM | 0 | 0 | 0 |
| CaCl2 | 2 mM | 2 mM | 0 | 0 |
| Protease Inhibitors w/o EDTA | YES | No | No | No |
| EGTA | 0 | 0 | 4 mM | 4 mM |

Protease inhibitor tablets were added 1 per 10 ml when used (Boehringer Mannheim), protease inhibitor w/o EDTA (Cat No: 1836 170). A final elution with 1M NaCl, EGTA (4 MM) buffer results in >95% purity of phosphatonin.

EXAMPLE 5

Structure of Phosphatonin

Figure 9:
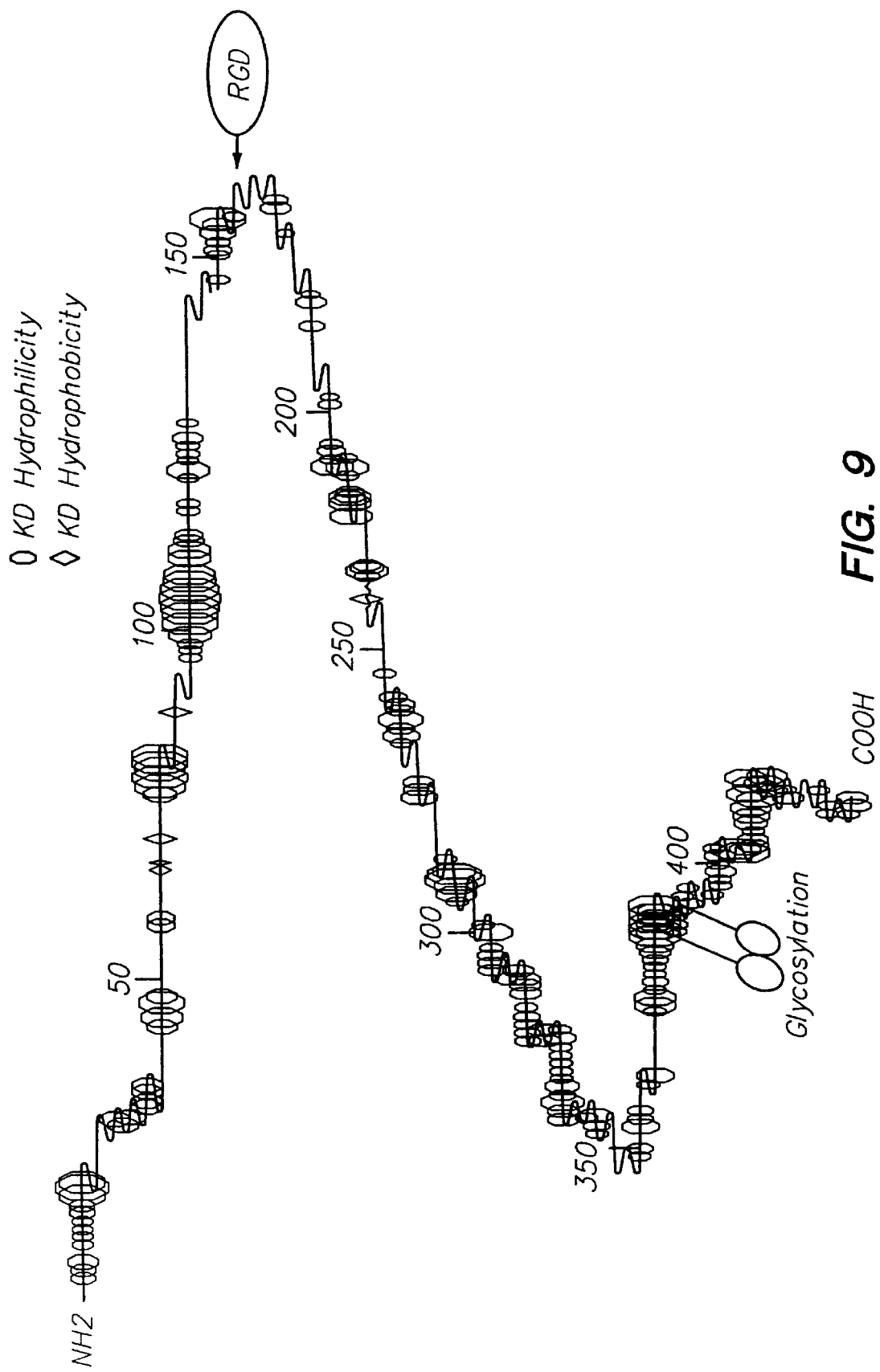
FIG. 9: GCG-peptide-structure secondary structure prediction for MEPE. The primary amino acid backbone is shown as the central line with curves indicating regions of predicted turn. Hydrophilicity/hydrophobicity regions are represented as ellipsoids and diamonds respectively and the RGD motif is indicated. The N-glycosylation sites are represented as ellipsoids on stalks (C-terminus), and alpha helix by undulating regions on the primary backbone.
Figure 10B:
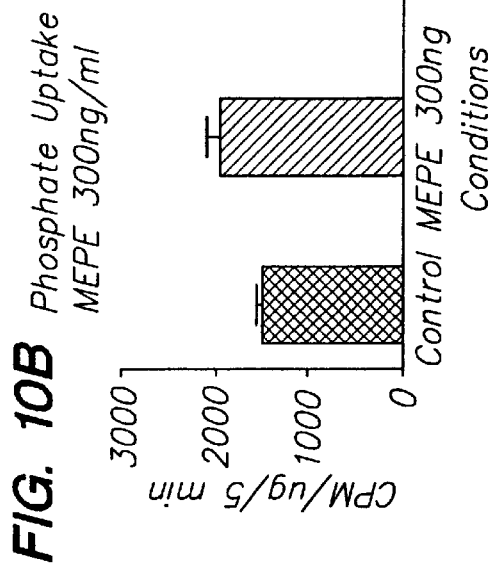
FIG. 10: Bar graphs showing phosphate-uptake in the presence of differing amounts of MEPE: A. 92 ng/ml, B. 300 ng/ml, C. 500 ng/ml, and D. 1000 ng/ml. Choline boxes refer to control Na- independent results with NaCl replaced with choline chloride. Error bars are SEM, and P values for the difference between MEPE and control in C and D are <0.001. In experiment A (92 ng/ml) P<0.05, and in B (300 ng/ml P, 0.01). N values for A and B are 4, and for C and D 5 and 6 respectively. Anova followed by Newman-Keuls Multiple Comparison Test was used.
Figure 10D:
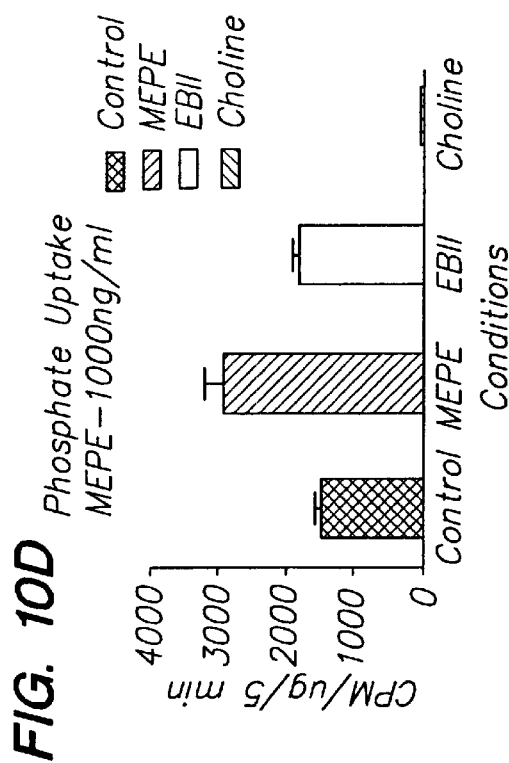
Figure 10A:
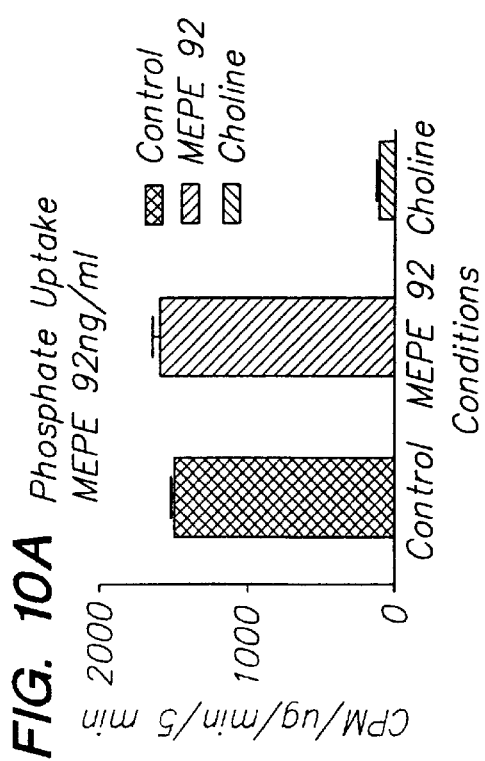
Figure 10C:
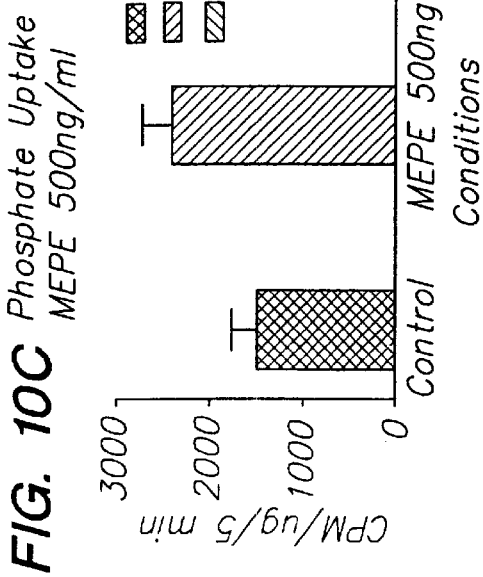
Figure 11:
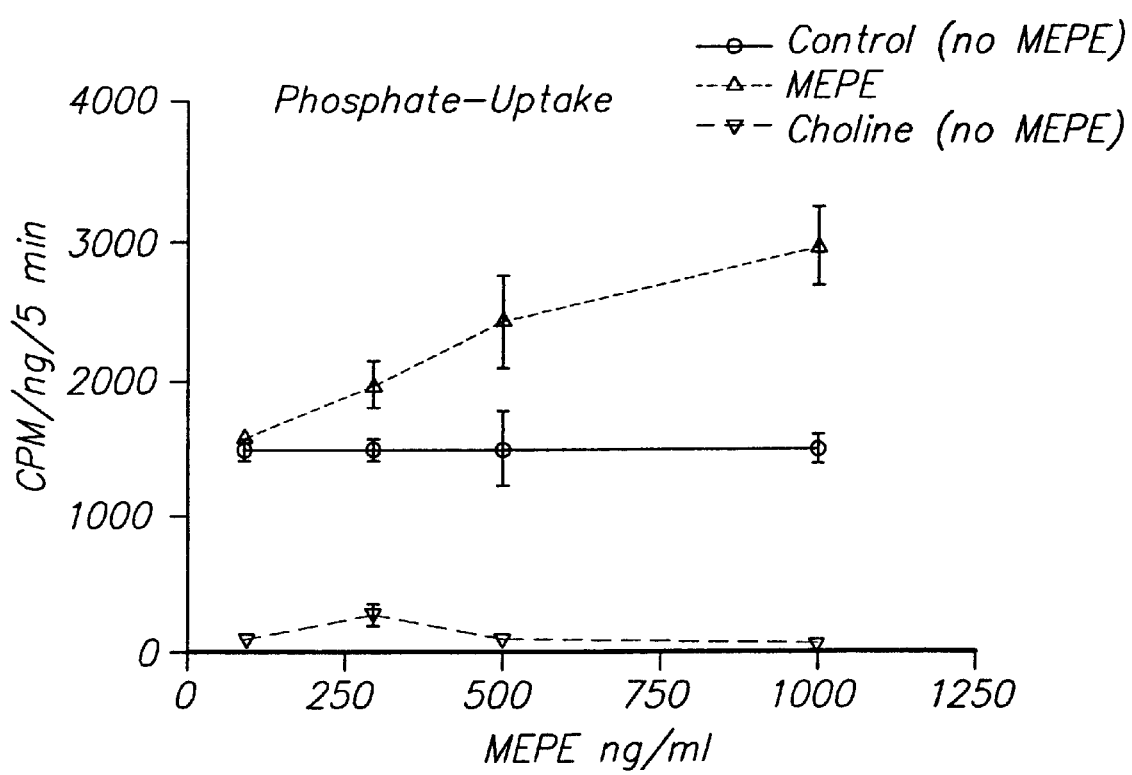
FIG. 11: Dose curve of MEPE administration and phosphate uptake with SEM error bars.

1. Primary Structure and Motifs:

The primary structure of the protein and the nucleic acid sequence are shown in FIG. 8. The largest cDNA clone isolated for MEPE was 1655 bp and contained the entire 3' end of the gene with poly A$^+$ tail and a single polyadenylation sequence (AA[T/U]AAA) (FIG. 8). An open reading frame of 430 residues was found that overlapped and extended the other smaller MEPE cDNA clones isolated, with predicted $M_r$ 47.3 kDa and a pI of 7.4. The best fit consensus start codon Kozak, Nucleic Acids. Res. 15 (1987), 8125–8148), occurs at 255 bp, although two other methionines preceded this. It is possible that additional 5' sequence is missing, and an earlier start codon and or extended 5' untranslated sequence needs to be characterized. GCG-secondary structure prediction indicates that the protein is very hydrophilic with three localized areas of low hydrophobicity (FIG. 9). The protein has glycosylation motifs at residues 382 and 385 (NNST), and residues 383–386 (NSTR). There is also a glycosaminoglycan attachment site at residues 161–164 (SGDG). The approximate molecular weight without glycosylation is 54 kDa, and is in close agreement with the purified glycosylated form of (58–60 kDa). There are a number of phosphorylation site motifs (see Table 1), and these are predicted to play a role in the biological activity of the hormone or fragments thereof.

TABLE 1

| | Site (on FIG. 8) | Motif |
|---|---|---|
| Protein Kinase C phosphorylation | 8–10 | SNK |
| | 77–79 | TPR |
| | 118–120 | THR |
| | 203–205 | TKK |
| | 228–230 | TAK |
| | 311–313 | STR |
| | 312–314 | TRK |
| | 319–321 | SNR |
| | 384–386 | STR |
| | 403–405 | SNR |
| | 408–410 | SSR |
| | 409–411 | SRR |
| Casein Kinase II phosphorylation | 8–11 | SNKE (SEQ ID NO:31) |
| | 139–142 | SDFE (SEQ ID NO:32) |
| | 177–180 | TGPD (SEQ ID NO:33) |
| | 194–197 | SEAE (SEQ ID NO:34) |
| | 199–202 | THLD (SEQ ID NO:35) |
| | 224–227 | TRDE (SEQ ID NO:36) |
| | 228–231 | TAKE (SEQ ID NO:37) |
| | 238–241 | SLVE (SEQ ID NO:38) |
| | 325–328 | TLNE (SEQ ID NO:39) |
| | 423–426 | SSSE (SEQ ID NO:40) |
| | 425–428 | SESD (SEQ ID NO:41) |
| | 427–430 | SDGD (SEQ ID NO:42) |
| cAmp- & cGMP-dependent protein kinase phosphorylation | 405–408 | RRFS |
| Tyrosine Kinase Phosphorylation | 40–47 | KLHDQEEY |
| Myristoylation | 16–21 | GLRMSI |
| | 143–148 | GSGYTD |
| | 119–224 | GNTIGT |
| | 266–271 | GSQNAH |
| | 291–296 | GSSDAA |
| | 315–320 | GVDHSN |
| | 389–394 | GMPQGK |
| Amidation | 370–373 | HGRK |
| RGD | 152–154 | RGD |
| Gycosaminoglycan Attach. Site | 161–165 | SGDG |
| Asn-Glycosylation | 382–386 | NNST |
| | 383–387 | NSTR |

A key feature of the protein is a cell attachment sequence at residues 152–154 (RGD). The Arg-Gly-Asp sequence plays a role in receptor interactions in general, and in fibronectin is essential for cell surface receptor binding to a specific integrin. More notable is the presence of this motif in some forms of collagens (bone matrix protein), fibrinogen, vitronectin, von Willebrand factor (VWF), snake disintegrins, and slime mould discoidins. It is highly probable that this part of the phosphatonin is involved in receptor and/or bone mineral matrix interactions.

Also these interactions mediate the following:
1. osteoid mineralization (osteoblasts).
2. Na-dependent phosphate co-transporter gene expression regulation.
3. 24 hydroxylase and/or 1 alpha hydroxylase gene expression regulation (kidney).
4. bone and dental mineral matrix interactions and regulation of mineral deposition via nucleation.

The presence of a glycosaminoglycan attachment sequence at residues 161–164 (SGDG), has important implications concerning bone mineral attachment and interactions. The role of proteoglycans in bone is well documented particularly in cell signaling. It is highly probable that this part of the molecule is also essential for the above bioactivities (point 1 to 4), and in particular osteoblast mediated mineralization of osteoid.

The RGD motif is in a region of predicted turn (Garnier prediction Antheprot), and is flanked by two regions of β-sheet (residues 134 to 141 and 172 to 178). The predicted sheet structure is in turn flanked by two regions of extended αhelix (121 to 132 and 196 to 201).) The general structural context, predicted turn and presence of the RGD cell attachment sequence is similar to that found in osteopontin. The protein also has a number of predicted phosphorylation motifs for protein kinase C, casein kinase II, tyrosine kinase, and cAMP cGMP-dependent protein kinase. MEPE was also found to have a large number of N-myristoylation sites, and these sites appear to be a feature of RGD containing phospho glycoproteins (osteopontin, vitronectin, collagen, h-integrin binding protein, dentin-sialophosphoprotein, dentin-matrix-protein-1, bone-sialoprotein-II and fibronectin). There is an unusually high content of aspartate, serine and glutamate residues (26%), as in osteopontin (37%). Of particular interest is the complete absence of cysteine residues in MEPE sequence, indicating that cysteine—cysteine disulphide bridges do not play a role in the secondary structure of this molecule. Sequence homology to dentin phosphoryn (DPP) was found after screening the trembl database with MEPE. A region at the C-terminus of MEPE has a sequence of aspartate and serine residues (residues 414–427) that are almost identical (80% homology), to a recurring motif found in DPP (FIG. 26A and 26B). Physicochemical comparison of the MEPE motif (SEQ ID NO: 11, i.e. DDSSESSDSGSSSESD) with the DSP motif (SEQ ID NO: 13, i.e. DSSDSSDSSSSSDS), increases the homology to 93%. The MEPE-motif occurs once at the C-terminus in MEPE (residues 414 to 427), whereas the DSP homologue is repeated at DSP residue positions 686 to 699, 636 to 646, and 663 to 677. Moreover, two related sequences SEQ ID NO: 15, i.e. DSSDSS-DSNSSSDS and SEQ ID NO: 17, i.e. DSSDSSDSSNSSDS, also with 80% homology to the MEPE-motif are found in DSP at positions 576 to 589 and 800 to 813 respectively. A similar motif with 60% homology (SEQ ID NO: 18, i.e. DDSHQSDESHHSDESD), is also found in osteopontin (residues 101 to 116), and a casein kinase II phosphorylation site is contained within the region of homology (FIG. 12). Skeletal casein kinase II activity is defective in X-linked rickets (Rifas, bc. cit.). Although the osteopontin MEPE-motif is central and not C-terminal, cleavage of osteopontin in vivo has been reported and this would generate a peptide with the MEPE motif placed C-terminal (Smith, J. Biol. Chem. 271 (1996), 28485–28491). Additional sequence homology to the C-terminal MEPE-motif is also found in DMA-1 at residues 408 to 429 of SEQ ID NO: 2, i.e. SSRRRDDSSESSDSGSSSESDG. A graphical presentation of the regional sequence homology of the MEPE-motif in DSSP, DMA-1 and OPN is presented in FIG. 12 as a lalnview statistical plot, and Table 2 presents the sequence similarities in alignment.

TABLE 2

MEPE versus DSSP
Upper sequence MEPE:

| 414 | DSSESSDSGSSSES | 427 | (SEQ ID NO:7) |
| 686 | DSSDSSDSSSSSDS | 699 | (SEQ ID NO:13) |
| 414 | DSSESSDSGSSSES | 427 | (SEQ ID NO:7) |
| 633 | DSSDSSDSSSSSDS | 646 | (SEQ ID NO:13) |
| 413 | DDSSESSDSGSSSES | 427 | (SEQ ID NO:10) |
| 551 | DDSSDSSDSSDSSDS | 565 | (SEQ ID NO:14) |
| 414 | DSSESSDSGSSSES | 427 | (SEQ ID NO:7) |
| 576 | DSSDSSDSNSSSDS | 589 | (SEQ ID NO:15) |
| 414 | DSSESSDSGSSSES | 427 | (SEQ ID NO:7) |
| 663 | DSSDSSDSSSSSDS | 677 | (SEQ ID NO:13) |
| 414 | DSSESSDSGSSSES | 427 | (SEQ ID NO:7) |
| 752 | DSSESSDSSNSSDS | 765 | (SEQ ID NO:16) |
| 414 | DSSESSDSGSSSES | 427 | (SEQ ID NO:7) |
| 800 | DSSDSSDSSNSSDS | 813 | (SEQ ID NO:17) |

MEPE versus Osteopontin:
Upper sequence MEPE

| 413 | DDSSESSDSGSSSESD | 428 | (SEQ ID NO:11) |
| 101 | DDSHQSDESHHSDESD | 116 | (SEQ ID NO:18) |

Osteopontin versus DSSP:
Upper sequence osteopontin

| 106 | SDESHHSDESD | 116 | (SEQ ID NO:19) |
| 638 | SDSSSSSDSSD | 648 | (SEQ ID NO:20) |
| 106 | SDESHHSDESD | 116 | (SEQ ID NO:19) |
| 846 | SDSSDSSDSSD | 857 | (SEQ ID NO:21) |
| 106 | SDESHHSDESD | 116 | (SEQ ID NO:19) |

TABLE 2-continued

| 857 | SDSSDSSDSSN | 878 | (SEQ ID NO:22) |

MEPE versus DMA-1
MEPE top sequence

| 408 | SSRRDDSSESSDSGSSSESDG | 429 | (SEQ ID NO:12) |
| 443 | SSRSKEDSN-STESKSSSEEDG | 463 | (SEQ ID NO:23) |

Of interest is the repetitive occurrence of the motif at the C-terminal region of DSSP or the dentin-phosphoryn portion. A dot-matrix sequence-comparison of MEPE against DSSP at high and low stringency is shown in FIG. 13, and this illustrates the repetitive occurrence of the aspartate-serine rich MEPE motif in DSSP.

DPP is formed by post-translational cleavage of a much larger protein, dentin sialo-phosphoprotein (DSSP), into two distinct proteins DPP and dentin sialoprotein (DSP). There is considerable sequence homology of MEPE and osteopontin to the dentin phosphoryn (DPP), part of dentin siaolo-phosphoprotein (DSSP), with no homology to the dentin siaolprotein portion of the molecule (DSP) (FIG. 13). Of note is the close alignment of the RGD motif, casein kinase II phosphorylation motifs and N-glycosylation sites in both DPP and MEPE (FIG. 13). Also, all the protein kinase C sites associated with DSSP are clustered in the region of overlap with MEPE (dentin phosphoryn portion), with none found in the DSP portion of the molecule.

Figure 4:
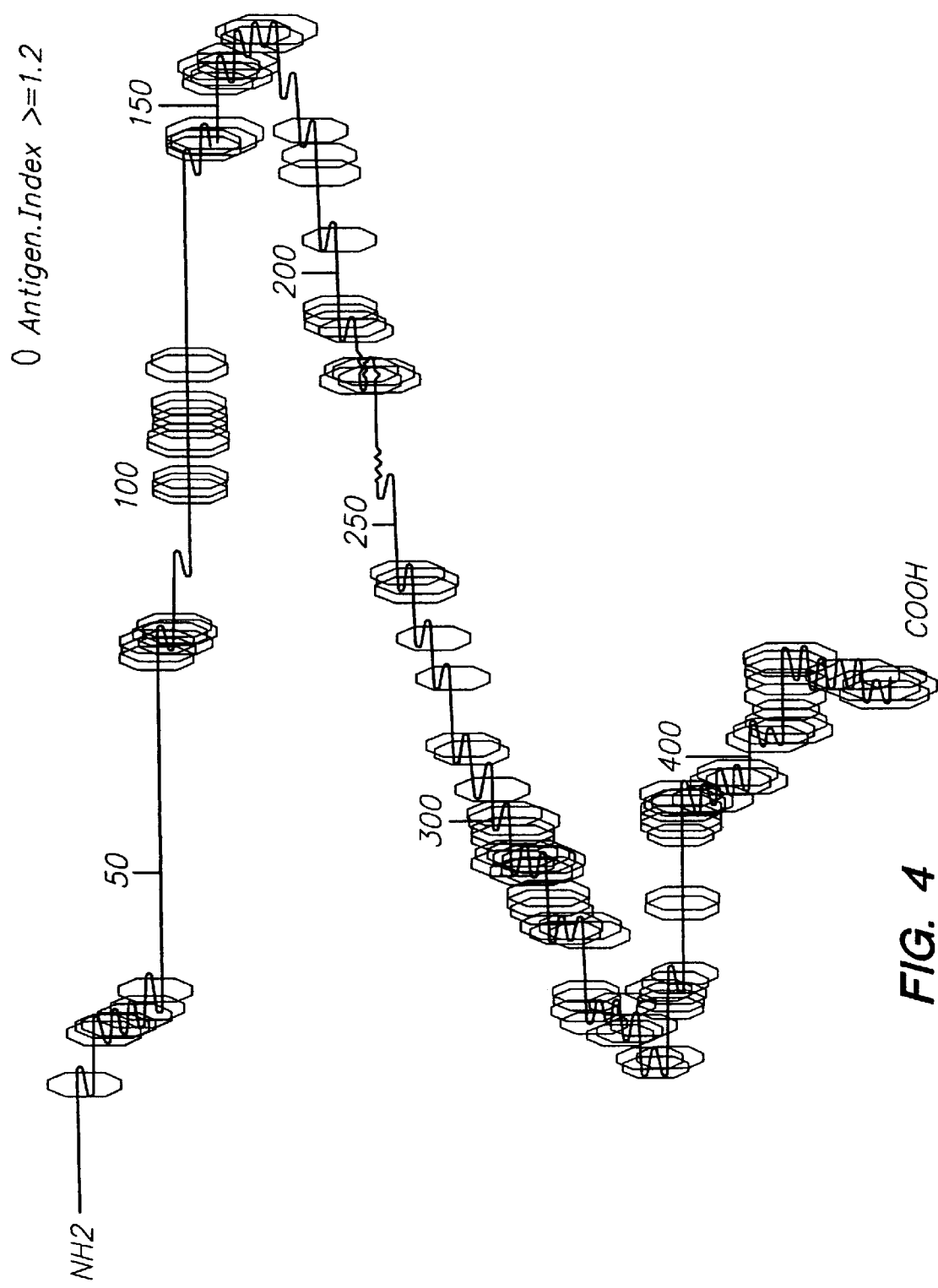
FIG. 4: Computer prediction of antigenicity of phosphatonin.
Figure 5:
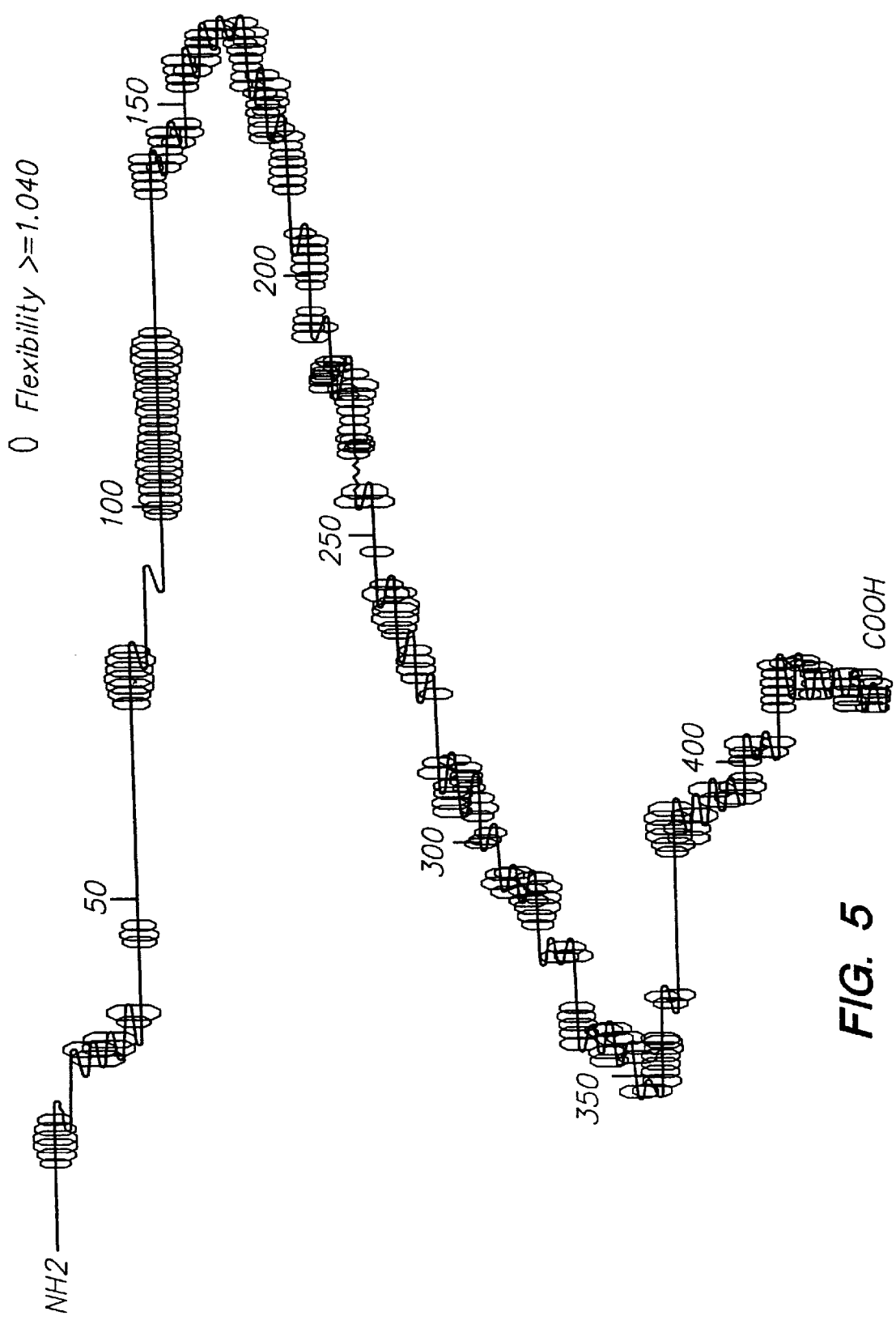
FIG. 5: Computer prediction of flexibility of phosphatonin.
Figure 6:
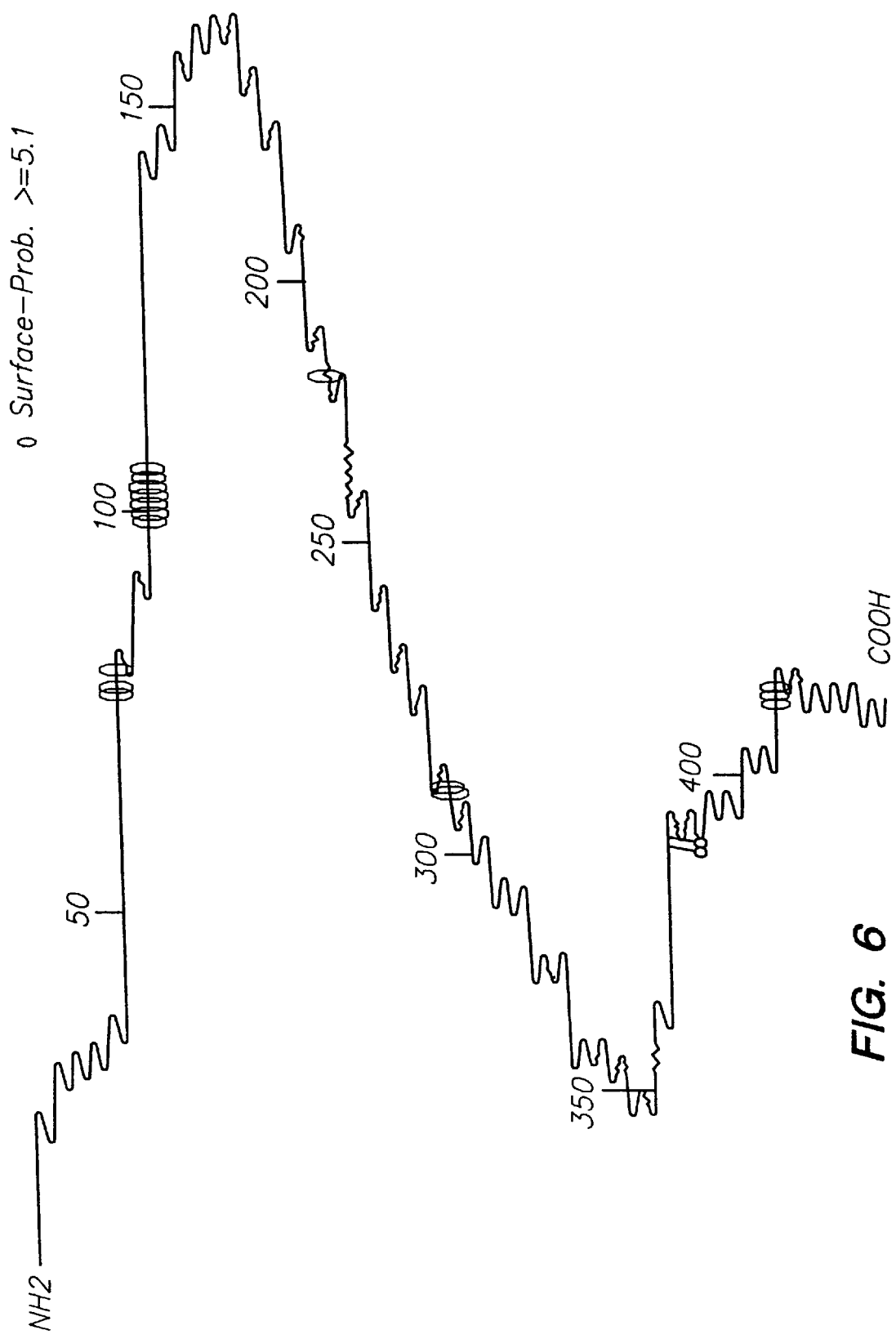
FIG. 6: Computer prediction of surface probability of the secondary structure of phosphatonin.
Figure 7:
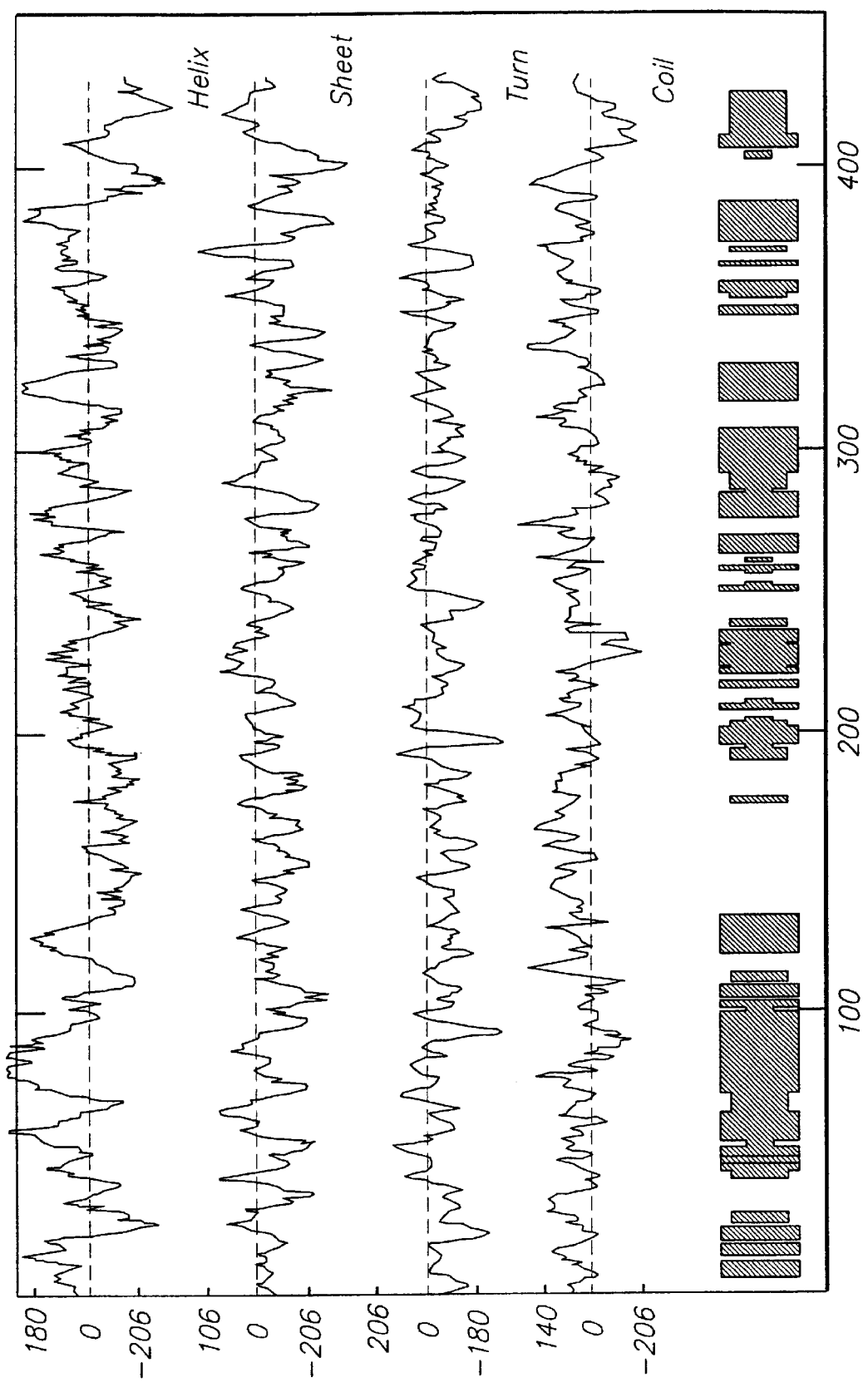
FIG. 7: Computer prediction of the secondary structure of phosphatonin.

2. Secondary Structure:

GCG peptide structure prediction profiles of hydrophobicity/hydrophilicity, antigenicity, flexibility and cell surface probability are shown in FIGS. 3 to 6. These Figures show GCG-peptide structure prediction analysis of the primary amino acid sequence. Hydrophobicity and hydrophilicity indices are represented as triangles and ovals respectively. Glycosylation motifs are represented as circles on stalks at residues 382–386. Glycosylation symbols can been seen more clearly in FIG. 6. Protein turn is indicated by the shape of the line representing primary amino acid sequence. Regions of (-helix, coil and sheet structure are indicated by localized undulations of the line (refer to FIG. 7 for more detail). Computer predictions were made using GCG-software derived from HGMP resource center Cambridge (Rice, 1995) Programme Manual for the EGCG package. (Cambridge, CB 10 1 RQ, England: Hinxton Hall). A striking feature is the lack of Sistine residues and the high degree of hydrophilicity, with four minor sites with low hydrophobic indices residues 48–53, 59–70, 82–89, and 234–241). The protein does not have a transmembranous profile as deduced from a secondary structure prediction using antheorplot software. The protein is also highly antigenic and flexible (FIGS. 4 and 5). The overall secondary structure profile is indicative of an extracellular secreted protein, and is in agreement with the proposed function of the molecule. FIG. 7 shows the helical, sheet structure, turn and coil regions of the phosphatonin. This is based on a prediction using Gamier analysis of the antheplot v2.5e package. The four lines in each section (top to bottom), represent helix, coil, sheet, and turn probability indices of primary amino acid sequence. The graph at the bottom presents the same data in block form. Notable is the high helical content, particularly at the NH2 terminus and also towards the C-terminus, which may have a functional context.

EXAMPLE 6

Medical Uses of Phosphatonin and Phosphatonin Fragments

A number of disorders are amenable to treatment using polypeptides according to the present invention.

X-linked Rickets (hypophosphatemia) (HYP):

X-linked hypophosphatemic rickets is one of the commonest inherited diseases of bone mineral metabolism (Rowe, 1997). Phosphatonin bioactive fragments such as those cleaved by PHEX and the uncleaved hormone will play a major role in the treatment of the disease. The protein cloned and described herein, is predicted to interact with its cognate receptor in the kidney and cause an inhibition in the expression of a renal Na-dependent phosphate co-transporter (NaPi), and either directly or indirectly up-regulation of a renal 24 hydroxylase. It is also predicted to down regulate expression of renal 1 (hydroxylase (directly/indirectly). After cleavage with PHEX or other post-translational modifiers, the peptide fragments derivative of the hormone are predicted to have the opposite bio-function (up-regulation of NaPi, down-regulation of 24 hydroxylase, up regulation of 1 alpha hydroxylase). The fragment containing the RGD cell attachment residue (152–154), is predicted to play a role in the receptor interactions, although other peptide derivatives may also mediate receptor ligand interactions for disparate bioactivities. Also, phosphatonin derivatives will play an important function in the normalization of the hypomineralised bone lesions. This is predicted to occur by mediating changes in the osteoblast mediated mineralization of osteoid, and by correcting the aberrant expression/phosphorylation of bone mineral matrix proteins (osteopontin/osteocalcin). The RGD cell attachment sequence and also the glycosaminoglycan attachment motif could be required for the functional nucleation and crystallization of hydroxyapatite and bone mineral.

Growth impairment is a major feature of HYP, and current treatments are unsuitable. Treatment by administration of phosphatonin-derived fragments as opposed to inorganic phosphate and vitamin D supplementation, may correct this.

Accordingly, among the useful effects of peptide fragments of phosphatonin are:

1. Correction of hypophosphatemia (NaPi, preferably renal)
2. Normalization of 24-hydroxylase 1 alpha hydroxylase activity (renal).
3. mineralization of bone and bone repair (correction/prevention of rickets).
4. Complete loss of bone pain symptoms.
5. Correction of stunted growth.

Oncogenic Hypophosphatemic Osteomalacia (OHO):

The clinical profile of OHO is similar to HYP. There is a renal phosphate leak, low circulating levels of 1,25 dihydroxy vitamin D3 (calcitriol), elevated alkaline phosphatase, bone hypomineralization that in adults is presented as a generalized bone softening (osteomalacia) and low serum phosphate. The pathophysiologies of HYP and OHO clearly overlap. In rickets, the defect is a non functional PHEX gene. However, in OHO it is circulating unprocessed phosphatonin. The tumours are often difficult to find, and can be extremely difficult and dangerous to resect. Control of phosphate metabolism and bone mineralization is essential when removal of tumour is contra-indicated. Administration of PHEX to patients to cleave hormone is predicted to be dangerous as other circulating hormones and proteins may also be affected by promiscuous cleavage. Phosphatonin-fragments could instead be designed that have high receptor affinity and bioactivity, such that they would compete effectively with unprocessed tumour-derived circulating hormone.

Other Rickets or Hypophosphatemic Conditions:

There are many causes of rickets besides HYP and OHO, the most common involve abnormalities of vitamin D, but there are causes such as hypophosphatemia, renal tubular acidosis, use of certain medications, sprue, cystic fibrosis etc. Use of fragments of phosphatonin, and phosphatonin itself may be of use in treating these diseases. Some of the diseases are briefly discussed below (diseases resulting in hyperphosphatemia are potentially treatable by use of the whole hormone).

Renal Transplants and Renal Osteodystrophy:

A chronic feature of renal transplantation is the development of a renal phosphate leak (hypophosphatemia), and abnormal bone mineralization. Phosphatonin fragments would be effective in treating this without the side-effects associated with current medications.

Osteodystophy (a combination of bone disorders), is usually caused by chronic kidney failure (renal disease). Renal failure will result in death, unless dialysis is given (end stage renal disease). Therefore, patients with osteodystrophy are usually on dialysis therapy. This bone disease, which is also referred to as "renal osteodystrophy", is common in patients on chronic hemodialysis. Secondary hyperparathyroidism develops in most patients with chronic renal failure, and is associated with the histologic finding of osteitis fibrosa cystica. The disease is characterized by growth failure and severe bone deformities in children, especially the very young. The pathogenesis of renal osteodystrophy is related to phosphate retention (hyperphosphatemia), and its effect on calcium and calcitriol metabolism, in addition to roles played by metabolic acidosis, cytokines, and degradation of parathyroid hormone. Treatment includes restriction of dietary phosphorous intake, phosphate binders, and use of active metabolites of vitamin D. In this context addition of unprocessed hormone would be a powerful means of controlling phosphate levels, and would lead to bone healing. If receptors for phosphatonin are expressed in a range of tissues as well as the kidney, then the potential for treating patients with end stage renal disease exists (i.e. complete loss of kidney function).

Osteoporosis/bone Mineral Loss:

Post-menopausal women are prone to loss of bone mineral with consequent damage to the integrity of the skeleton. The cause is unknown but is likely to involve a complex interaction of genetic and environmental factors. Current research is focussed on refining statistical models to analyze multifactorial diseases such as osteoporosis.

The use of phosphatonin-derivative fragment(s) would help in the treatment of this disease by potentially reversing the bone mineral loss. Moreover, the bioactive peptides could be modified to increase potency and specificity of action.

Pagets Disease of Bone:

Pagets disease occurs due to asynchronous bone re-modeling. Bone mineralization (mediated by osteoblasts), and bone resorption (mediated by osteoclasts), are out of step. Excessive osteoclast resorptive activity occurs (predominantly in the early resorptive phase), and bone marrow is replaced by fibrous tissue and disorganized trabeculae. Although the cause is unknown, administration of peptide derivatives of phosphatonin may help in the treatment of the disease.

Diseases Related to Disorders in NaPi in Other Tissues than Kidney:

The sodium dependent phosphate co-transporter (NaPi) is expressed not just in the kidney but in many other tissues. Three type of NaPi, namely Type I, II, and III have been described thus far and all of them are said to be expressed in the kidney. In tissues other than the kidney, Type III is said to be expressed ubiquitously (Murer, Eur. J. Physiol. 433 (1997) 379–389; Kavanaugh, Kidney Int. 49 (1996) 956–963) and Type I has been confirmed to be expressed in the liver and brain in addition to the kidney (Hilfiker, PNAS 95 (1998), 14564–14569). On the other hand, Type II had been believed to be expressed only in the proximal tubule of the kidney.

Although the proximal tubule of the kidney is known to express all of the above three types, it is widely accepted that Type II plays the most significant role in terms of phosphate reabsorption at this site. This has been demonstrated by a knockout mouse in which the gene (named Npt2) encoding Type II NaPi was inactivated. The homozygous mutants (Npt2-/-) exhibited increased urinary phosphate excretion, hypophosphatemia, elevation in the serum concentration of 1,25-dihydroxyvitamin D, and other typical symptoms with hereditary hypophosphatemic rickets with hypercalciuria (HHRH) (Beck, PNAS 95 (1998), 5372–5377). Since the regulation of phosphate homeostasis in mammals is largely determined by the kidney, this result is thought to demonstrate that Type II NaPi plays the most important role in systemic phosphate homeostasis among all three types. Also, these facts, together with the result from the CL8 cell line experiment in the examples indicate that the NaPi that is regulated by Phosphatonin in the kidney is predominantly the Type II.

One of the major clinical problems with renal failure patients is hyperphosphatemia. There is a significant clinical value if such excessive serum phosphate is controlled. Therefore, phosphatonin, its fragments or derivatives which can downregulate NaPi and reduce serum phosphate level has a major potential value. In progressive renal failure patients (before so-called end stage renal disease=ESRD), downregulation of NaPi expressing in the kidney by phosphatonin will be valuable.

However, once these patients become ESRD and the majority of kidney function is lost, phosphatonin will eventually lose its action site in the kidney because no more phosphate will be excreted from glomeruli. At such a disease stage, a potential value exists in controlling phosphate absorption from the diet in the digestive tract. The digestive tract, particularly the intestine, is the only place where phosphate is taken up from the diet into the circulation. Therefore, this will be the next major target to control phosphate uptake into the circulation after the kidney function is lost.

A subtype of the Type II NaPi, named Type IIb was reported to be cloned from mouse intestine (Hilfiker, PNAS 95 (1998), 14564–14569). Although it is yet to be known if phosphatonin can effect on the intestinal Type IIb NaPi, it is reasonably expected that this Type IIb NaPi in the intestine plays a major role in the absorption of phosphate from the diet and that phosphatonin may be the most significant factor for its up- and downregulation.

EXAMPLE 7

Pharmaceutical Compositions

Pharmaceutical compositions may be formulated comprising a polypeptide according to the present invention optionally incorporating a pharmaceutically-acceptable excipient, diluent or carrier. The exact nature and quantities of the components of such compositions may be determined empirically and will depend in part upon the route of administration of the composition. Routes of administration to patients include oral, buccal, sublingual, topical (including ophthalmic), rectal, vaginal, nasal and parenteral (including intravenous, intraarterial, intramuscular, subcutaneous and intraarticular). In order to avoid unwanted proteolysis, a parenteral route is preferred.

Suitable dosages of a molecule of the present invention will vary, depending upon factors such as the disease or disorder to be treated, the route of administration and the age and weight of the individual to be treated. For instance for parenteral administration, a daily dosage of from 0.1 µg to 1.5 mg/kg of a molecule of the invention may be suitable for treating a typical adult. More suitably the dose might be 1 µg to 150 µg. Accordingly, it is envisaged that the active polypeptide ingredient may be given in a dose range of from 0.01 to 100 mg, typically 0.1 to 10 mg, on a daily basis for an adult human.

Compositions for parenteral administration for example will usually comprise a solution of the molecule dissolved in an acceptable carrier, preferably an aqueous carrier. A variety of aqueous carriers can be used such as water, buffered water, 0.4% saline, 0.3% glycine etc. Such solutions should advantageously be sterile and generally free of aggregate and other particulate matter. The compositions may contain pharmaceutically acceptable buffers to adjust pH, or alter toxicity, for example sodium acetate, sodium chloride, potassium chloride, calcium chloride, sodium lactate, etc. The concentration of molecule in these formulations can vary widely, for example from less than about 0.5% to as much as 15 or 20% by weight and could be selected as appropriate by a skilled person.

Typical pharmaceutical compositions are described in detail in Remington's Pharmaceutical Science, 15th ed., Mack Publishing Company, Easton, Pa. (1980). For example, phannaceutical compositions for injection could be made up to contain 1 ml sterile buffered water, and 50 mg of molecule. A typical composition for infusion could be made up to contain 250 ml of sterile Ringer's solution, and 150 mg of molecule. Actual methods for preparing compositions will be known or apparent to those skilled in the art. Approaches to formulation and administration of polypeptide pharmaceutical compositions are well-known to those skilled in this art and are discussed, for example, by P. Goddard in Advanced Drug Delivery Reviews, 6 (1991) 103–131.

EXAMPLE 8

Further Characterization of Phosphatonin (MEPE) and its Encoding Gene

Clinical Profile of Patients (BD, ND, EM and DS) with Oncogenic Osteomalacia:

Patient BD has been described in an earlier publication (Rowe, Bone 18 (1996), 159–169), and a case report for patient ND has also been published (David, J. Neurosug. 84 (1996), 288–292). Both patients exhibited classical tumour-osteomalacia, and presented with low serum phosphate and radiological osteomalacia, and low serum 1,25 vitam D3. Patient BD (44 year old woman), and patient ND (66 year old woman), exhibited complete remission of symptoms after removal of tumours from the left nasal cavity (haemangiopericytoma), and the intracranial space (mesenchymal hemopericytoma like tumour), respectively. Patient ND had three such operations over a period of twenty years, and remission occurred after each resection.

Tumour Conditioned Media:

Tumour samples from both BD, ND and EM were collected immediately after resection. Samples were then cut into ~1 mm pieces and some frozen in liquid nitrogen. The remaining pieces of tumour tissue were processed for tissue culture as described previously (Rowe, Bone 18 (1996), 159–169). In brief, samples were digested with collagenase overnight, and then subjected to alternate cycles of culture in the presence and absence of serum (DMEM media). With patient ND, additional samples from, surrounding sub-dura, and dura were also collected and treated as described above. Also, control skin fibroblast cultures from patient BD were obtained on the same day as tumour resection, and treated in the same way as the tumour samples. Samples from patient BD were labeled as follows: 1: tumour conditioned media (TCM-BD); 2: skin conditioned media (SCM-BD). Samples from patient ND were labeled as follows: 1: Tumour conditioned media (TCM-ND); 2: sub-dura conditioned media (SDCM-ND); 3: dura conditioned media (DCM-ND); 4: fluid surrounding intracranial-tumour (FST-ND). All samples were collected from culture cycles in which cells were grown in serum-free DMEM media, unless indicated in the text by addition of 'serum supplemented' to the above abbreviations.

Concanavilin A Affinity Chromatography of TCM:

Concanavilin-A affinity chromatography of tumour conditioned medium (TCM) from patient ND, performed in accordance with Example 1 resulted in the isolation of high and low affinity fractions (HCA, and LCA respectively). Both HCA and LCA fractions were eluted with α-methyl-D-glucopyranoside (0.5M) elution buffer. Briefly, partial purification of TCM proteins was carried out by Conacanavilin A affinity chromatography using a method described by (Wagner, Gen. Comp. Endocrinol. 63 (1986), 481–491), with modifications. Concanavilin A Sepharose (Pharmacia Code No: 17-0440–01, 14 ml), in 20% Ethanol, was first washed with several column volumes of water, and then equilibrated in running buffer (CRB; 0.06M Sodium phosphate pH 7.2 and 0.5M NaCl). The equilibrated slurry was then added to a 12 mm×115 mm Pharmacia screw top column, and three column volumes of CRB running buffer added at a flow rate of 0.4 ml/min (FPLC/HPLC millenium Waters chromatography system). Conditioned media equilibrated in CRB buffer (10 ml), was then added to the column and allowed to bind. The column was then washed with several column volumes of CRB loading buffer, and elutions of bound proteins was then carried out by addition of sodium phosphate elution buffer (ERB; 60 mM pH 7.2/0.5M NaCl/0.5M α-methyl-D-glucopyranoside/0.01% azide), at a flow rate of 0.2 ml/min (40 ml). High affinity proteins were eluted after incubation of the column overnight in ERB buffer followed by a second passage of ERB buffer at 0.2 ml/min. Elution profiles for both high and low concanavilin A-affinity TCM-proteins were identical and produced a single symmetrical peak at 1.6 column volumes. Peak LCA represented ⅓ the total mass of peak HCA, and 1 ug of HCA material was retrieved from 10 ml of tumour conditioned media (TCM), from patient ND.

SDS-PAGE of TCM and Concanavilin A Fractions:

Tumour conditioned medium, conditioned media and concanavilin A peaks (HCA and LCA), were separated by SDS-PAGE and visualized after Sybr-Orange staining. SDS-polyacrylamide gel electrophoresis was carried out using a Novex NuPAGE™ Electrophoresis system consisting of 4–12% Bis-Tris acrylamide-gradient gels (pH 6.4), and MOPS-SDS (50 mM 3-[N-morpholino] propane sulfonic acid; 50 mM Tris-base; 3.5 mM SDS; 1.0 mM EDTA; pH 7.7) running buffer. Runs were carried out at a constant voltage of 200 for 50 min. Samples were denatured at 70° C. for 10 minutes in NuPage LDS sample buffer (10% glycerol; 1.7% Tris-Base; 1.7% Tris-HCl; 2% Lithium Dodecyl Sulfate; dithiothreitol 50 mM; 0.015% EDTA; 0.075% Serva Blue G250; 0.025% Phenol red; pH7.5 final concentration). NuPage antioxidant was added to the upper electrophoresis chamber as recommended by the manufacturers. Following electrophoresis proteins were stained by incubating the gels in 7.5% acetic acid supplemented with SYPRO-Orange. Visualization of proteins was achieved after UV illumination using a Bio-Rad FluorImager gel-imaging system. HCA and LCA fractions stained positive for two proteins at 56 kDa and 200 kDa respectively and gave identical profiles. Conditioned media (patient ND), from intracranial-tumour, sub-dura (immediately adjacent to tumour in the patient), and dura material contained several major bands spanning ~50–80 kDa. A prominent band was present in all preparations at ~66 kDa with a weaker very high molecular weight component at ~200 kDa present in tumour and sub-dura. The relative intensity of the ~200 kDa was highest in the tumour material, and absent in the dura. A diffuse set of bands at ~55–60 kDa was present in tumour and sub-dura but absent in the dura conditioned media (patient ND). Conditioned media from skin and media control did not reveal any staining for protein. Conditioned media from patient BD and EM gave similar profiles except for the absence of the high molecular weight protein at 200 kDa. Nonphosphaturic tumour tissues from patients LA and SL, and also skin controls all contained the 66 kDa band and also diffuse staining at 50–60 kDa. Concanavilin-A affinity peaks HCA and LCA were enriched for the high molecular weight 200 kDa band and also contained proteins from the 50–66 kDa range. Conditioned media from bone cell lines HTB96 and SaOs2 gave almost identical protein profiles to tumour conditioned media from OHO-patient ND. The 200 kDa band intensity in SaOS2 was reduced relative to TCM from brain tumour (patient ND), sub-dura (patient ND), and CM from HTB96.

Immuno-blotting and Glycoprotein Staining of TCM and Purified Fractions:

For western-blotting, proteins were transferred to PVDF membranes (Amersharn), using submarine electrophoresis. After SDS-PAGE electrophoresis, gels were equilibrated in transfer buffer: 25 mM Tris-HCl; 0.38 M glycine; 0.2% SDS (TB) for 1 h at room temperature. PVDF membranes were cut to size, briefly rinsed in methanol, washed in distilled water, and then equilibrated in TB. The equilibrated gel and PVDF membrane were then sandwiched between filters and placed in a cassette. The cassette was then placed in a Hoeffer system submarine electroblotter with TB buffer and cooling maintained at 4° C. by thermocooler. Transfer of proteins was then carried out by positioning the PVDF end of the sandwich towards the anode, and electrophoresis at a constant 0.4 A (45V), for 45 min. Blots were screened with 1/1000 dilution of pre-Anti-op antisera, post-Anti-op-antisera, or calmodulin conjugated to alkaline phosphatase using the methods described in the Enhanced-Chemiluminescence kit (Amersham; ECL+), or the calmodulin affinity detection kit (Stratagene) respectively. Chemiluminescence, was detected and filmed using the Bio-Rad FluorImaging system, and the calmodulin-affinity binding was visualized using the colourometric system discussed earlier for clone detection (Stratagene). Biotinylated molecular weight markers (Amersham), were used as internal controls to asses transfer and molecular weight. Streptavidin conjugated to horse radish peroxidase (HRP), was added to the secondary antibody (goat-anti-rabbit IgG conjugated to HRP), to facilitate visualization of the biotinylated-markers via chemiluminescence.

Western blots of phosphaturic tumour-conditioned-media (TCM), from OHO-patients gave positive chemiluminescent bands when screened with pre-absorbed pre-operation antisera. Non-phosphaturic tumours, tissue controls from skin and media controls were all negative when screened with pre-absorbed pre-operation antisera. Also, all TCM and conditioned media samples were negative when screened with post-operation antisera.

Screening of TCM proteins from patient ND, and osteosarcoma cell lines HTB96 and SaOS2 with pre-absorbed pre-operation antiserum revealed two distinct immuno-positive bands at ~54–57 kDa and ~200 kDa. Patient ND tumour sample and adjacent sub-dura tissue gave much stronger 54–57 kDa signals relative to dura brain-sample conditioned-media, and no staining for the 200 kDa band was found in the dura conditioned-media. Both HCA and LCA concanavilin-A fractions contained a very strong signal for the 200 kDa band, and a reduced but visible signal at 54–57 kDa. Cell lines SaOS2 and HTB96 were also positive for the same bands, but SaOS2 conditioned media had a reduced signal for the 200 kDa band relative to TCM and HTB96.

Skin conditioned media (patient ND and BD), and media controls were negative, as were screenings with post-operation antisera (Rowe, Bone 18 (1996), 159–169). Recombinant MEPE (rec-MEPE), stained positively with pre-absorbed pre-operation antisera, and this could be competed out with added rec-MEPE). A positive band of 54–57 kDa was obtained with Sybr-Orange protein stained, and pre-absorbed pre-operation antisera screened rec-MEPE. This was the same size as the 55–57 kDa band (pre-absorbed-pre-operation western screened), found with patient ND tumour conditioned media, and osteosarcoma cell lines HTB96 and SaOS2. Recombinant-MEPE contains an additional 4.5 kDa CBP-tag at the N-terminus that decreases mobility and results in an apparent increase in molecular weight on SDS-PAGE gels. Thus, the equivalent size of tumour derived protein and rec-MEPE may be due to post-translational modification of tumour derived MEPE (possibly glycosylation).

TCM western blots from OHO-tumour patients BD and EM contained major pre-absorbed-pre-operation antisera positive bands at slightly lower molecular weight (48–52 kDa), as well as a band co-migrating at 55–57 kDa with rec-MEPE. Other higher molecular weight bands were also seen at 61, 75, 80, and 93 kDa (weaker signals).

In all samples the major SYBR-Orange stained protein band at 66 kDa was negative when screened with pre-absorbed pre-operation antisera. Glycoprotein screening of duplicate blots gave the same results as screening with pre-operation antisera and both 54–57 kDa and 200 kDa bands stained positive confirming that these proteins are glycosylated. Proteins were separated by SDS-PAGE and blotted onto PVDF membranes as described in methods above. Specific glycoprotein detection was carried out using an Immuno-Blot kit for glycoprotein detection (Bio-Rad), and Amersham biotinylated markers were added as internal controls. Briefly, after transfer membranes were treated with 10 mM sodium periodate in sodium acetate/EDTA buffer to oxidise carbohydrate moieties. The blots were then washed in PBS and incubated with hydrazide in sodium/acetate/EDTA buffer for 60 minutes at room temperature. Filters were then washed three times (10 minutes) with TBS. Subsequent blocking and detection was carried out as described earlier using the Enhanced chemiluminescence kit (Amersham), and streptavidin horse radish peroxidase. Primary antibody and secondary goat anti-rabbit-HRP was not used.

In conclusion pre-absorbed pre-operation antisera specifically detects proteins derived from oncogenic hypophosphatemic osteomalacia-TCM. The major proteins detected fall into two three distinct molecular size ranges 48–52 kDa, 54–57 kDa, and 200 kDa. All OHO-TCM samples were positive for the 54–57 kDa protein, and all proteins detected by pre-absorbed-pre-operation antisera stained positive when screened for glycoprotein status. Non OHO-tumours control tissues and media were negative when screened with pre-absorbed pre-operation antisera.

EXAMPLE 9

Expression of MEPE Fusion-protein from pCAL-n-EK Vector

The entire cDNA coding sequence was subcloned into pCAL-n-EK as described in Example 4a. Validation of the fusion construct generated by IPTG induction of the *E. coli* host BL2 1 (DE3), was achieved by screening western blots with pre-operation antisera, and also with calmodulin conjugated to alkaline phosphatase as described above. The fusion protein with microbial CBP-tag (calmodulin binding peptide of 4.5 kDa), containing calmodulin peptide, enterokinase site, and thrombin site was 56 kDa as deduced by SDS-PAGE. This is in approximate agreement with the expected molecular size (~48 kDa). Purification of protein was achieved by calmodulin affinity chromatography as described above. Preincubation of pre-operation antisera with purified fusion construct resulted in a diminution of the 55–57 kDa signal observed on screening TCM western blots, but not the 200 kDa band. The failure to completely reduce the 55–57 kDa signal was presumed to be due to specific recognition of the highly antigenic glycosylation moiety present in the nascent MEPE-protein (TCM), but absent in the microbial fusion-construct of rec-MEPE. The fusion protein was soluble in aqueous Tris-buffers and detergents were not required at any stage of the purification process.

EXAMPLE 10

Tissue Expression (RT/PCR and Northern Analysis)

Northern blots containing poly A+RNA were screened with MEPE cDNA and no hybridization was detected to stomach, thyroid, spinal cord, lymph node, trachea, adrenal gland, bone marrow, heart, brain, lung, liver, skeletal muscle, kidney, and pancreas (Clontech MTN-blots I and III). For Northern analysis two blots from Clontech (MTN™ and MTN™ III), containing the following poly A+ RNA's: 1; heart, 2; brain, 3; placenta, 4; lung, 5; liver, 6; skeletal muscle, 7; kidney, 8; pancreas, 9; stomach, 10; thyroid, 11; spinal cord, 12; lymph node, 13; trachea, 14; adrenal gland, 15; bone marrow, were screened with MEPE cDNA amplified with specific internal primers (Pho433-111 F and PHO877-111R). Primer sequences for Pho433-111 F and PHO877-111R are highlighted in FIG. 8 (nucleotide positions 433 to 456 (SEQ ID NO: 24) and 877 to 900 (SEQ ID NO: 25), respectively), and the following PCR conditions were used: predenaturation; 95° C. 3 min; followed by thirty cycles of denaturation; 95° C. 45 sec, annealing; 65° C. 30 sec, polymerization; 72° C. 45 sec, and a final extension of 72° C. 7 min followed by cooling to 4° C. PCR-buffer (PB) was used with a final concentration of 2 mM MgCl$_2$. The 444 bp amplified MEPE cDNA product was then resolved by submarine agarose electrophoresis, visualized by ethidium bromide staining, and purified using glass beads (Gene-clean II kit; Bio 101 INC). Purified DNA was then radiolabeled using α-P$^{32}$ dCTP (3000 ci/mmol) in conjunction with the MegaPrime labeling-kit from Amersham. Specific activities of 5×10$^9$ cpm/µg were routinely obtained. Hybridization (60° C.), and prehybridization (60° C.), of blots were carried out using published methods (Rowe, Hum. Genet. 97 (1996), 354–352), and stringency washes were carried out as follows: 1; two washes at room temperature for 30 min with 2× SSC 0.1% SDS, two washes at 60° C. for 30 min in 0.1× SSC 0.1% SDS. Filters were then exposed to film for 7 days at −80 C and the films developed. Total human-RNA from adrenal glands, brain, duodenum, heart, kidney, liver, lung, skin, spleen, thymus, thyroid, tonsil, did not amplify using RT/PCR and MEPE specific primers, although evidence for low level expression using cDNA template was found for brain, kidney, liver and pancreas. For this experiment, total RNA was extracted from the following human tissues: 1; Thymus, 2; brain, 3; testis, 4; duodenum, 5; heart, 6; skin, 7; liver, 8; tonsil, 9; spleen, 10; thyroid, 11; adrenal, 12; lung, 13; kidney, 14; OHO-tumour tissue, 14; Human primary osteoblast. Total RNA from Rat primary osteoblast was also obtained. MEPE Internal primers as described above (Pho433-111 F and PHO877-111R), were used to copy total RNA using reverse transcriptase-PCR and the Perkin Elmer-Roche RNA PCR kit. Briefly, 1 ug of total RNA was dissolved in 20 µl of 10 mM Tris-HCl (pH 8.3), 50 mM KCl, 5 mM MgCl$_2$, 1 mM dNTPs, 1 unit/µl ribonuclease inhibitor, 2.5 unit/µl MULV reverse transcriptase, 0.75 µM down stream primer (PHO877-111R). The mixture was then incubated at 37° C. for 10 min. Upstream primer (Pho433-111 F), dNTPs, MgCl$_2$, and AmpliTaq DNA polymerase, was then added to give final concentrations of 0.15 µM, 200 µM, 2 mM, and 2.5 units/100 µl respectively in a total volume of 100 µl. PCR was then carried out using a Perkin Elmer thennocycler (system 9700), set to the following program: predenaturation; 95° C. 3 min; followed by thirty five cycles of denaturation; 95° C. 45 sec, annealing; 65° C. 30 sec, polymerization; 72° C. 45 sec, and a final extension of 72° C. 7 min followed by cooling to 4° C. Amplified products were resolved using agarose-gel electrophoresis, and verified by southern blotting, and sequencing. Also, a panel of normalized cDNA's derived from a range of non-OHO tumours (Breast carcinoma, lung carcinoma I, colon adenocarcinoma I, lung carcinoma II, prostatic adenocarcinoma, colon adenocarcinoma II, ovarian carcinoma, pancreatic carcinoma; Clontech human-tumour panel #K1422-1) were all negative to MEPE PCR, except for very low level expression in one case of colon adenocarcinoma, ovarian carcinoma, and prostatic carcinoma respectively (detected after southern screening of RT/PCR amplified products with radiolabeled MEPE cDNA). In sharp contrast, RT/PCR using MEPE primers amplified poly A+RNA, from OHO tumours, from four separate patients BD, DM, EM, and DS, indicating high levels of expression (normalized against glyceraldehyde 3-phosphate dehydrogenase and transferrin). Poly A+ RNA from non-phosphaturic tumours and control tissues from OHO-patients (skin and material adjacent to tumours), CL8 human-renal cell line, human primary osteoblast cells (purchased from Clonetics H-OST, see materials), and poly A+ RNA extracted from a presumed tumour-polyp from a patient with linear sebaceous naevus syndrome (TCM from polyp did not inhibit phosphate uptake in human renal cell line CL8), did not amplify using MEPE specific primers. Using Clontech purchased cDNA's derived from heart, brain, placenta, lung, liver, skeletal muscle, kidney, and pancreas (human panel I #K1420-1), as templates for MEPE primer PCR, low level expression was detected in brain, liver, lung and pancreas. Sequencing of the MEPE-primer amplified bands revealed complete homology to MEPE cDNA and southern screening of the amplified bands with MEPE cDNA confirmed the sequencing results. OHO template poly A+ RNA from all OHO-patients consistently amplified an expected band of 480 bp and a lower band of 190 bp. The upper band was confirmed by sequencing and southern autoradiography as completely homologous to MEPE sequence, and the lower band was confirmed as a MEPE-derivative by southern analysis. The lower band did not appear in the low level expression normal-tissues or non OHO-tumours. This indicates that alternative splicing may play a role in the tumour derived MEPE. All RT/PCR and PCR experiments were normalized against G3PDH and transferrin.

In summary high level expression of MEPE (as measured by mRNA levels), was found only in OHO-tumour samples, and evidence for very low level expression (possibly ectopic), was found in brain, liver, kidney and three out of eleven non-OHO tumours. Eight out of eleven tumours were negative for MEPE mRNA expression (RT/PCR), and all results were standardized against GA3PDH and transferrin RT/PCR primers,

EXAMPLE 11

Southern Analysis (Genomic Blots)

Genomic blots containing immobilized DNA derived from a family with autosomal rickets (Rowe, Hum. Genet. 91 (1993), 571–575), and digested with PstI, EcoRI, PvuII, and MspI respectively were screened with radiolabeled MEPE cDNA as described above. Southern analysis was carried out using genomic digests of DNA extracted from blood as described previously (Rowe, Hum. Genet. 93 (1994), 291–294). The PstI blot revealed the presence of an 11 kb band and also a 4 kb polymorphism in one of the sixteen family members screened. The EcoRI, PvuII, and MspI blots were all positive for single bands of 6 kb, 6.5 kb, and 4 kb respectively, and confirmed the human provenance of the gene. Due to the lack of genetic information it was not possible to deduce whether the gene segregated with the disease in this autosomal rickets family.

EXAMPLE 12

Phosphate Uptake in a Human Renal Cell Line CL8: TCM and MEPE Supplementation Phosphate and glucose uptake experiments were conducted on a human renal cell line (CL8) as described previously (Rowe, Bone 18 (1996), 159–169). In brief cells were cultured in defined medium (DM), to confluency or overnight incubation in 24 well flat bottom tissue culture plates (Falcon 3047). The DM was then replaced with fresh DM supplemented with purified fusion protein or concanavilin affinity purified TCM and left overnight at 37° C. Uptake of $P^{32}$ and $C^{14}$ methyl-glucose was then measured (Rowe, Bone 18 (1996), 159–169).

Addition of TCM (1/20 dilution), to human renal cell lines resulted in a significant reduction in Na+ dependent phosphate uptake as reported earlier (Rowe, Bone 18 (1996), 159–169). This inhibition was prevented by preincubation of TCM with pre-operation and not post operation antisera, also reported earlier (Rowe, Bone 18 (1996), 159–169). Addition of high and low affinity concanavilin-A purified fractions (HCA and LCA respectively), at concentrations of 40 ng/ml also resulted in inhibition of Na+ dependent phosphate uptake (NaPi). In both TCM and concanavilin-A fractions the inhibition was specific to phosphate uptake, and did not affect of Na+ dependent a-methyl-D-glucose uptake. In all cases the affects were dose dependent.

Similar experiments were carried out with MEPE fusion-protein purified by calmodulin affinity chromatography. Surprisingly, recombinant MEPE did not inhibit Na+ dependent phosphate co-transport, but increased phosphate uptake in a dose dependent manner (see FIG. 24). A doubling of phosphate uptake was observed at 1000 ng/ml (p<0.001). These experiments confirm that MEPE fusion protein specifically increases Na+ dependent phosphate co-transport in a human renal cell line CL8.

EXAMPLE 13

Cloning of the cDNA Encoding the N-terminus of the Phosphatonin Protein

The λZAP II uni library described in Example 4 was used for cloning of a cDNA fragment encoding the additional N-terminus of the phosphatonin protein. 5 µl of the λZAP II library described in Example4 4 was used as substrate (a total of 100000 plaque forming units) in a total volume of 50 µl consisting of the following ingredients: 10 mM Tris-HCL pH 8, 50 mM KCL, 200 µM dNTP's, 2.5 mM MgCl$_2$, 1 µM GSP2 primer (5' TCTTCCCCCAGGAGTTTAATC 3' SEQ ID NO: 28), 1 (M T3 λZAP II specific primer (5' ggc cgc aat taa ccc tca cta aag g 3' SEQ ID NO: 29) and 2.5 Units of Promega Taq polymerase. PCR amplification/thermocycling was as follows: 2 min 94° C., 30 sec 94° C., 1 min 63° C., 50 sec 72° C., for 30 cycles followed by 10 min at 72° C. and cooling to 4° C. A Gene-Amp Perkin Elmer cycler 9700 was used. The amplified PCR product was then separated using conventional submarine Nusieve-agarose electrophoresis in Tris acetate buffer. The DNA-band was then visualized by uv, and ligated directly to TA vector pCR2.1 from Invitrogen (using Invitrogens method). The ligated molecule was then transformed into E. coli XL1-blue mrf' (Stratagene cells), using conventional techniques and competent cells as described by Stratagene. Insert and vector were sequenced using conventional automated sequencing (ABI), and primers derived from vector and insert. The insert comprised nucleotides 1 to 549 of SEQ ID NO: 26 and thus an overlap of about 215 nucleotides at the 3' end with the 5'end of the nucleotide sequence of FIG. 8 (SEQ ID NO: 1). Taken together a full-length cDNA encoding the entire phosphatonin molecule shown in SEQ ID NO: 26 and 27, respectively, have now been established. This was confirmed by primer extension experiments that generated a ~150 bp product using a primer (PEP) directed to the new sequence (5' CAC ACA GCT TTG CTT AGT TTT CTC 3' SEQ ID NO: 30) and a 146 bp extension product was expected. Thus, this is very close to the complete cDNA. The primary structure of the entire phosphatonin protein including the motifs previously identified for the partial amino acid sequence in Table 1 as well as additional ones in the N-terminus of the protein are shown in FIG. 15.

The new sequence data, for example polynucleotides encoding the N-terminus and optionally the entire phosphatonin molecule and the complementary strands thereof as well as oligonucleotide primers having the nucleotide sequence of SEQ 28 or 30 are particularly suited for identifying and isolating genomic clones of phosphatonin including promoter sequences from an appropriate library.

While the present invention has been described with reference to the specific embodiments it should be understood by those skilled in the art that various changes may be made and equivalents may be substituted without departing from the true scope and spirit of the invention. In addition, many modifications may be made to adapt to a particular situation, material, composition of matter, process step or steps, to the objective, spirit or scope of the present invention. All such modifications are intended to be within the scope of the claims appended hereto.

The entire disclosure of each document cited (including patents, patent applications, journal articles, abstracts, laboratory manuals, books, or other disclosures) in the Background of the Invention, Detailed Description, and Examples is hereby incorporated herein by reference. Moreover, the sequence listing is herein incorporated by reference.

What is claimed is:

1. A composition, comprising:

a pharmaceutically acceptable carrier; and a polypeptide having phosphatonin activity which com position is characterized by regulating phosphate metabolism the polypeptide comprising an amino acid sequence of SEO ID NO.:27.

* * * * *